United States Patent
Keil et al.

(10) Patent No.: US 9,486,538 B2
(45) Date of Patent: *Nov. 8, 2016

(54) LIPIDS, LIPID COMPLEXES AND USE THEREOF

(71) Applicant: SILENCE THERAPEUTICS GMBH, Berlin (DE)

(72) Inventors: Oliver Keil, Glienicke (DE); Jörg Kaufmann, Berlin (DE); Ansgar Santel, Berlin (DE)

(73) Assignee: SILENCE THERAPEUTICS GMBH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/838,791

(22) Filed: Aug. 28, 2015

(65) Prior Publication Data

US 2015/0359906 A1    Dec. 17, 2015

Related U.S. Application Data

(60) Continuation of application No. 14/286,033, filed on May 23, 2014, now Pat. No. 9,125,820, which is a continuation of application No. 13/742,700, filed on Jan. 16, 2013, now Pat. No. 8,735,453, which is a division of application No. 13/230,085, filed on Sep. 12, 2011, now Pat. No. 8,357,722, which is a division of application No. 11/579,700, filed as application No. PCT/EP2005/004920 on May 6, 2005, now Pat. No. 8,017,804.

(30) Foreign Application Priority Data

May 5, 2004    (EP) .................... 04010700
Dec. 27, 2004    (EP) .................... 04030847

(51) Int. Cl.

| | |
|---|---|
| A61K 47/48 | (2006.01) |
| A61K 47/24 | (2006.01) |
| A61K 47/18 | (2006.01) |
| C12N 15/113 | (2010.01) |
| C07C 279/14 | (2006.01) |
| C12N 15/11 | (2006.01) |
| A61K 9/127 | (2006.01) |

(Continued)

(52) U.S. Cl.
CPC ......... *A61K 47/48815* (2013.01); *A61K 9/127* (2013.01); *A61K 9/1271* (2013.01); *A61K 9/1272* (2013.01); *A61K 31/713* (2013.01); *A61K 47/183* (2013.01); *A61K 47/186* (2013.01); *A61K 47/24* (2013.01); *A61K 47/48046* (2013.01); *A61K 47/48053* (2013.01); *C07C 209/50* (2013.01); *C07C 279/14* (2013.01); *C12N 15/111* (2013.01); *C12N 15/113* (2013.01); *C12N 15/1138* (2013.01); *C12N 2310/14* (2013.01); *C12N 2310/321* (2013.01); *C12N 2320/32* (2013.01)

(58) Field of Classification Search
CPC .. A61K 47/24; A61K 47/183; A61K 47/186; A61K 47/48046; A61K 47/48054; A61K 47/48815; A61K 9/1271; A61K 9/1272; A61K 31/173; C12N 15/111; C12N 15/113; C12N 15/1138; C12N 2310/14; C12N 2310/321; C12N 2320/32; C07C 209/50; C07C 279/14

See application file for complete search history.

(56) References Cited

U.S. PATENT DOCUMENTS 5,476,870 A * 12/1995 Renaut .................. C07C 279/24
                                                  514/482
5,777,153 A     7/1998 Lin et al.

(Continued)

FOREIGN PATENT DOCUMENTS

EP     0 846 680       6/1998
WO     WO 96/10392    4/1996

(Continued)

OTHER PUBLICATIONS

Sirisha et al, ISOR Journal of Pharmacy, 2(5), 2012, 26-38.*

(Continued)

*Primary Examiner* — Shailendra Kumar
(74) *Attorney, Agent, or Firm* — Saliwanchik, Lloyd & Eisenschenk

(57) ABSTRACT

The present invention is related to uses of a composition comprising a pharmaceutically active component and a compound according to formula (I),

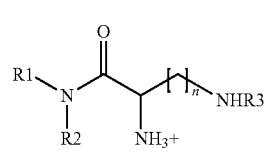

wherein $R_1$ and $R_2$ are each and independently selected from the group comprising alkyl;

n is any integer between 1 and 4;

$R_3$ is an acyl selected from the group comprising lysyl, ornithyl, 2,4-diaminobutyryl, histidyl and an acyl moiety according to formula (II),

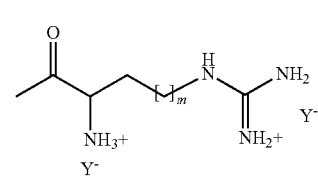

wherein m is any integer from 1 to 3 and
$Y^-$ is a pharmaceutically acceptable anion.

14 Claims, 29 Drawing Sheets

(51) Int. Cl.
  *A61K 31/713* (2006.01)
  *C07C 209/50* (2006.01)

(56) References Cited

U.S. PATENT DOCUMENTS

| | | | |
|---|---|---|---|
| 5,820,873 A | 10/1998 | Choi et al. | |
| 6,358,523 B1 | 3/2002 | Safinya et al. | |
| 6,395,713 B1 | 5/2002 | Beigelman et al. | |
| 6,518,458 B1 | 2/2003 | Moinet et al. | |
| 6,586,410 B1 | 7/2003 | Wheeler et al. | |
| 7,015,040 B2 | 3/2006 | Wolff et al. | |
| 7,196,145 B2 | 3/2007 | Ignatious | |
| 7,282,219 B2 | 10/2007 | Nomura et al. | |
| 8,017,804 B2 | 9/2011 | Keil et al. | |
| 8,357,722 B2 * | 1/2013 | Keil | A61K 47/48046 514/1.1 |
| 8,852,472 B2 | 10/2014 | Keil et al. | |
| 2003/0073640 A1 * | 4/2003 | Beigelman | A61K 47/48023 514/44 R |
| 2009/0074852 A1 | 3/2009 | Kaufmann et al. | |
| 2010/0062967 A1 | 3/2010 | Keil et al. | |
| 2011/0294871 A1 | 12/2011 | Keil et al. | |
| 2015/0031752 A1 | 1/2015 | Keil et al. | |

FOREIGN PATENT DOCUMENTS

| | | |
|---|---|---|
| WO | WO 96/40964 | 12/1996 |
| WO | WO 97/03939 | 2/1997 |
| WO | WO 98/44909 | 10/1998 |
| WO | WO 98/51285 | 11/1998 |
| WO | WO 99/04819 | 2/1999 |
| WO | WO 99/05094 | 2/1999 |
| WO | WO 01/05374 | 1/2001 |
| WO | WO 01/74397 | 10/2001 |
| WO | WO 01/80900 | 11/2001 |
| WO | WO 02/34236 | 5/2002 |
| WO | WO 2004/012680 | 2/2004 |
| WO | WO 2005/105152 | 11/2005 |
| WO | WO 2006/053646 | 5/2006 |
| WO | WO 2006/069782 | 7/2006 |
| WO | WO 2006/074546 | 7/2006 |
| WO | WO 2007/121947 | 11/2007 |

OTHER PUBLICATIONS

Office Action dated Jan. 3, 2011 in U.S. Appl. No. 11/722,948.
Final Office Action dated Jan. 11, 2012 in U.S. Appl. No. 11/722,948.
Office Action dated Apr. 5, 2012 in U.S. Appl. No. 12/297,611.
Osmosis Lab, "Cell Membrane Permeability and Osmosis" retrieved from http://bioweb.wku.edu/faculty/crawford/osmosis.htm on Mar. 28, 2012, pp. 1-5.
Ozturk, S. et al. "Effect of Medium Osmolarity on Hybridoma Growth, Metabolism, and Antibody Production" *Biotechnology and Bioengineering*, 1991, pp. 989-993, vol. 37.
Masson, C. et al. "pH-sensitive PEG lipids containing orthoester linkers: new potential tools for nonviral gene delivery" *Journal of Controlled Release*, 2004, pp. 423-434, vol. 99.
Oishi, M. et al. "Lactosylated Poly(ethylene glycol)-siRNA Conjugate through Acid-Labile β-Thiopropionate Linkage to Construct pH-Sensitive Polyion Complex Micelles Achieving Enhanced Gene Silencing in Hepatoma Cells" *Journal of American Chemical Society*, 2005, pp. 1624-1625, vol. 127.
Byk, G. et al. "Genetic Chemistry: Tools for Gene Therapy Coming from Unexpected Directions" *Drug Development Research*, 2000, pp. 566-572, vol. 50, XP-009046314.
Roe, E. T. et al. "Fatty Acid Amides . . . 9,1O-Oihydroxystearic Acids", *Journal of the American Cancer Society*, 1949, pp. 2215-2218, vol. 71, XP-002385161.
Bedenbaugh, A. O. et al. "Synthesis of aldehydes and . . . carboxylic acids via imines", *Journal of the American Cancer Society*, 1970, pp. 5774-5775, vol. 92, XP-002385162.
Santel, A. et al. "A novel siRNA-lipoplex technology for RNA interference in the mouse vascular endothelium" *Gene Therapy*, 2006, pp. 1-13.
Folkman, J. "Angiogenesis" *Annu. Rev. Med*, 2006, pp. 1-18, vol. 57.
Ferrara, N. et al. "Angiogenesis as a therapeutic target" *Nature*, Dec. 15, 2005, pp. 967-974, vol. 438.
Kerbel, R.S. "Molecular Origins of Cancer Tumor Angiogenesis" *The New England Journal of Medicine*, May 8, 2008, pp. 2039-2049, vol. 358, No. 19.
Carter, S.K. et al. "Chemotherapy of Cancer", second edition, John Wiley & Sons, N.Y., N.Y., 1981, pp. 362-365.

* cited by examiner

β-arginyl-2,3-diaminopropionic acid-N-palmityl-N-oleyl-amide tri-hydrochloride

β-arginyl-2,3-diaminopropionic acid-N-lauryl-N-myristyl-amide tri-hydrochloride

ε-arginyl-lysine-*N*-lauryl-*N*-myristyl-amide tri-hydrochloride [#15]

FIG. 20A, FIG. 20B, FIG. 20C

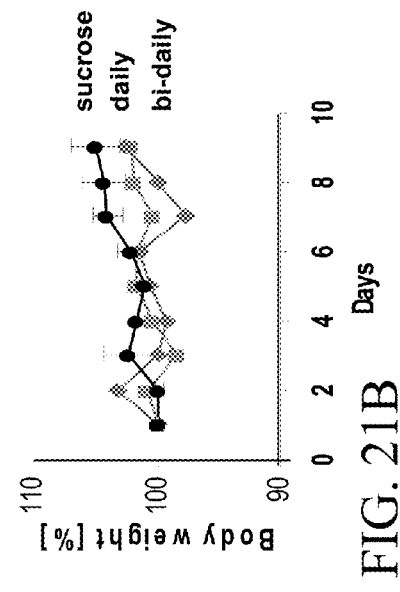
FIG. 21A
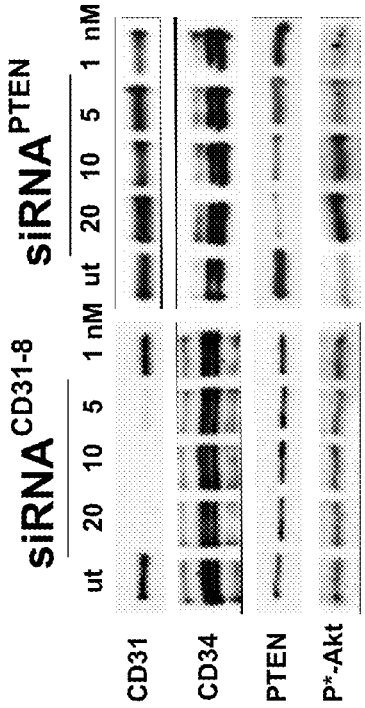
FIG. 21B
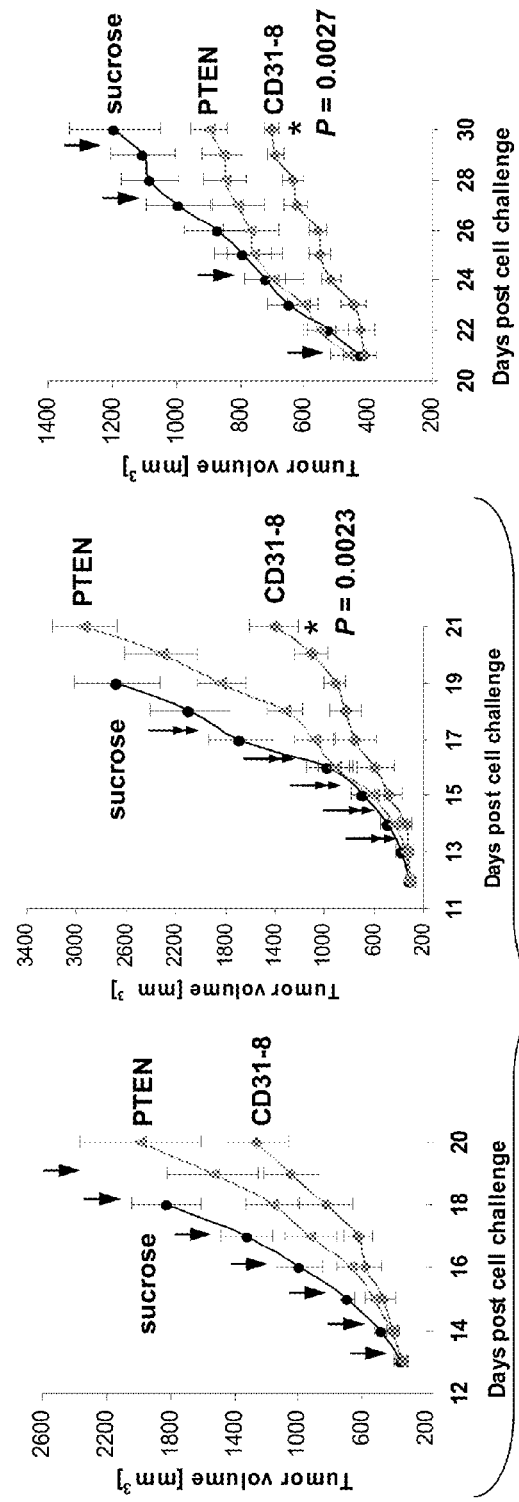
FIG. 21C
FIG. 21D

LIPIDS, LIPID COMPLEXES AND USE THEREOF

CROSS-REFERENCE TO RELATED APPLICATIONS

This application is a continuation of U.S. Ser. No. 14/286,033, filed May 23, 2014, now U.S. Pat. No. 9,125,820, which is a continuation of U.S. Ser. No. 13/742,700, filed Jan. 16, 2013, now U.S. Pat. No. 8,735,453, which is a divisional of U.S. Ser. No. 13/230,085, filed Sep. 12, 2011, now U.S. Pat. No. 8,357,722, which is the divisional of U.S. Ser. No. 11/579,700, filed May 22, 2008, now U.S. Pat. No. 8,017,804, which is the U.S. national stage application of International Patent Application No. PCT/EP2005/004920, filed May 6, 2005, the disclosures of which are hereby incorporated by reference in their entirety, including all figures, tables and amino acid or nucleic acid sequences.

The present invention is related to cationic lipids, compositions containing the same and use thereof as well as a method for transferring chemical compounds into cells.

Both molecular biology as well as molecular medicine heavily rely on the introduction of biologically active compounds into cells. Such biologically active compounds typically comprise, among others, DNA, RNA as well as peptides and proteins, respectively. The barrier which has to be overcome is typically a lipid bilayer which has a negatively charged outer surface. In the art, a number of technologies have been developed to penetrate the cellular membrane and to thus introduce the biologically active compounds. Some methods conceived for laboratory use, however, cannot be used in the medical field and are more particularly not suitable for drug delivery. For example, electroporation and ballistic methods known in the art, would, if at all, only allow a local delivery of biologically active compounds. Apart from said lipid bilayer cellular membranes also comprise transporter systems. Accordingly, efforts were undertaken to use this kind of transporter systems in order to transfer the biologically active compounds across the cell membrane. However, due to the specificity or cross-reactivity of such transporter systems, their use is not a generally applicable method.

A more generally applicable approach described in the art for transferring biologically active compounds into cells, is the use of viral vectors. However, viral vectors can be used only for transferring genes efficiently into some cell types; but they cannot be used to introduce chemically synthesised molecules into the cells.

An alternative approach was the use of so called liposomes (Bangham, J. Mol. Biol. 13, 238-252). Liposomes are vesicles which are generated upon association of amphiphilic lipids in water. Liposomes typically comprise concentrically arranged bilayers of phospholipids. Depending on the number of layers liposomes can be categorised as small unilamelar vesicles, multilamelar vesicles and large multilamelar vesicles. Liposomes have proven to be effective delivery agents as they allow one to incorporate hydrophilic compounds into the aqueous intermediate layers, whereas hydrophobic compounds are incorporated into the lipid layers. It is well known in the art that both the composition of the lipid formulation as well as its method of preparation have an effect on the structure and size of the resultant lipid aggregates and thus on the liposomes. Liposomes are also known to incorporate cationic lipids.

Cationic lipids have, apart from being components of liposomes, also attracted considerable attention as they may as such be used for cellular delivery of biopolymers. Using cationic lipids any anionic compound can be encapsulated essentially in a quantitative manner due to electrostatic interaction. In addition, it is believed that the cationic lipids interact with the negatively charged cell membranes initiating cellular membrane transport. It has been found that the use of a liposomal formulation containing cationic lipids or the use of cationic lipids as such together with a biologically active compound requires a heuristic approach as each formulation is of limited use because it typically can deliver plasmids into some but not all cell types, usually in the absence of serum.

Charge and/or mass ratios of lipids and the biologically active compounds to be transported by them have turned out to be a crucial factor in the delivery of different types of said biologically active compounds. For example, it has been shown that lipid formulations suitable for plasmid delivery comprising 5,000 to 10,000 bases in size, are generally not effective for the delivery of oligonucleotides such as synthetic ribozymes or antisense molecules typically comprising about 10 to about 50 bases. In addition, it has recently been indicated that optimal delivery conditions for antisense oligonucleotides and ribozymes are different, even in the same cell type.

U.S. Pat. No. 6,395,713 discloses cationic lipid based compositions which typically consist of a lipophilic group, a linker and a head group and the use of such compositions for transferring biologically active compounds into a cell.

The problem underlying the present invention was to provide a means for introducing biologically active compounds into cells, preferably animal cells. A further problem underlying the present invention is to provide a delivery agent for nucleic acids, particularly small nucleic acids such as siRNA, siNA and RNAi or aptamers and spiegelmers.

These problems are solved by the subject matter of the independent claims attached hereto. Preferred embodiments may be taken from the attached claims dependent thereon.

In a first aspect the problem underlying the present invention is solved by a compound according to formula (I),

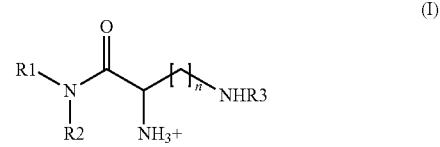

(I)

wherein $R_1$ and $R_2$ are each and independently selected from the group comprising alkyl;
n is any integer between 1 and 4;
$R_3$ is an acyl selected from the group comprising lysyl, ornithyl, 2,4-diaminobutyryl, histidyl and an acyl moiety according to formula (II),

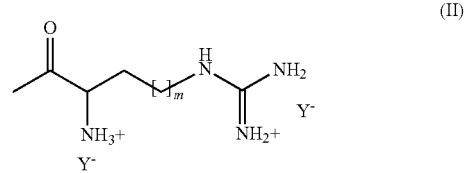

(II)

wherein m is any integer from 1 to 3 and
$Y^-$ is a pharmaceutically acceptable anion.

In an embodiment $R_1$ and $R_2$ are each and independently selected from the group comprising lauryl, myristyl, palmityl and oleyl.

In an embodiment $R_1$ is lauryl and $R_2$ is myristyl; or $R_1$ is palmityl and $R_2$ is oleyl.

In an embodiment m is 1 or 2.

In an embodiment the compound is a cationic lipid, preferably in association with an anion $Y^-$.

In an embodiment $Y^-$ is selected from the group comprising halogenids, acetate and trifluoroacetate.

In an embodiment the compound is selected from the group comprising:

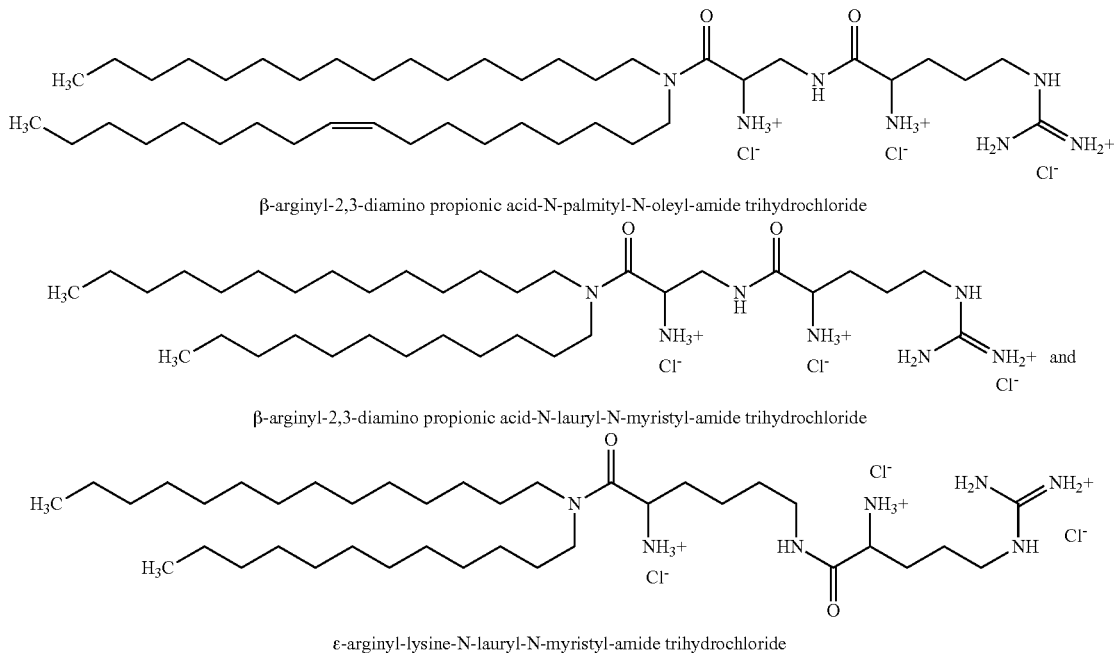

In a second aspect the problem underlying the present invention is solved by a composition comprising as a lipid component a compound according to the first aspect, and a carrier.

In an embodiment the composition comprises a further constituent.

In a third aspect the problem underlying the present invention is solved by a pharmaceutical composition comprising a compound according to the first aspect and a pharmaceutically active compound and preferably a pharmaceutically acceptable carrier.

In an embodiment of the second and third aspect the pharmaceutically active compound and/or the further constituent is selected from the group comprising peptides, proteins, oligonucleotides, polynucleotides and nucleic acids.

In an embodiment of the second and third aspect the protein is an antibody, preferably a monoclonal antibody.

In an embodiment of the second and third aspect the nucleic acid is selected from the group comprising DNA, RNA, PNA and LNA.

In an embodiment of the second and third aspect the nucleic acid is a functional nucleic acid, whereby preferably the functional nucleic acid is selected from the group comprising RNAi, siRNA, siNA, antisense nucleic acid, ribozymes, aptamers and spiegelmers.

In an embodiment of the second and third aspect the composition further comprises at least one helper lipid component, whereby preferably the helper lipid component is selected from the group comprising phospholipids and steroids.

In a preferred embodiment of the second and third aspect the helper lipid component is selected from the group comprising 1,2-diphytanoyl-sn-glycero-3-phosphoethanolamine and 1,2-dioleyl-sn-glycero-3-phosphoethanolamine.

In an embodiment of the second and third aspect the content of the helper lipid component is from about 20 mol % to about 80 mol % of the overall lipid content of the composition.

In a preferred embodiment of the second and third aspect the content of the helper lipid component is from about 35 mol % to about 65 mol %.

In an embodiment of the second and third aspect the lipid is β-arginyl-2,3-diamino propionic acid-N-palmityl-N-oleyl-amide trihydrochloride, and the helper lipid is 1,2-diphytanoyl-sn-glycero-3-phosphoethanolamine.

In a preferred embodiment of the second and third aspect the lipid is 50 mol % and the helper lipid is 50 mol % of the overall lipid content of the composition.

In an embodiment of the second and third aspect the composition contains at least two helper lipids.

In a preferred embodiment of the second and third aspect at least one helper lipid comprises a moiety which is selected from the group comprising a PEG moiety, a HEG moiety, a polyhydroxyethyl starch (polyHES) moiety and a polypropylene moiety, whereby such moiety preferably provides a molecule weight from about 500 to 10000 Da, more preferably from about 2000 to 5000 Da.

In a preferred embodiment of the second and third aspect the helper lipid comprising the PEG moiety is selected from the group comprising 1,2-distearoyl-sn-glycero-3-phosphoethanolamine, 1,2-dialkyl-sn-glycero-3-phosphoethanolamine; and Ceramide-PEG.

In a more preferred embodiment of the second and third aspect the PEG moiety has a molecular weight from about 500 Da to 10000 Da, preferably from about 2,000 to 5,000 Da, more preferably a molecular weight of 2,000 Da.

In an even more preferred embodiment of the second and third aspect the composition comprises as the lipid component β-arginyl-2,3-diamino propionic acid-N-palmityl-N-oleyl-amide trihydrochloride, as a first helper lipid 1,2- diphytanoyl-sn-glycero-3-phosphoethanolamine and as a second helper lipid 1,2-distearoyl-sn-glycero-3-phosphoethanolamine-PEG2000.

In a still more preferred embodiment of the second and third aspect the content of the second helper lipid is from about 0.05 mol % to 4.9 mol %, preferably about 1 to 3 mol %.

In a still further more preferred embodiment of the second and third aspect the content of the lipid is from 45 mol % to 50 mol %, the content of the first helper lipid is from 45 to 50 mol % and, under the proviso that there is a PEGylated second helper lipid, the content of the second helper lipid is from about 0.1 mol % to about 5 mol %, preferably from about 1 to 4 mol % and more preferably about 2%, whereby the sum of the content of the lipid, of the lipid, of the first helper lipid and of the second helper lipid is 100 mol % and whereby the sum of the first helper lipid and the second helper lipid is 50 mol %.

In a preferred embodiment of the second and third aspect the composition contains either
  a) 50 mol % of β-arginyl-2,3-diamino propionic acid-N-palmityl-N-oleyl-amide trihydrochloride,
    48 mol % of 1,2-diphytanoyl-sn-glycero-3-phosphoethanolamine; and
    2 mol % 1,2-distearoyl-sn-glycero-3-phosphoethanolamine-PEG2000.
or
  b) 50 mol % of β-L-arginyl-2,3-L-diamino propionic acid-N-palmityl-N-oleyl-amide trihydrocloride,
    49 mol % 1,2-diphytanoyl-sn-glycero-3-phosphoethanolamine; and
    1 mol % N(Carbonyl-methoxypolyethylenglycol-2000)-1,2-distearoyl-sn-glycero-3-phosphoethanolamine, preferably the sodium salt thereof.

In a preferred embodiment of the second and third aspect the functional nucleic acid is a double-stranded ribonucleic acid, wherein the composition further comprises a nucleic acid, preferably a functional nucleic acid which is more preferably a double-stranded ribonucleic acid and most preferably a nucleic acid selected from the group comprising RNAi, siRNA, siNA, antisense nucleic acid and ribozyme, whereby preferably the molar ration of RNAi to cationic lipid is from about 0 to 0.075, preferably from about 0.02 to 0.05 and even more preferably 0.037.

In a preferred embodiment of the second and third aspect the compound and/or the helper lipid component is present as a dispersion in an aqueous medium.

In a preferred embodiment of the second and third aspect the compound and/or the helper lipid component is present as a solution in a water miscible solvent, whereby preferably the solvent is selected from the group comprising ethanol and tert.-butanol.

In a preferred embodiment of the second and third aspect the functional nucleic acid is a double-stranded ribonucleic acid, preferably a nucleic acid selected from the group comprising RNAi, siRNA, siNA, antisense nucleic acid and ribozyme, and whereby preferably the molar ratio of RNAi to cationic lipid is from about 0 to 0.075, preferably from about 0.02 to 0.05 and even more preferably 0.037.

In a preferred embodiment of the second and third aspect the composition contains a nucleic acid, whereby the charge ratio of nucleic acid backbone phosphates to cationic lipid nitrogen atoms is about from 1:1.5-7, preferably 1:4.

In a preferred embodiment of the second and third aspect the size of the particles in the dispersion is about 120 nm.

In a preferred embodiment of the second and third aspect the dispersion is a stock dispersion containing about 1 to 100 µM SiRNA, whereby preferably the stock dispersion is diluted in vivo or in vitro by 1:100 to 1:10000, more preferably 1:1000.

In a fourth aspect the problem underlying the present invention is solved by the use of a compound according to the first aspect or a composition according to the second or third aspect, for the manufacture of a medicament, preferably for the treatment of cancer and/or cardiovascular related diseases.

In an embodiment of the fourth aspect the medicament is for the treatment of cancer, whereby preferably the cancer is selected from the group comprising solid and non-solid tumors and whereby more preferably the solid tumor is selected from the group comprising pancreatic cancer, breast cancer, prostate cancer, lung cancer, colon cancer and hepatocellular carcinoma.

In an embodiment of the fourth aspect the cancer involves a process selected from the group comprising angiogenesis and neoangiogenesis.

In an embodiment of the fourth aspect the medicament is for administering the nucleic acid to a cell selected from the group comprising endothelial cells, epithelial cells and tumor cells, preferably the cell is an endothelial cell.

In an embodiment of the fourth aspect the endothelial cells are endothelial cells of vasculature.

In an embodiment of the fourth aspect the vasculature is vasculature arising from neoangiogenesis, preferably tumor associated neoangiogenesis.

In an embodiment of the fourth aspect the vasculature is selected from the group comprising liver vasculature, heart vasculature, kidney vasculature, pancreactic vasculature and lung vasculature.

In an embodiment of the fourth aspect the medicament is for systemic administration.

In an embodiment of the fourth aspect the medicament is for local administration.

In an embodiment of the fourth aspect the medicament is for the treatment of cardiovascular related diseases, whereby the cardiovascular diseases are selected from the group comprising coronary heart disease, heart failure, hypertension, thrombosis, myocardial infarction, ischemic heart diseases such as angina pectoris and arteriosclerosis.

In an embodiment of the fourth aspect the medicament is for the treatment of angiogenesis related diseases. Preferably such angiogenesis is related to the following organs and diseases where angiogenesis is described as causing such disease and, therefore, allowing for the use of the composition according to the present invention (Carmeliet P., Nature Medicine 9, 653-660 (2003)):
  blood vessels vascular malformations, DiGeorge syndrome, HHT, cavernous hemangioma, artherosclerosis, transplant arteriopathy, hypertension, diabetes, restenosis
  adipose tissue obesity
  skin psoriasis, warts, allergic dermatitis, scar keloids, pyogenic granulomas, blistering disease, Kaposi sarcoma in AIDS patients, hair loss, skin purpura, telangiectasia, venous lake formation
  eye persistent hyperplastic vitreous syndrome, diabetic retinopathy, retinopathy of prematurity, choroidal neovascularization
  lung primary pulmonary hypertension, asthma, nasal polyps, neonatal respiratory distress, pulmonary fibrosis, emphysema
  intestines inflammatory bowel and periodontal disease, ascites, peritoneal adhesions reproductive system endometriosis, uterine bleeding, ovarian cysts, ovarian hyperstimulation, pre-eclampsia bone, joints arthritis, synovitis, osteomyelitis, osteophyte formation, osteoporosis, impaired bone fracture healing nervous system Alzheimer disease, amyotrophic lateral sclerosis, diabetic neuropathy, stroke gastrointestinal gastric or oral ulcerations, Crohn disease kidney nephropathy In a fifth aspect the problem underlying the present invention is solved by the use of a compound according to the first aspect and/or the composition according to the second and/or third aspect for the manufacture of a diagnostic agent.

In a sixth aspect the problem underlying the present invention is solved by the use of a compound according to the first aspect or a composition according to the second and/or third aspect, as a transferring agent.

In an embodiment of the sixth aspect the transferring agent transfers a pharmaceutically active component and/or a further constituent into a cell, preferably a mammalian cell and more preferably a human cell.

In an embodiment of the sixth aspect the cell is an endothelial cell, preferably a vascular associated endothelial cell.

In a seventh aspect the problem underlying the present invention is solved by a method for transferring a pharmaceutically active compound and/or a further constituent into a cell or across a membrane, preferably a cell membrane, comprising the following steps:
  providing the cell or the membrane;
  providing a compound according to any of the first aspect;
  providing the pharmaceutically active compound and/or the further constituent; and
  contacting the cell or the membrane with the pharmaceutically active compound and/or the further constituent, and the compound according to the first aspect.

In an eighth aspect the problem underlying the present invention is solved by a method for transferring a pharmaceutically active compound and/or a further constituent into a cell or across a membrane, preferably a cell membrane, providing the following steps:
  providing the cell or the membrane;
  providing a composition according to the second or third aspect; and
  contacting the cell or the membrane with the composition according to the second or third aspect.

In an embodiment of the seventh or eighth aspect the pharmaceutically active compound comprising as a further step:
  detecting the pharmaceutically active compound and/or the further constituent in the cell and/or beyond the membrane.

In a ninth aspect the problem underlying the present invention is solved by a method for the synthesis of N-palmityl-oleylamine comprising the following steps:
  providing oleic acid;
  providing palmitylamine;
  reacting the oleic acid and the palmitylamine to form N-palmityl-oleoylamide; and
  reducing the N-palmityl-oleoylamide to N-palmityl-oleylamine,
whereby the oleic acid is at least 90%, more preferably 95% and most preferably 99% pure, whereby the percentage is the molar ratio of oleic acid and any fatty acid different from oleic acid.

In an embodiment of the ninth aspect the oleic acid and the palmitylamine are reacted at room temperature.

In an embodiment of the ninth aspect the oleic acid is subject to a pre-treatment prior to reacting it with the palmitylamine, whereby the pre-treatment comprises reacting the oleic acid with ethylchloroformate, preferably in anhydrous dichloromethane or anhydrous tetrahydrofuran.

In an embodiment of the ninth aspect the reaction is performed at 0° C., preferably under inert gas.

In an embodiment of the ninth aspect the reaction is further reacted with an acid scavenger, whereby the acid scavenger is preferably selected from the group comprising triethylamine, diisopropylethylamine and pyridine.

In an embodiment of the ninth aspect the molar ratio of chloroformic acid ethyl ester, oleic acid, triethylamine and palmitylamine is about 1-1.05:1:1:1-3:1-1.10.

In an embodiment of the ninth aspect the reduction of the N-palmityl-oleoylamide to N-palmity-oleylamine is performed using $LiAlH_4$.

In an embodiment of the ninth aspect upon reacting the oleic acid with the palmitylamine, the reaction is washed, precipitated and the precipitate thus obtained optionally re-crystallised.

In a tenth aspect the problem underlying the present invention is solved by the use of a compound according to the first aspect or a composition according to the second or third aspect for systemic administration, preferably systemic administration to a vertebrate.

In an embodiment of the tenth aspect the vertebrate is a mammal, more preferably a mammal selected from the group comprising mouse, rat, guinea pig, cat, dog, monkey and man.

The compounds according to the present invention can, as depicted in FIG. 1, be regarded as to comprise a lipophilic group formed by the R1-N—R2 moiety, a linker group formed by the $C(O)—CH(NH_3^+)(CH_2)_n$—NH moiety and a head group formed by the R3 moiety. The present inventor has surprisingly found that this kind of compound exhibiting a positive charge at the linker group is particularly suitable to transfer biologically active compounds over a cell membrane and preferably into cells, more preferably animal cells. Also, the present inventor has surprisingly found that the transfer mediated by the compounds according to the present invention will be particularly effective if the biologically active compound is a nucleic acid, more preferably siRNA and siNA.

As preferably used herein, the term alkyl refers to a saturated aliphatic radical containing from 8 to 20 carbon atoms, preferably 12 to 18 carbon atoms, or a mono- or polyunsaturated aliphatic hydrocarbon radical containing from 8 to 30 carbon atoms, containing at least one double and triple bond, respectively. Thus, in a preferred embodiment, the term alkyl also comprises alkenyl and alkinyl Alky refers to both branched and unbranched, i.e. non-linear or straight chain alkyl groups. Preferred straight chain alkyl groups contain from 8 to 30 carbon atoms. More preferred straight chain alkyl groups contain from 12 to 18 carbon atoms. Preferred branched alkyl groups contain from 8 to 30 carbon atoms, whereby the number from 8 to 30 carbon atoms refers to the number of carbon atoms forming the backbone of such branched alkyl group. The backbone of the branched alkyl group contains at least one alkyl group as branching off from the backbone, with the alkyl group being defined as herein, more preferably with the alkyl group comprising short chain alkyl groups, more preferably comprising from 1 to 6, even more preferred 1 to 3 and most preferred 1 C atom. More preferred are branched alkyl groups containing 12 to 18 carbon atoms in the backbone with the branching alkyl groups being defined as in the foregoing. A particularly preferred alkyl group is the phytanyl group.

In an alternative embodiment, the alkyl is an unsaturated branched or unbranched alkyl group as defined above. More preferably, such unsaturated aliphatic hydrocarbon radical contains 1, 2 or 3 or 4 double bonds, whereby a radical having one double bond is particularly preferred. Most preferred is oleyl which is C18:1delta9, i. e. an aliphatic hydrocarbon radical having 18 C atoms, whereby at position 9 a cis configured double bond is presented rather than a single bond linking C atom number 9 to C atom number 10.

As used herein, n is any integer between 1 and 4, which means that n may be 1, 2, 3 and 4. As used herein, m is any integer between 1 and 3, which means that m may be 1, 2 and 3.

It is to be understood that the compounds according to the present invention are preferably cationic lipids. More preferably, any of the NH or $NH_2$ groups present in the compounds according to the present invention are present in a protonated form. Typically, any positive charge of the compound according to the present invention is compensated by the presence of an anion. Such anion can be a monovalent or polyvalent anion. Preferred anions are halides, acetate and trifluoroacetate. Halides as used herein are preferably fluorides, chlorides, iodides and bromides. Most preferred are chlorides. Upon association of the cationic lipid and the biologically active compound to be transferred into a cell, the halide anion is replaced by the biologically active compound which preferably exhibits one or several negative charges, although it has to be acknowledged that the overall charge of the biologically active compound is not necessarily negative.

It is to be acknowledged that any compound according to formula (I) comprises at least two asymmetric C atoms. It is within the present invention that any possible enantiomer of such compound is disclosed herein, i. e. in particular the R—R; S—S; R—S and S—R enantiomer.

The compounds according to the present invention can form a composition or be part of a composition, whereby such composition comprises a carrier. In such composition which is also referred to herein as lipid composition the compounds according to the present invention are also referred to as the lipid component(s). Such carrier is preferably a liquid carrier. Preferred liquid carriers are aqueous carriers and non-aqueous carriers. Preferred aqueous carriers are water, aqueous buffer systems, more preferably buffer systems having a physiological buffer strength and physiological salt concentration(s). Preferred non-aqueous carriers are solvents, preferably organic solvents such as ethanol, tert.-butanol. Without wishing to be bound by any theory, any water miscible organic solvent can, in principle, be used. It is to be acknowledged that the composition, more particularly the lipid composition can thus be present as or form liposomes.

The composition according to the present invention may comprise one or more helper lipids which are also referred to herein as helper lipid components. The helper lipid components are preferably selected from the group comprising phospholipids and steroids. Phospholipids are preferably di- and monoester of the phosphoric acid. Preferred members of the phospholipids are phosphoglycerides and sphingolipids. Steroids, as used herein, are naturally occurring and synthetic compounds based on the partially hydrogenated cyclopenta[a]phenanthrene. Preferably, the steroids contain 21 to 30 C atoms. A particularly preferred steroid is cholesterol.

Particularly preferred helper lipids are 1,2-diphytanoyl-sn-glycero-3-phosphoethanolamine (DPhyPE) and 1,2-dioleoyl-sn-glycero-3-phosphoethanolamine (DOPE).

Particularly preferred compositions according to the present invention comprise any of β-arginyl-2,3-diaminopropionic acid-N-palmityl-N-oleyl-amide trihydrochloride [#6], β-arginyl-2,3-diaminopropionic acid-N-lauryl-N-myristyl-amide trihydrochloride [#11] or ε-arginyl-lysine-N-lauryl-N-myristyl-amide trihydrochloride [#15] in combination with DPhyPE, whereby the content of DPhyPE is preferably 80 mol %, 65 mol %, 50 mol % and 35 mol %, whereby the term mol % refers to the percentage of the overall lipid content of the composition, i. e. the lipid content of the composition including the cationic lipid according to the present invention and any additional lipid, including, but not limited to, any helper lipid.

It is within the present invention that the composition according to the present invention preferably comprises the compound according to the present invention and/or one or several of the helper lipid(s) as disclosed herein, whereby either the compound according to the present invention, i.e. the cationic lipid, and/or the helper lipid component is present as a dispersion in an aqueous medium. Alternatively, the compound according to the present invention, i.e. the cationic lipid, and/or the helper lipid component is/are present as a solution in a water miscible solvent. As an aqueous medium, preferably any of the aqueous carrier as disclosed herein is used. Preferred water miscible solvents are any solvents which form a homogenous phase with water in any ratio. Preferred solvents are ethanol and tert-butanol. It is to be acknowledged that the composition, more particularly the lipid composition can thus be present as or form liposomes.

It is to be acknowledged that the composition according to the present invention in its various embodiments may also be used as a pharmaceutical composition. In the latter case, the pharmaceutical composition comprises a pharmaceutically active compound and optionally a pharmaceutically acceptable carrier. Such pharmaceutically acceptable carrier may, preferably, be selected from the group of carriers as defined herein in connection with the composition according to the present invention. It will be understood by those skilled in the art that any composition as described herein may, in principle, be also used as a pharmaceutical composition provided that its ingredients and any combination thereof is pharmaceutically acceptable. A pharmaceutical composition comprises a pharmaceutically active compound. Such pharmaceutically active compound can be the same as the further constituent of the composition according to the present invention which is preferably any biologically active compound, more preferably any biologically active compound as disclosed herein. The further constituent, pharmaceutically active compound and/or biologically active compound are preferably selected from the group comprising peptides, proteins, oligonucleotides, polynucleotides and nucleic acids.

Preferably, any such biologically active compound is a negatively charged molecule. The term negatively charged molecule means to include molecules that have at least one negatively charged group that can ion-pair with the positively charged group of the cationic lipid according to the present invention, although the present inventor does not wish to be bound by any theory. In principle, the positive charge at the linker moiety could also have some effect on the overall structure of either the lipid as such or any complex formed between the cationic lipid and the negatively charged molecule, i.e. the biologically active compound. Apart from that, the additional positive charge introduced into the lipid according to the present invention compared to the cationic lipids disclosed in U.S. Pat. No. 6,395,713, should contribute to an increased toxicity of this lipid as taught by Xu Y, Szoka F C Jr.; Biochemistry; 1996 May 7, 35 (18): 5616-23. In contrast to what the one skilled in the art would have expected from this document of the prior art the compounds according to the present invention are particularly suitable for the various purposes disclosed herein and are in particular devoid of any increased toxicity.

A peptide as preferably used herein is any polymer consisting of at least two amino acids which are covalently linked to each other, preferably through a peptide bond. More preferably, a peptide consists of two to ten amino acids. A particularly preferred embodiment of the peptide is an oligopeptide which even more preferably comprises from about 10 to about 100 amino acids. Proteins as preferably used herein are polymers consisting of a plurality of amino acids which are covalently linked to each other. Preferably such proteins comprise about at least 100 amino acids or amino acid residues.

A preferred protein which may be used in connection with the cationic lipid and the composition according to the present invention, is any antibody, preferably any monoclonal antibody.

Particularly preferred biologically active compounds, i.e. pharmaceutically active compounds and such further constituent as used in connection with the composition according to the present invention are nucleic acids. Such nucleic acids can be either DNA, RNA, PNA or any mixture thereof. More preferably, the nucleic acid is a functional nucleic acid. A functional nucleic acid as preferably used herein is a nucleic acid which is not a nucleic acid coding for a peptide and protein, respectively. Preferred functional nucleic acids are siRNA, siNA, RNAi, antisense-nucleic acids, ribozymes, aptamers and spiegelmers which are all known in the art.

siRNA are small interfering RNA as, for example, described in international patent application PCT/EP03/08666. These molecules typically consist of a double-stranded RNA structure which comprises between 15 to 25, preferably 18 to 23 nucleotide pairs which are base-pairing to each other, i.e. are essentially complementary to each other, typically mediated by Watson-Crick base-pairing. One strand of this double-stranded RNA molecule is essentially complementary to a target nucleic acid, preferably a mRNA, whereas the second strand of said double-stranded RNA molecule is essentially identical to a stretch of said target nucleic acid. The siRNA molecule may be flanked on each side and each stretch, respectively, by a number of additional oligonucleotides which, however, do not necessarily have to base-pair to each other.

RNAi has essentially the same design as siRNA, however, the molecules are significantly longer compared to siRNA. RNAi molecules typically comprise 50 or more nucleotides and base pairs, respectively.

A further class of functional nucleic acids which are active based on the same mode of action as siRNA and RNAi is siNA. siNA is, e.g., described in international patent application PCT/EP03/074654. More particularly, siNA corresponds to siRNA, whereby the siNA molecule does not comprise any ribonucleotides.

Antisense nucleic acids, as preferably used herein, are oligonucleotides which hybridise based on base complementarity with a target RNA, preferably mRNA, thereby activating RNaseH. RNaseH is activated by both phosphodiester and phosphothioate-coupled DNA. Phosphodiester-coupled DNA, however, is rapidly degraded by cellular nucleases with exception of phosphothioate-coupled DNA. Antisense polynucleotides are thus effective only as DNA-RNA hybrid complexes. Preferred lengths of antisense nucleic acids range from 16 to 23 nucleotides. Examples for this kind of antisense oligonucleotides are described, among others, in U.S. Pat. No. 5,849,902 and U.S. Pat. No. 5,989,912.

A further group of functional nucleic acids are ribozymes which are catalytically active nucleic acids preferably consisting of RNA which basically comprise two moieties. The first moiety shows a catalytic activity, whereas the second moiety is responsible for the specific interaction with the target nucleic acid. Upon interaction between the target nucleic acid and the said moiety of the ribozyme, typically by hybridisation and Watson-Crick base-pairing of essentially complementary stretches of bases on the two hybridising strands, the catalytically active moiety may become active which means that it cleaves, either intramolecularly or intermolecularly, the target nucleic acid in case the catalytic activity of the ribozyme is a phosphodiesterase activity. Ribozymes, the use and design principles are known to the ones skilled in the art and, for example, described in Doherty and Doudna (Annu Ref. Biophys. Biomolstruct. 2000; 30: 457-75).

A still further group of functional nucleic acids are aptamers. Aptamers are D-nucleic acids which are either single-stranded or double-stranded and which specifically interact with a target molecule. The manufacture or selection of aptamers is, e.g., described in European patent EP 0 533 838. In contrast to RNAi, siRNA, siNA, antisense-nucleotides and ribozymes, aptamers do not degrade any target mRNA but interact specifically with the secondary and tertiary structure of a target compound such as a protein. Upon interaction with the target, the target typically shows a change in its biological activity. The length of aptamers typically ranges from as little as 15 to as much as 80 nucleotides, and preferably ranges from about 20 to about 50 nucleotides.

Another group of functional nucleic acids are spiegelmers as, for example, described in international patent application WO 98/08856. Spiegelmers are molecules similar to aptamers. However, spiegelmers consist either completely or mostly of L-nucleotides rather than D-nucleotides in contrast to aptamers. Otherwise, particularly with regard to possible lengths of spiegelmers, the same applies to spiegelmers as outlined in connection with aptamers.

As mentioned previously, the present inventor has surprisingly found that the compound according to the present invention and the respective compositions comprising such compound can be particularly effective in transferring RNAi, and more particularly siRNA and siNA into a cell. It is to be noted that although not wishing to be bound by any theory, due to the particular mol percentages of the helper lipid(s) contained in the lipid compositions according to the present invention, which helper lipid can be either a PEG-free helper lipid or in particular a PEG-containing helper lipid, surprising effects can be realised, more particularly if the content of any of this kind of helper lipid is contained within the concentration range specified herein. In connection therewith, it is particularly noteworthy that if the composition according to the present invention contains a helper lipid comprising a PEG moiety, any delivery or transfection action using such PEG-derived helper lipid containing composition is particularly effective in delivering nucleic acid, particularly RNAi molecules, most particularly siRNA, siNA, antisense nucleotides and ribozymes. The reason for this is that the present inventors have surprisingly found that liposomes containing more than about 4% of PEG-containing helper lipid(s) are not active, whereas liposomes with less than 4% (preferably less than 3%) do mediate functional delivery. Basically, the present inventors have discovered that the specific amount of PEG in the lipid compositions according to the present invention is suitable to provide for an effective transfection and delivery, respectively.

In a further aspect the present inventors have surprisingly found that the lipid compositions according to the present invention which are preferably present as lipoplexes or liposomes, preferably show an overall cationic charge and thus an excess of at least one positive charge. More preferably, the lipid compositions exhibit a charge ratio negative: positive of from about 1:1.3 to 1:5. Therefore, the present invention is thus related in a further aspect to any lipid composition comprising at least one cationic lipid and a nucleic acid, preferably a RNAi, siRNA or siNA or any other of the functional nucleic acids defined herein, having a charge ratio negative:positive of from about 1:1.3 to 1:5. The cationic lipid is preferably any cationic lipid described herein. The lipid composition comprises in a preferred embodiment any helper lipid or helper lipid combination as described herein. In a preferred embodiment the composition according to the present invention containing nucleic acid(s) forms lipoplexes. In a preferred embodiment the term lipoplexes as used herein refers to a composition composed of cationic lipid, neutral helper lipid and nucleic acid.

The present inventors have also found that in particular the molar ratio of siRNA and the cationic lipid can be crucial for the successful application of the lipid composition according to the present invention, especially in view of what has been said above in relation to the cationic overall charge of the nucleic acid containing lipid formulations. Without wishing to be bound by any theory it seems that 1 mole of cationic lipid, particularly as disclosed herein, can provide for a maximum of three positive charges per molecule, whereas the nucleic acid and more particularly the siRNA molecules as disclosed herein, provide for a maximum of 40 negative charges per molecule. In order to reach an overall positive charge of the siRNA containing lipid formulations according to the present invention, the molar ratio can range from 0 to a maximum of 0.075. A preferred molar ration range is from about 0.02 to 0.05 and even more preferred is a molar ratio range of about 0.037.

Another surprising finding of the present inventors is that the composition according to the present invention exhibits particularly useful characteristics if the composition contains a nucleic acid, preferably a siRNA molecule or a siNA molecule, and the charge ratio of nucleic acid backbone phosphates to cationic lipid nitrogen atoms is about from 1:1.5-7, more preferably 1:4. The term nucleic acid backbone phosphates as used herein refers to the phosphate moieties of the nucleic acid provided by the individual nucleotide forming such nucleic acid. The term cationic lipid nitrogen atom as used herein refers to those nitrogen atoms provided by the cationic lipid which preferably comprises a total of three positive charges. Said three positive charges are provided by two primary amino groups and the guanidine group. For the purpose of determining the charge provided by the nucleic acid backbone phosphates the following assumptions are made: Each phosphate between two nucleosides provides for one negative charge and 3' terminal phosphate, if present, provides for two negative charges. For the purpose of determining the ratio of the charges provided by the cationic lipid nitrogen atoms and the charges provided by the phosphate atoms it is assumed that the charges are present as described above although it has to be acknowledged that under the particular circumstances observed under in vitro and/or in vivo application the effective charge ratio might be different from the one specified above.

The above defined charge ratio provides for an efficient transfer of the nucleic acid across a phospholipid bilayer membrane such as a cytoplasma membrane.

A further feature of the composition according to the present invention which provides for its delivery characteristics, is its size distribution. Preferably, the size distribution of the composition according to the present invention being present as a dispersion is about 120 nm. The size is preferably determined by Quasi Elastic Light Scattering, as described in more detail in the example part.

The present inventors have surprisingly found that the composition according to the present invention is particularly suitable to deliver nucleic acids, preferably functional nucleic acids such as siRNA and siNA molecules, into cells. As outlined in more detail in the example, the compositions according to the present invention are very active in delivering said nucleic acids into the intracellular space of endothelial cells, epithelial cells and cancer cells. There seems to be an even more increased specificity such that the delivery is particularly active in endothelial cells of vasculature, although other endothelial cells can also be infected using the composition according to the present invention. A particularly effective transfection occurs with endothelial cells of vasculature, more specifically vasculature which is the result of neoangiogenesis as induced by tumors. Other vasculature which might be addressed is the vasculature of kidney, heart, lung, liver and pancreas.

It is to be acknowledged that the composition according to the present invention is also beneficial insofar as it is particularly mild or non-toxic. Such lack of toxicity is clearly advantageous over the compositions of the prior art as it will significantly contribute to the medicinal benefit of any treatment using this kind of composition by avoiding side effects, thus increasing patient compliance and particular forms of administration such as bolus administration. The latter is, as may be taken from the example part herein, evident from animal studies.

It is within the present invention that the composition and more particularly the pharmaceutical composition may comprise one or more of the aforementioned biologically active compounds which may be contained in a composition according to the present invention as a pharmaceutically active compound and as further constituent, respectively. It will be acknowledged by the ones skilled in the art that any of these compounds can, in principle, be used as a pharmaceutically active compound. Such pharmaceutically active compound is typically directed against a target molecule which is involved in the pathomechanism of a disease. Due to the general design principle and mode of action underlying the various biologically active compounds and thus the pharmaceutically active compounds as used in connection with any aspect of the present invention, virtually any target can be addressed. Accordingly, the compound according to the present invention and the respective compositions containing the same can be used for the treatment or prevention of any disease or diseased condition which can be addressed, prevented and/or treated using this kind of biologically active compound. It is to be acknowledged that apart from these biologically active compounds also any other biologically active compound can be part of a composition according to any embodiment of the present invention. Preferably such other biologically active compound comprises at least one negative charge, preferably under conditions where such other biologically active compound is interacting or complexed with the compound according to the present invention, more preferably the compound according to the present invention which is present as a cationic lipid.

As used herein, a biologically active compound is preferably any compound which is biologically active, preferably exhibits any biological, chemical and/or physical effects on a biological system. Such biological system is preferably any biochemical reaction, any cell, preferably any animal cell, more preferably any vertebrate cell and most preferably any mammalian cell, including, but not limited to, any human cell, any tissue, any organ and any organism. Any such organism is preferably selected from the group comprising mice, rats, guinea pigs, rabbits, cats, dogs, monkeys and humans.

It is also within the present invention that any of the compositions according to the present invention, more particularly any pharmaceutical composition according to the present invention may comprise any further pharmaceutically active compound(s).

The composition, particularly the pharmaceutical composition according to the present invention can be used for various forms of administration, whereby local administration and systemic administration are particularly preferred. Even more preferred is a route of administration which is selected from the group comprising intramuscular, percutaneous, subcutaneous, intravenous and pulmonary administration. As preferably used herein, local administration means that the respective composition is administered in close spatial relationship to the cell, tissue and organ, respectively, to which the composition and the biologically active compound, respectively, is to be administered. As used herein, systemic administration means an administration which is different from a local administration and more preferably is the administration into a body fluid such as blood and liquor, respectively, whereby the body liquid transports the composition to the cell, tissue and organ, respectively, to which the composition and the biologically active compound, respectively, is to be delivered.

As used herein, the cell across the cell membrane of which a biologically active compound is to be transferred by means of the compound and composition according to the present invention, respectively, is preferably an eukaryotic cell, more preferably a vertebrate cell and even more preferably a mammalian cell. Most preferably the cell is a human cell.

Any medicament which can be manufactured using the compound and composition according to the present invention, respectively, is for the treatment and prevention of a patient. Preferably such patient is a vertebrate, more preferably a mammal and even more preferably such mammal is selected from the group comprising mice, rats, dogs, cats, guinea pigs, rabbits, monkeys and humans. In a further aspect the compound and composition according to the present invention can be used as a transferring agent, more preferably as a transfection agent.

As preferably used herein a transferring agent is any agent which is suitable to transfer a compound, more preferably a biologically active compound such as a pharmaceutically active compound across a membrane, preferably a cell membrane and more preferably transfer such compound into a cell as previously described herein. Preferably, the cells are endothelial cells, more preferably endothelial cells of vertebrates and most preferred endothelial cells of mammals such as mice, rats, guinea pigs, dogs, cats, monkeys and human beings.

In a still further aspect the present invention is related to a method for transferring, more particularly transfecting, a cell with a biologically active compound. In a first step, whereby the sequence of steps is not necessarily limited, the cell and the membrane and cell, respectively, is provided. In a second step, a compound according to the present invention is provided as well as a biologically active compound such as a pharmaceutically active compound. This reaction can be contacted with the cell and the membrane, respectively, and due to the biophysical characteristics of the compound and the composition according to the present invention, the biologically active compound will be transferred from one side of the membrane to the other one, or in case the membrane forms a cell, from outside the cell to within the cell. It is within the present invention that prior to contacting the cell and the membrane, respectively, the biologically active compound and the compound according to the present invention, i.e. the cationic lipid, are contacted, whereupon preferably a complex is formed and such complex is contacted with the cell and the membrane, respectively.

In a further aspect of the present invention the method for transferring a biologically active compound and a pharmaceutically active compound, respectively, comprises the steps of providing the cell and the membrane, respectively, providing a composition according to the present invention and contacting both the composition and the cell and the membrane, respectively. It is within the present invention that the composition may be formed prior or during the contacting with the cell and the membrane, respectively.

In an embodiment of any method for transferring a biologically active compound as disclosed herein, the method may comprise further steps, preferably the step of detecting whether the biologically active compound has been transferred. Such detection reaction strongly depends on the kind of biologically active compounds transferred according to the method and will be readily obvious for the ones skilled in the art. It is within the present invention that such method is performed on any cell, tissue, organ and organism as described herein.

The present invention is further illustrated by reference to the following figures and examples from which further features, embodiments and advantages of the present invention may be taken. More particularly, FIG. 1 shows the basic design of the cationic lipid according to the present invention;

FIG. 2 shows the synthesis of N-oleyl-palmitylamine which is a possible starting material for the synthesis of the compounds according to the present invention, whereby such synthesis is the one according to the prior art as described in U.S. Pat. No. 6,395,713;

FIG. 20A depicts the result of a Western blot analysis for determining potent siRNA molecules for efficacious CD31 knock-down;

FIG. 20B is a diagram illustrating the effect of anti-CD31 siRNA on CD31 mRNA levels in different organs of mice;

FIG. 20C shows the result of a Western blot analysis for determining the efficacy of CD31 protein knock-down in different organs of mice using anti CD31 siRNA molecules;

FIG. 21A depicts the result of a Western blot analysis studying the efficacy of anti-CD31 siRNA and anti-PTEN siRNA molecules on CD31, CD34, PTEN and p-Akt knock-down;

FIG. 21B is a diagram illustrating the effect of different patterns of lipoplex administration on body weight of test animals as a function of time;

FIG. 21C represents diagrams illustrating the effect of different anti-CD31 siRNA treatment regimens on the volume of two different tumor xenografts; and FIG. 21D is a diagram illustrating the inhibition of growth of established PC-3 xenografts under an anti-CD31 treatment regimen.

EXAMPLE 1

Synthesis of N-Oleyl-Palmityl Amine According to the Prior Art

Figure 1:
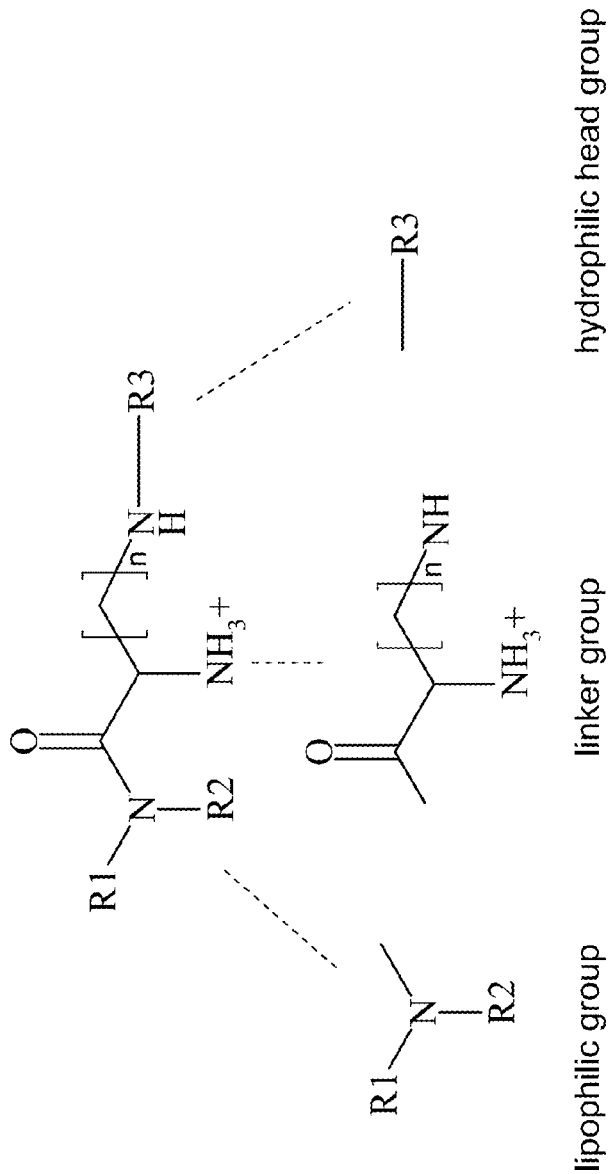
Figure 2:
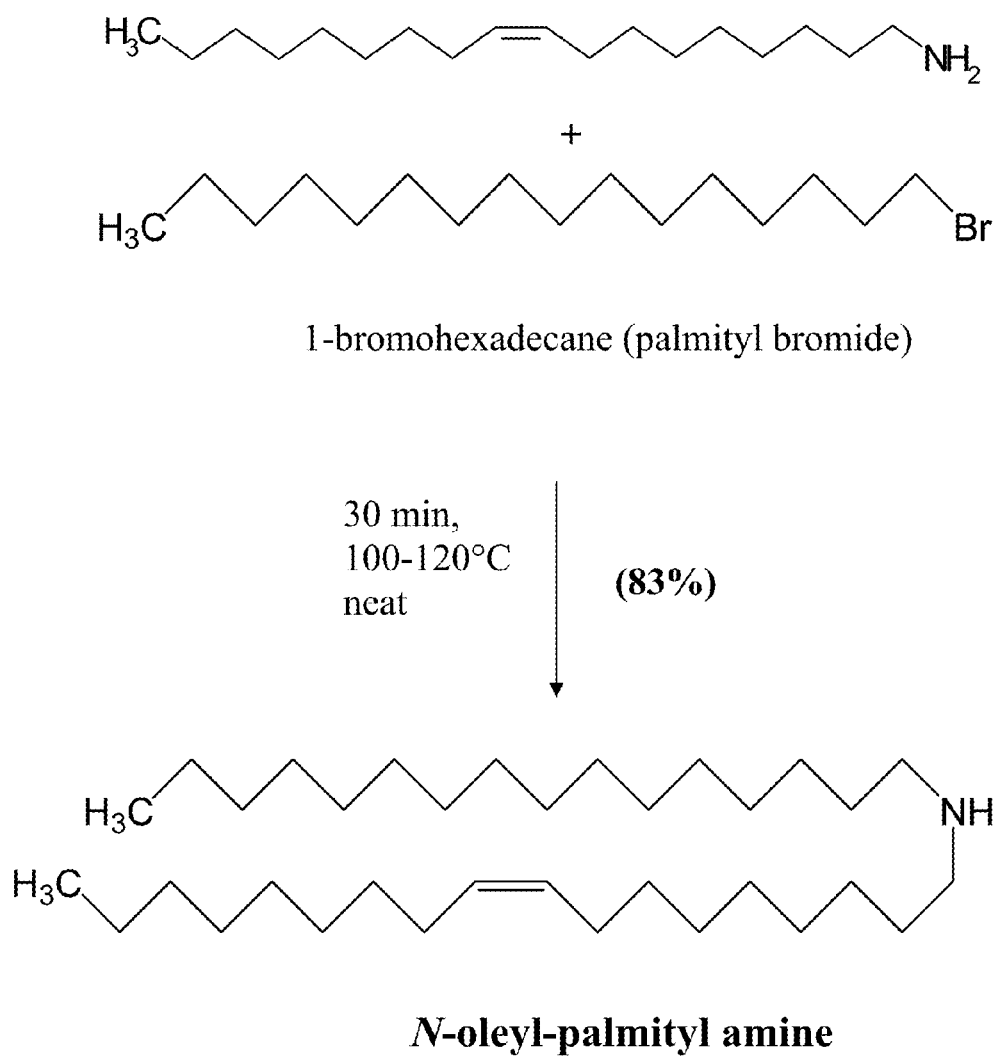

N-oleyl-palmityl amine is an important starting material for the compounds according to the present invention. The N-oleyl-palmityl amine can, in principle, be synthesised as described in U.S. Pat. No. 6,395,713. The respective reaction scheme is depicted in FIG. 2. However, the starting material is oleyl amine of technical grade as provided by, e. g., Fluka. An analysis of this starting material by gas chromatography shows a purity of ≥70%, whereby 30% of the material consists of amine having different chain lengths. The reason for this could be that the material as such is obtained from plant sources. Combining both oleyl amine and 1-bromohexadecane (palmitylbromid) yields N-oleyl-palmityl amine after reacting both starting materials at 100 to 120° C. for 30 minutes. The yield is about 83%.

EXAMPLE 2

Synthesis of N-Palmityl-Oleyl Amine According to the Present Invention

Figure 3:
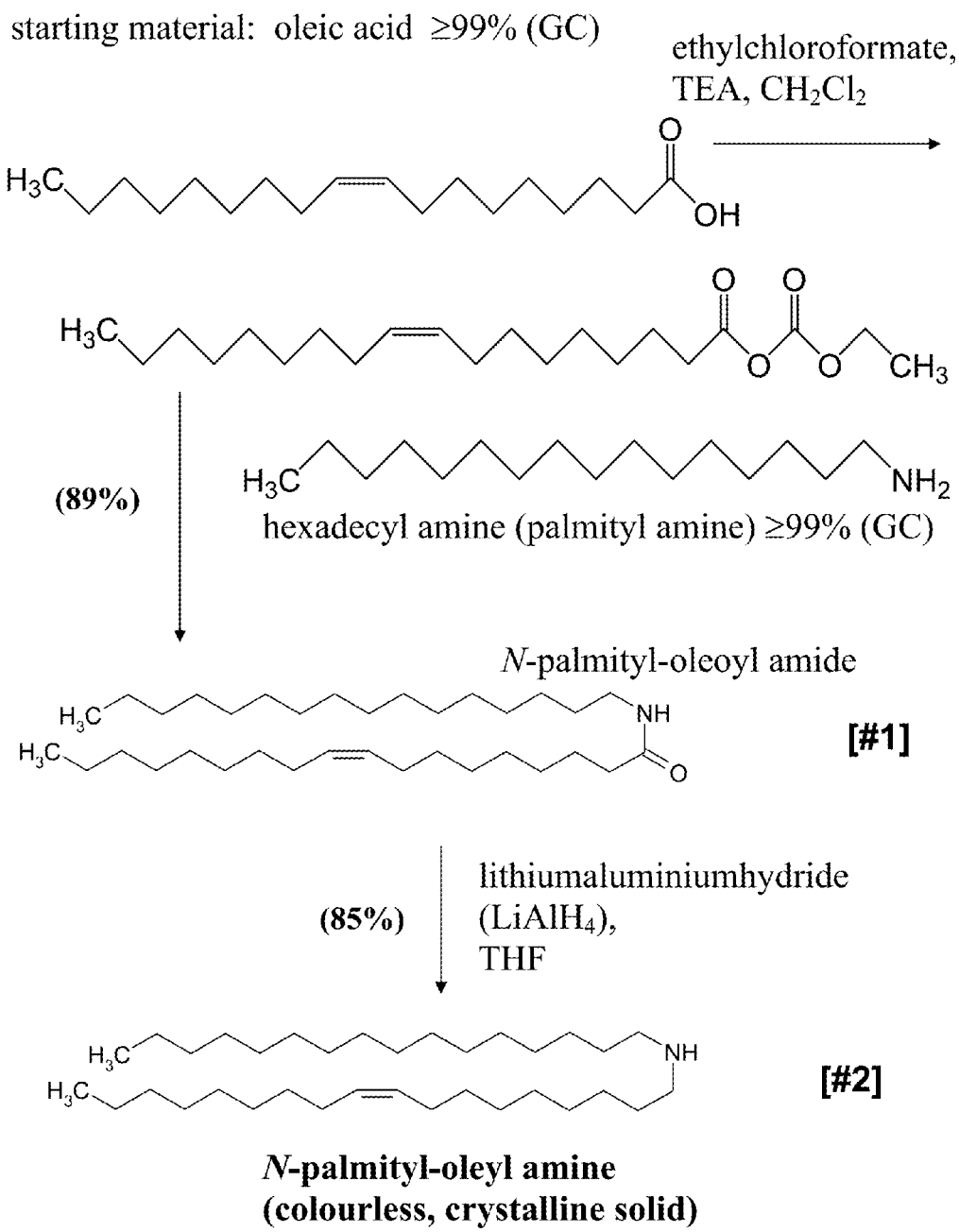
FIG. 3 depicts the synthesis of N-oleyl-palmitylamine which is an important starting material according to the present invention.

A new synthesis has been perceived by the present inventor in connection with the compounds according to the present invention (FIG. 3). This new reaction scheme is based on the finding of the present inventor that the high amount of impurities is affecting the quality of the transferring agent prepared based on this starting material. Accordingly, the reaction starts using oleic acid having a purity of 99% as shown by gas chromatography and contacting such oleic acid with ethylchloroformate, TEA and $CH_2Cl_2$ and reacting the thus obtained mixed carboxylic-carbonic anhydride with hexadecylamine (palmitylamine) having again a purity of 99% as shown by gas chromatography. The reaction product N-palmityl-oleoyl amide [#1] is subsequently reacted with $LiAlH_4$ (in THF) resulting in 85% N-palmityl-oleyl amine [#2] which is present as a colourless crystalline solid.

The more detailed reaction conditions are outlined in the following.

Synthesis of N-palmityl-oleoyl amide [#1]

2.62 ml (27.5 mmol) chloroformic acid ethyl ester are dissolved in 30 ml anhydrous dichloromethane in a 250 ml nitrogen flask according to Schlenk under argon inert gas and cooled to 0° C. A solution of 7.93 ml (25 mmol) oleic acid and 4.16 ml (30 mmol) triethylamine in 40 ml anhydrous dichloromethane are added dropwise under stirring within 20 minutes. After stirring on the ice bath for 30 minutes a solution of 6.64 g (27.5 mmol) palmitylamine in 50 ml $CHCl_3$ is rapidly added dropwise and the mixture is stirred at room temperature for 2 hours. Subsequently, the solution is washed three times with 40 ml water each, the organic phase dried over $Na_2SO_4$ and the solvent removed using a rotary evaporator. The residue is re-crystallised from 100 ml acetone. 11.25 g (22.3 mmol) corresponding to a yield of 89% of a colourless solid is obtained.

Synthesis of N-palmityl-oleylamine [#2]

20 ml 1M LiAlH$_4$ in ether are provided under argon inert gas in a 250 ml three-neck flask having a dropping funnel and a reflux condenser and subsequently a solution of 7.59 g (15 mmol) palmityloleoylamide in 80 ml THF added dropwise within 20 minutes. The mixture is refluxed for 2.5 hours, then another 5 ml 1 M LiAlH$_4$ in ether is added and refluxed for another 2.5 hours. Excess hydride is decomposed using 6 M NaOH under ice bath cooling and the precipitate is filtered off. The precipitate is extracted twice with 40 ml of hot MtBE each, the combined organic phases dried over Na$_2$SO$_4$ and the solvent removed using a rotary evaporator. The residue is crystallised from 100 ml MtBE at −20° C. 6.23 g (12.7 mmol) corresponding to a yield of 85% of a colourless crystalline solid are obtained.

EXAMPLE 3

Synthesis of Boc-Dap(Fmoc)-N-Plamityl-N-Oleyl-Amide [#3]

Figure 4:
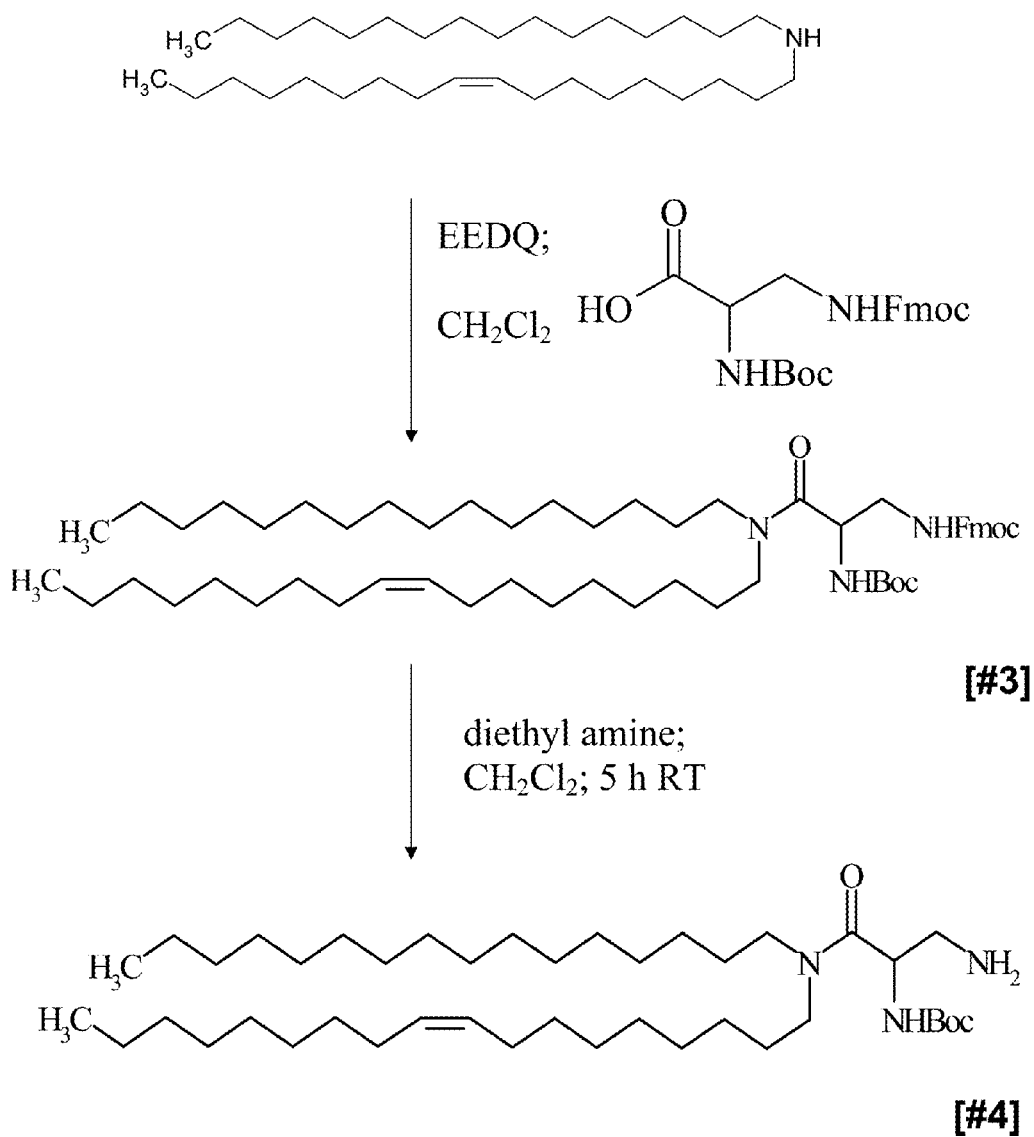
FIGS. 4-9 depict the synthesis of β-arginyl-2,3-amino propionic acid-N-palmityl-N-oleyl-amide trihyrdochloride, β-arginyl-2,3-diamino propionic acid-N-lauryl-N-myristyl-amide trihydrochloride and ε-arginyl-lysine-N-lauryl-N-myristyl-amide trihydrochloride.

521 mg (1.06 mmol) N-oleyl-palmitylamine in 10 ml anhydrous dichloromethane are dissolved in a 50 ml round-bottom flask and 289 mg (1.17 mmol) EEDQ are added. Subsequently, 500 mg (1.17 mmol) Boc-Dap(Fmoc)-OH are added under stirring and the mixture is stirred at room temperature for 20 hours. The solution is transferred with 80 ml dichloromethane into a separating funnel and washed three times with 20 ml 0.1 N HCl each and once with 20 ml saturated NaHCO$_3$ solution. After drying over Na$_2$SO$_4$ the solvent is removed using a rotary evaporator (FIG. 4). A yellowish viscous oil is obtained which is not further purified. In thin layer chromatography using hexane/ethylacetate of 1:1 a $R_f$ of 0.70 was observed.

EXAMPLE 4

Synthesis of Boc-Dap-N-Palmityl-N-Oleyl-Amide [#4]

1 g Boc-Dap(Fmoc)-N-palmityl-N-oleyl-amide raw product was dissolved in 8 ml anhydrous dichloromethane in a 50 ml round-bottom flask. 3 ml diethylamine was added and stirred at room temperature (FIG. 4). Thin layer chromatography control of the reaction showed that after 4.5 hours the reaction of the starting product was completed. The volatile components were removed by a rotary evaporator and the residue is chromatography purified using 40 g silica gel 60 (Merck) using hexane/ethylacetate 5:1. The product was eluted using a step gradient consisting of ethylacetate, ethylacetate/methanol 4:1 and dichloromethane/methanol 4:1. 576 mg (0.85 mmol) Boc-Dap-N-palmityl-N-oleyl-amide were obtained as a yellow viscous oil.

EXAMPLE 5

Synthesis of Tetra-Boc-M-Arginyl-[2,3-Diaminopropionic Acid-N-Palmityl-N-Oleyl-Amide] [#5]

Figure 5:
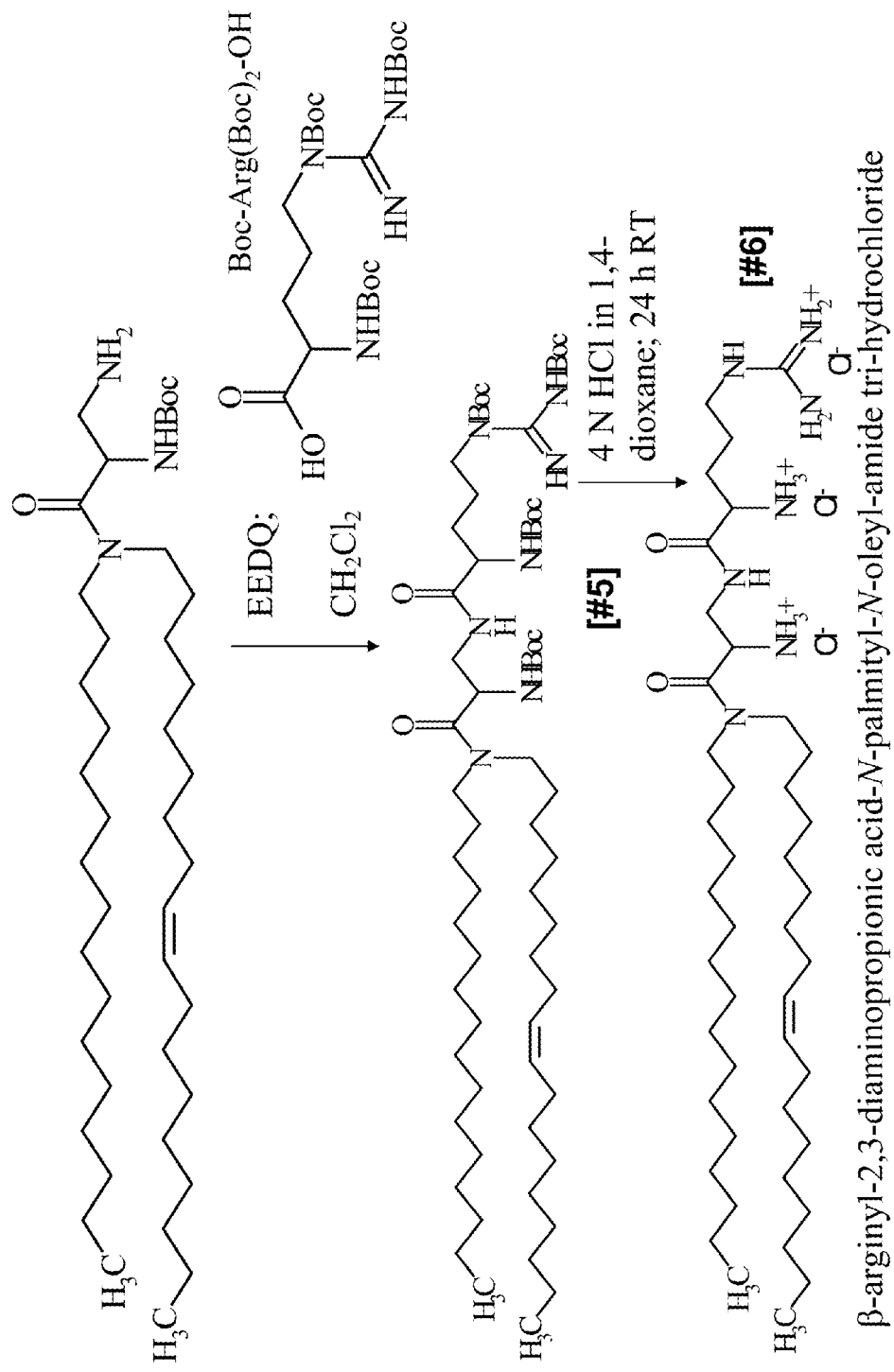

576 mg (0.85 mmol) Boc-Dap-N-palmityl-N-oleyl-amide were dissolved in 10 ml anhydrous dichloromethane in a 100 ml round-bottom flask and 210 mg (0.85 mmol) EEDQ and 403 mg (0.85 mmol) Boc-Arg(Boc)$_2$-OH were added under stirring (FIG. 5). The mixture was stirred under argon atmosphere at room temperature for 20 hours. Subsequently, the dichloromethane is removed by a rotary evaporator and the residue in 100 ml MtBE transferred into a separating funnel. The organic phase was thoroughly washed with 0.1 N HCl, 1 N NaOH and saturated NaHCO$_3$ solution, dried over Na$_2$SO$_4$ and the solvent removed by a rotary evaporator. The raw product was subsequently purified by flash chromatography (Combiflash Retrieve; Isco Inc.) using hexane/ethylacetate as eluent. 694 mg (0.61 mmol) corresponding to a yield of 72% of a colourless viscous oil was obtained.

EXAMPLE 6

Synthesis of β-Arginyl-2,3-Diaminopropionic Acid-N-Palmityl-N-Oleyl-Amide Trihydrochloride [#6]

694 mg (0.61 mmol) well dried tetra-Boc-[β-arginyl-2,3-diaminopropionic acid-N-palmityl-N-oleyl-amide] were provided under argon atmosphere in a 25 ml nitrogen flask according to Schlenk and 8 ml 4N HCl in dioxane added (FIG. 5). The mixture was stirred under argon inert gas at room temperature for 24 hours, whereby product precipitated as amorphous and partially as wax-like solid from the solution after about 6 to 8 hours. After completion of the reaction (thin layer control using CHCl$_3$/MeOH/NH$_4$OH 65:25:4) any volatile components were removed under high vacuum. 489 mg (0.58 mmol) β-arginyl-2,3-diaminopropionic acid-N-pamityl-N-oleyl-amide were obtained as trihydrochloride.

EXAMPLE 7

Synthesis of N-Lauryl-Myristyl Amine [#7]

Figure 6:
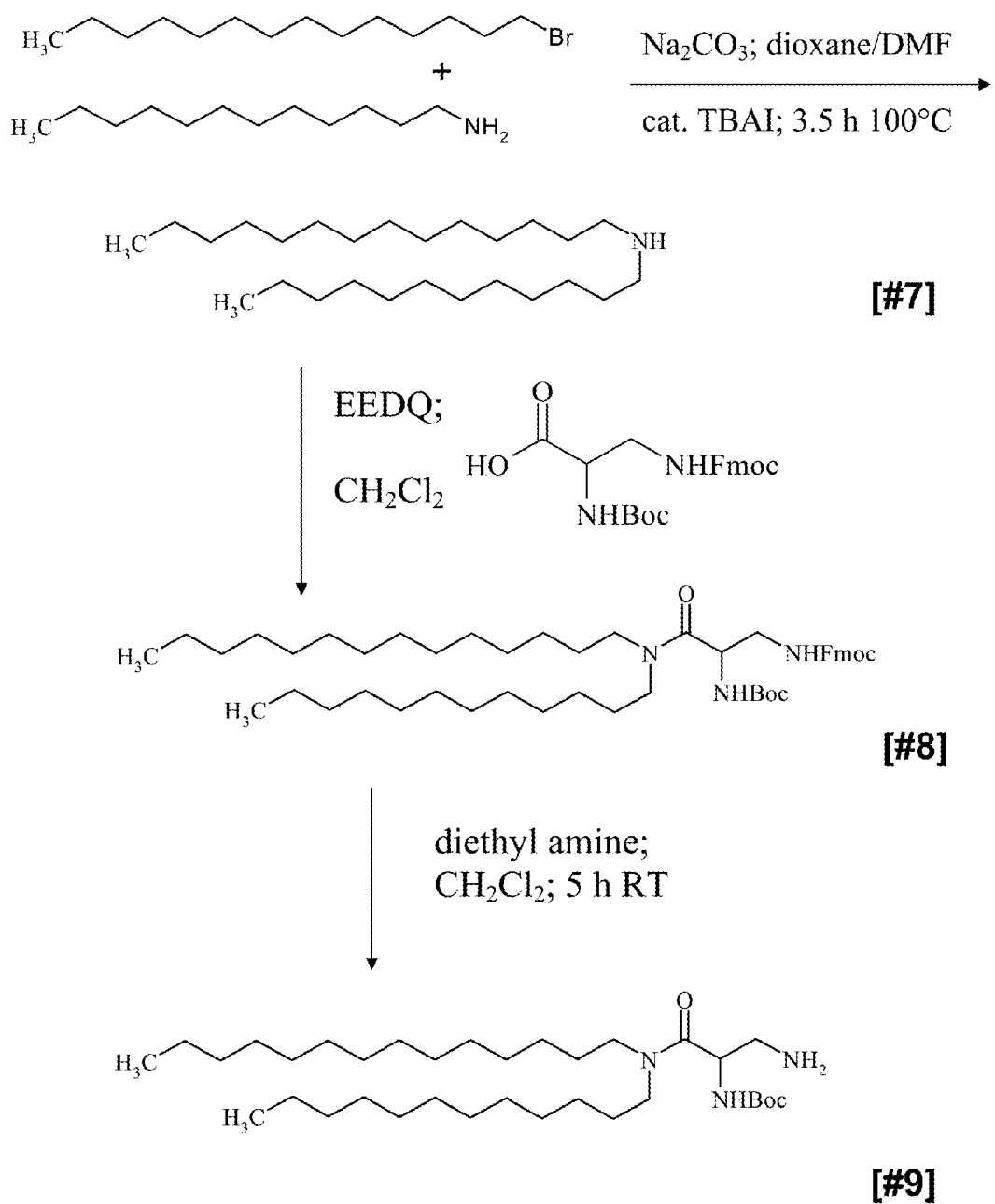

18.54 g (100 mmol) dodecylamine (laurylamine), 6.36 g (60 mmol) Na$_2$CO$_3$ and 50 mg tetrabutyl ammonium iodide (TBAI) were suspended in 100 ml anhydrous DMF in a 500 ml 3-neck flask having a reflux condenser and a dropping funnel. A solution of 16.4 ml (60 mmol) 1-bromo tetradecane in 100 ml anhydrous dioxane were added dropwise at 100° C. over a period of 110 minutes and the mixture was stirred for another 3.5 hours at 100° C. (FIG. 6). The solution was filtered at a temperature as hot as possible. The crystalline solid which precipitated at 4° C. overnight, was removed and was washed with a little of cold methanol. Subsequently, the solid was re-crystallised from 200 ml methanol. 9 g of colourless leaf-like crystals were obtained which are re-crystallised from 100 ml MtBE. The crystals which precipitated at −18° C., were sucked off from a cooled frit and washed with cold MtBE. 7.94 g (21 mmol) of a colourless crystalline solid were obtained, corresponding to a yield of 35%.

EXAMPLE 8

Synthesis of Boc-Dap(Fmoc)-N-Lauryl-N-Myristyl Amide [#8]

715 mg (1.68 mmol) Boc-Dap(Fmoc)-OH were dissolved in 15 ml anhydrous dichloromethane in a 50 ml round-bottom flask and 420 mg (1.7 mmol) EEDQ were added. The mixture was stirred at room temperature for 45 minutes and subsequently a solution of 641 mg (1.68 mmol) N-laurylmyristyl amine in 25 ml anhydrous dichloromethane was slowly added dropwise within 60 minutes (FIG. 6). After a reaction time of 20 hours the solvent was removed by a rotary evaporator and the residue transferred with 100 ml MtBE into a separating funnel. The solution was thoroughly washed with 0.1 N HCl and saturated NaHCO$_3$ solution, the organic phase dried over Na$_2$SO$_4$ and the solvent removed by a rotary evaporator. 1.02 g of a raw product were obtained which was purified by flash chromatography (Combiflash Retrieve; Isco Inc.) using hexane/ethylacetate as eluent. 607 mg pure product was obtained as colourless, very viscous oil. Thin layer chromatography using hexane/ethylacetate 1:1 provided a R$_f$ of 0.58.

EXAMPLE 9

Synthesis of Boc-Dap-N-Lauryl-N-Myristyl Amide [#9]

607 mg Boc-Dap(Fmoc)-N-lauryl-N-myristyl amide were dissolved in 8 ml anhydrous dichloromethane in a 50 ml round-bottom flask (FIG. 6). 3 ml diethylamine were added and the reaction stirred at room temperature for 4.5 hours. The volatile constituents were removed using a rotary evaporator and the residue was purified by chromatography using 40 g silica gel 60 (Merck) with hexane/ethylacetate 5:1. The product was eluted by a step gradient consisting of ethylacetate, dichloromethane and dichloromethane/methanol 3:1. 372 mg (0.655 mmol) Boc-Dap-N-lauryl-N-myristyl amide was obtained as yellowish, viscous oil.

EXAMPLE 10

Synthesis of Tetra-Boc-[β-Arginyl-2,3-Diaminopropionic Acid-N-Lauryl-N-Myristyl Amide] [#10]

Figure 7:
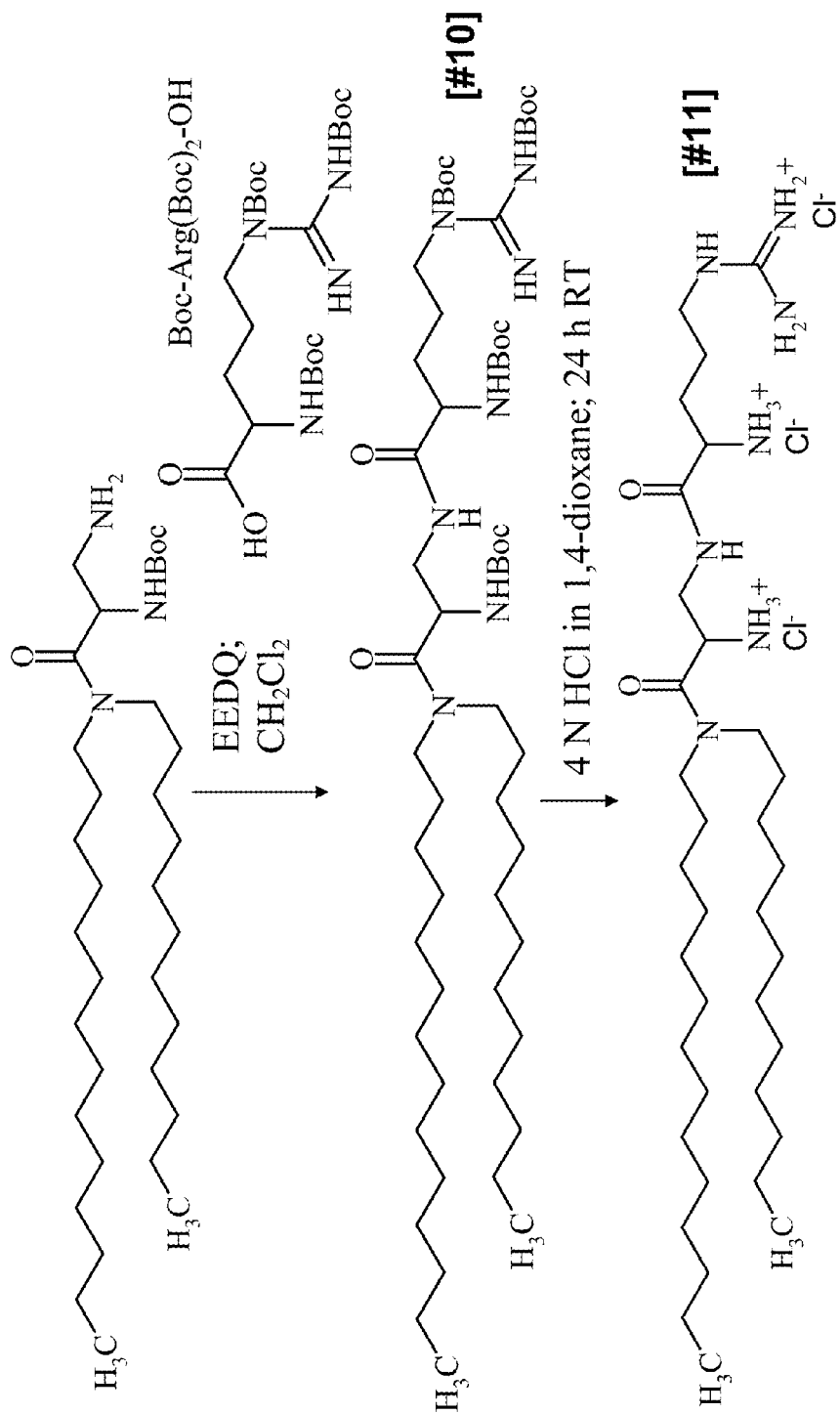

372 mg (0.655 mmol) Boc-Dap-N-lauryl-N-myristyl amide were dissolved in 8 ml anhydrous dichloromethane in a 50 ml round-bottom flask and 162 mg (0.655 mmol) EEDQ and 311 mg (0.655 mmol) Boc-Arg-(Boc)$_2$-OH were added under stirring (FIG. 7). The mixture was stirred at room temperature for 20 hours. Subsequently, the dichloromethane was removed using a rotary evaporator and the residue was transferred with 80 ml MtBE into a separating funnel. The organic phase was thoroughly washed with 0.1 N HCl, 1 N NaOH and saturated NaHCO$_3$ solution, dried over Na$_2$SO$_4$ and the solvent removed by a rotary evaporator. The raw product was subsequently purified by flash chromatography (Combiflash Retrieve; Isco Inc.) using a step gradient of hexane/ethylacetate. 500 mg (0.5 mmol) of a colourless viscous oil were obtained, corresponding to a yield of 76%.

EXAMPLE 11

Synthesis of β-Arginyl-2,3-Diaminopropionic Acid-N-Lauryl-N-Myristyl Amide Trihydrochloride [#11]

511 mg (0.5 mmol) well dried tetra-Boc-[β-arginyl-2,3-diaminopropionic acid-N-lauryl-N-myristyl amide] were provided under argon in a 25 ml argon flask according to Schlenk and 10 ml 4 N HCl in dioxane were added (FIG. 7). The mixture was stirred under argon inert gas at room temperature for 24 hours, whereby product precipitated as partially amorphous, partially wax-like solid from the solution after 6 to 8 hours. Upon completion of the reaction (thin layer chromatography control using CHCl$_3$/MeOH/NH$_4$OH 65:25:4) all volatile components were removed under high vacuum. 323 mg (0.5 mmol) β-arginyl-2,3-diaminopropionic acid-N-lauryl-N-myristyl amide in the form of the tri-hydrochloride were obtained.

EXAMPLE 12

Synthesis of Boc-Lys(Fmoc)-N-Lauryl-N-Myristyl Amide [#12]

Figure 8:
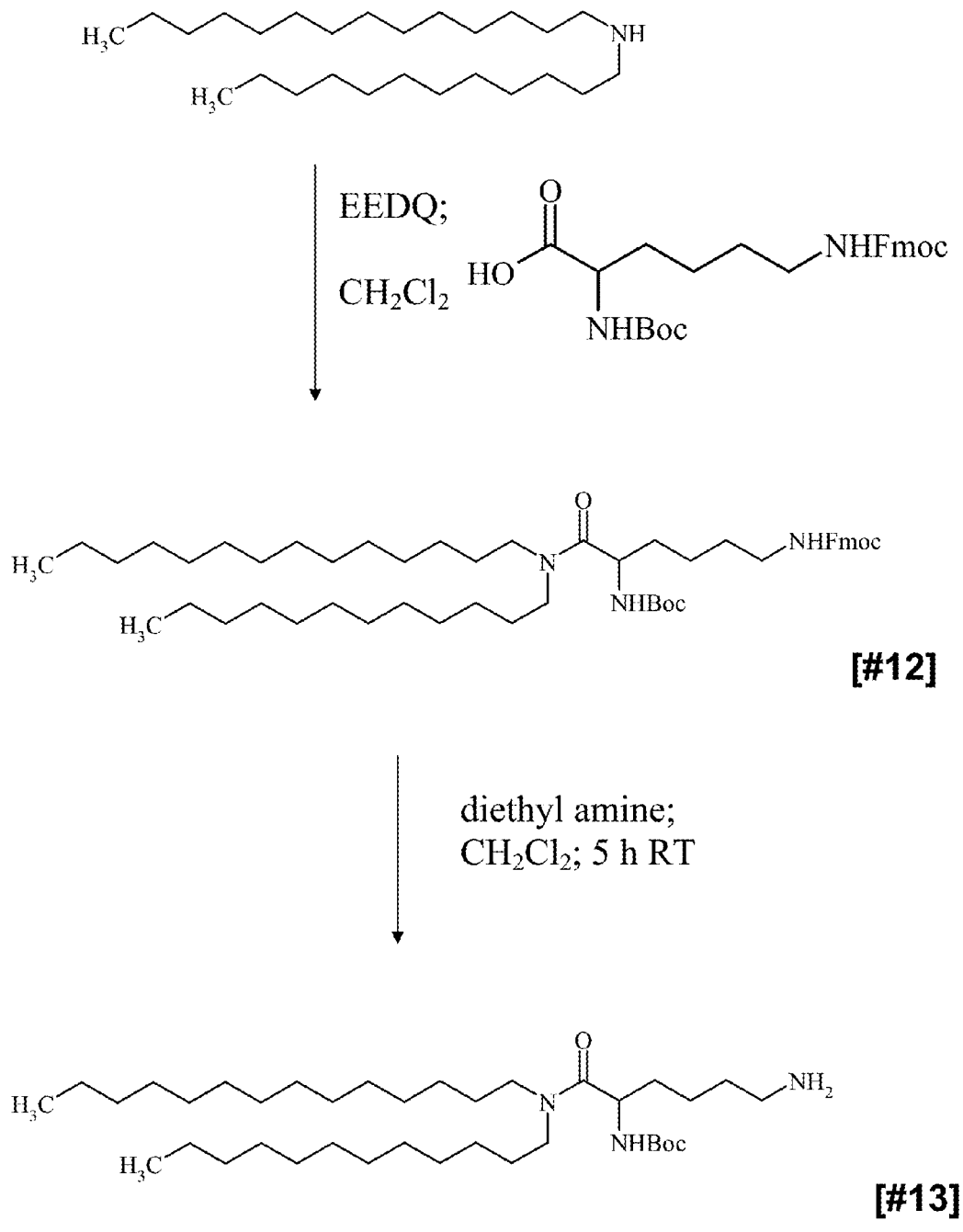

937 mg (2 mmol) Boc-Lys(Fmoc)-OH were dissolved in 10 ml anhydrous dichloromethane in a 50 ml round-bottom flask and 495 mg (2 mmol) EEDQ were added (FIG. 8). The mixture was stirred at room temperature for 60 minutes and subsequently a solution of 764 mg (2 mmol) N-lauryl-myristyl amine in 30 ml anhydrous dichloromethane was slowly added in a dropwise manner within 120 minutes. After a reaction time of 20 hours the solvent was removed using a rotary evaporator and the residue transferred with 100 ml MtBE into a separating funnel. The solution was thoroughly washed with 0.1 N HCl and saturated NaHCO$_3$, the organic phase dried over Na$_2$SO$_4$ and the solvent removed using a rotary evaporator. 1.757 g of a raw product was obtained which was purified using flash chromatography with hexane/ethylacetate 4:1 as eluent. 1.377 g pure product is obtained as colourless, very viscous oil. Thin layer chromatography using hexane/ethylacetate 1:1 gave a R$_f$ of 0.57.

EXAMPLE 13

Synthesis of Boc-Lys-N-Lauryl-N-Myristyl Amide [#13]

1.377 g Boc-Lys(Fmoc)-N-lauryl-N-myristyl-amide were dissolved in 16 ml anhydrous dichloromethane in a 50 ml round-bottom flask. 6 ml diethylamine were added and the mixture was stirred at room temperature for 5 hours (FIG. 8). The volatile components were removed using a rotary evaporator and the residue was purified by chromatography using 40 g silica gel 60 (Merck) with hexane/ethylacetate 5:1. The product was eluted using a step gradient consisting of ethylacetate, dichloromethane and dichloromethane/methanol 3:1. 556 mg (0.911 mmol) Boc-Lys-N-lauryl-N-myristyl amide was obtained as yellowish viscous oil as well as 119 mg of a mixed fraction.

EXAMPLE 14

Synthesis of Tetra-Boc-[ε-Arginyl-Lysine-N-Lauryl-N-Myristyl Amide] [#14]

Figure 9:
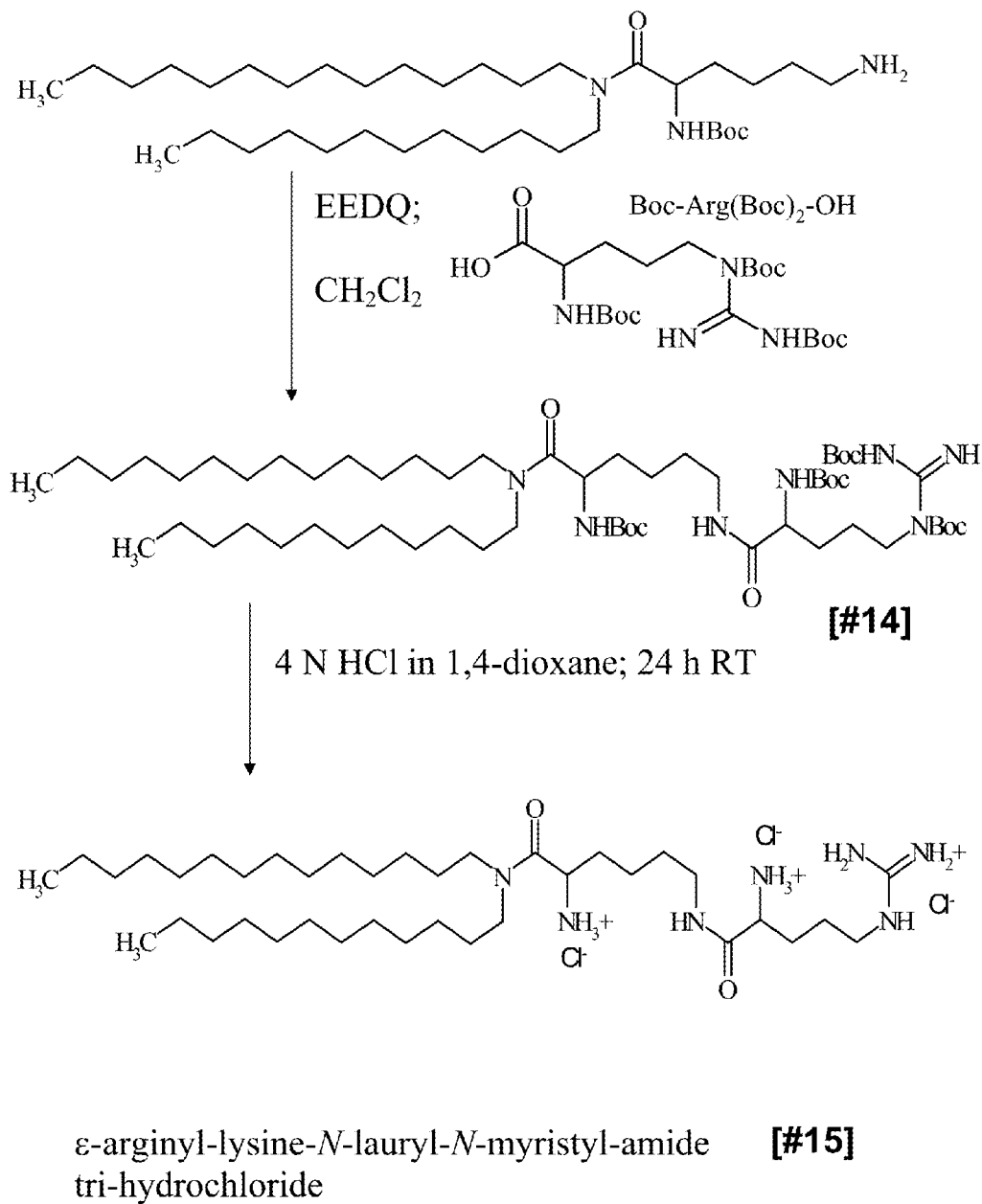

556 mg (0.911 mmol) Boc-Lys-N-lauryl-N-myristyl-amide were dissolved in 40 ml anhydrous dichloromethane and 226 mg (0.911 mmol) EEDQ and 433 mg (0.911 mmol) Boc-Arg(Boc)$_2$-OH were added under stirring (FIG. 9). The mixture was stirred at room temperature for 20 hours. Subsequently, the dichloromethane was removed using a rotary evaporator and the residue was transferred with 80 ml MtBE into a separating funnel. The organic phase was thoroughly washed with 0.1 N HCl and saturated NaHCO$_3$ solution, dried over Na$_2$SO$_4$ and the solvent removed using a rotary evaporator. The raw product was subsequently purified by flash chromatography (Combiflash Retrieve; Isco Inc.) using a hexane/ethylacetate step gradient. A colourless, viscous oil was obtained with a yield of 730 mg (0.684 mmol) corresponding to 75%.

EXAMPLE 15

Synthesis of β-Arginyl-Lysine-N-Lauryl-N-Myristyl Amide Trihydrochloride [#15]

730 mg (0.684 mmol) well dried tetra-Boc-[β-arginyl-lysin-N-lauryl-N-myristyl amide] were provided under argon in a 25 ml argon flask according to Schlenk and 10 ml 4 N HCl in dioxane were added (FIG. 9). The mixture was stirred under argon inert gas at room temperature for 24 hours, whereupon product precipitated from the solution as an amorphous, partially wax-like solid after about 8 hours. Upon completion of the reaction such as controlled by thin layer chromatography using $CHCl_3$/MeOH/$NH_4OH$ 65:25:4, all volatile components were removed under high vacuum. 491 mg (0.633 mmol) ε-arginyl-lysin-N-lauryl-N-myristyl amide were obtained as trihydrochloride.

EXAMPLE 16

Synthesis of Tri-Boc-γ-Carbamidino-α,γ-Diamino Butyric Acid [#16]

Figure 10:
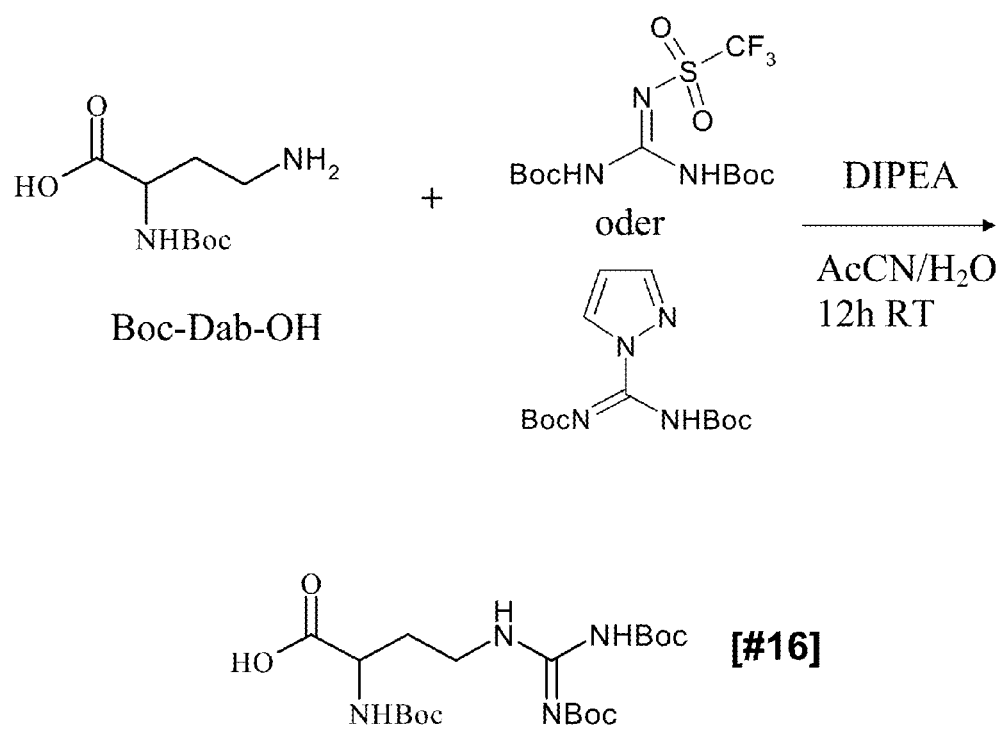
FIG. 10 depicts the synthesis of an alternate cationic head group which is an alternative component for the synthesis of the cationic lipids according to the present invention.
Figure 11:
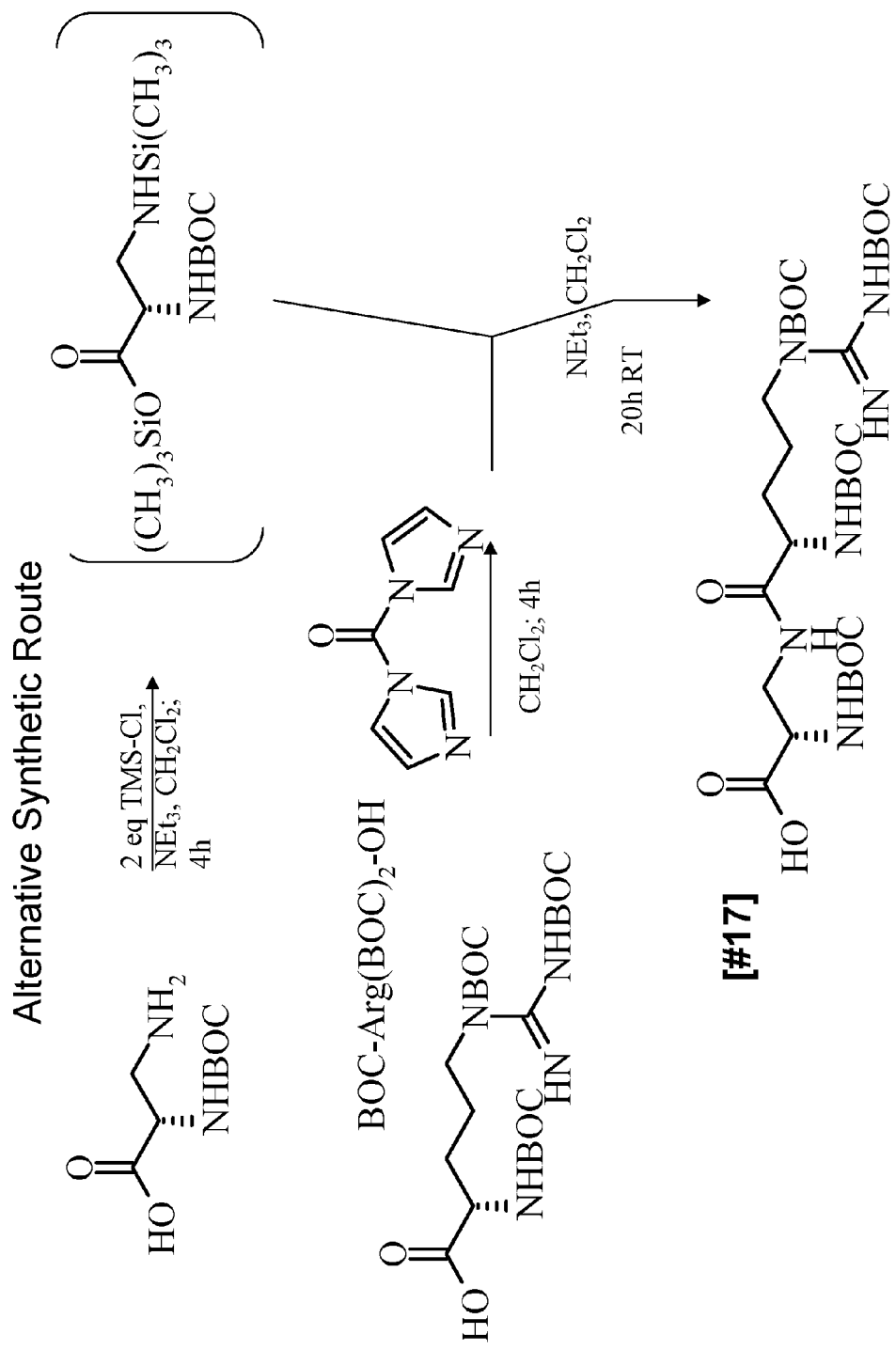
FIG. 11 depicts an alternative synthetic route for the synthesis of beta-arginyl-2,3-diaminopropionic acid-N-palmityl-N-oleyl-amide trihydrochloride.
Figure 11:
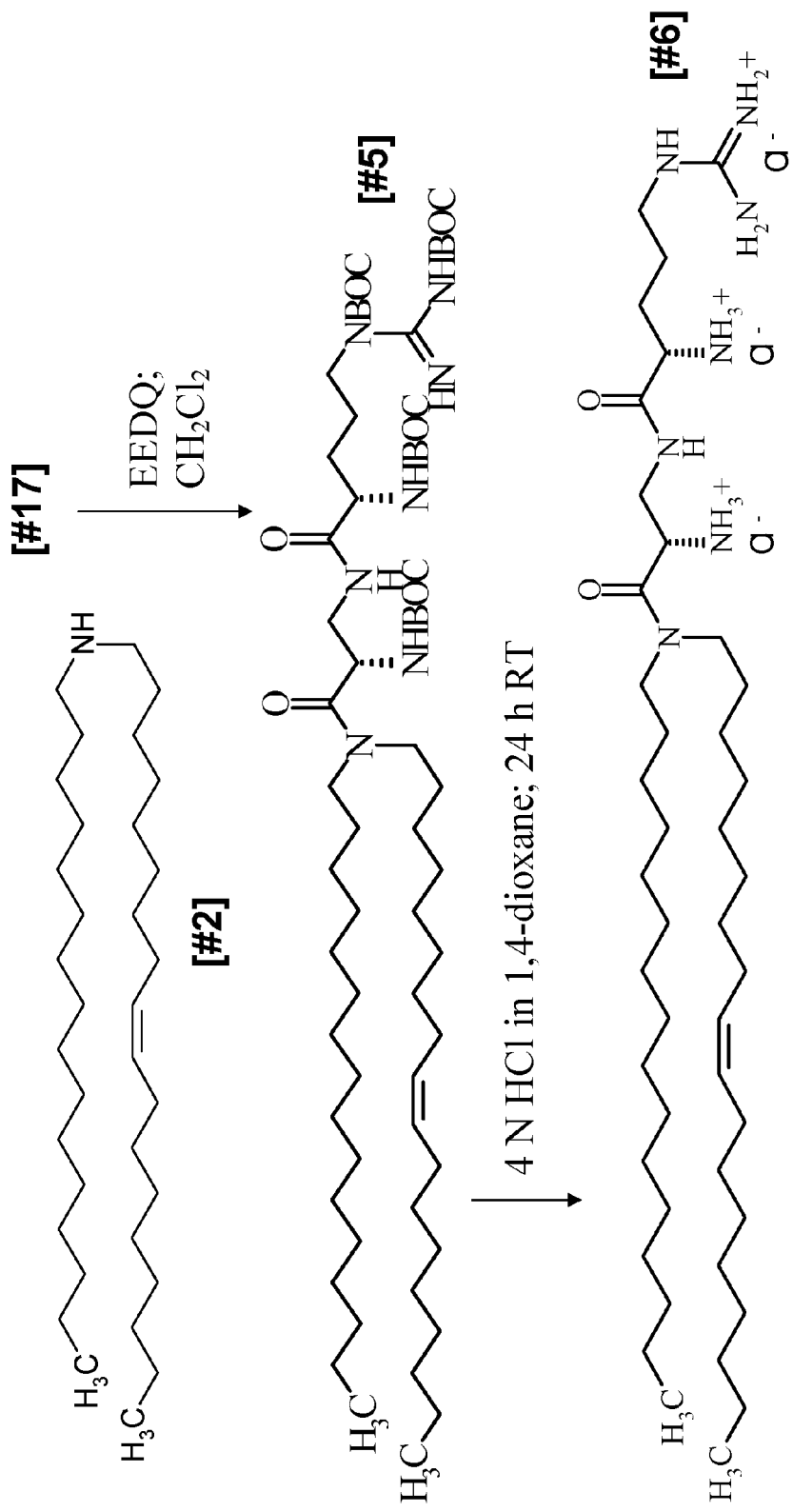

1.31 g (6 mmol) Boc-Dab-OH was provided in 15 ml acetonitrile in a 100 ml round-bottom flask and 12 mmol diisopropylethyl amine (DIPEA) were added (FIG. 10). Subsequently water was added dropwise until a part of the Boc-Dab-OH dissolved and subsequently 1.96 g (5 mmol) 1,3-di-Boc-2-(trifluoromethylsulfonyl)guanidine were added. The mixture was stirred at room temperature for 12 hours, whereupon the acetonitrile was removed using a rotary evaporator. The aqueous residue was diluted with 5 ml water and 50 ml dichloromethane were added. The reaction is acidified to a pH 2 by adding 2 N HCl under stirring and subsequent separation of the organic phase. The aqueous phase was extracted with 50 ml dichloromethane and the combined organic phases were subsequently washed with some of diluted HCl and saturated NaCl solution. The organic phase was dried over $Na_2SO_4$ and the solvent was removed using a rotary evaporator. The residue was purified using chromatography on silica gel 60 using hexane/ethyl-acetate 2:1. 1.138 g (2.47 mmol), corresponding to a yield of 50%, of a colourless amorphous solid was obtained.

EXAMPLE 17

Synthesis of Beta-Arginyl-2,3-Diaminopropionic Acid-N-Palmityl-N-Oleyl-Amide Trihydrochloride [#6]

1.225 g (6 mmole) Boc-Dap-OH in 15 ml absolute $CH_2CL_2$ are suspended in a 250 ml Schlenk flask comprising a dropping funnel under an argon atmosphere and 1.72 ml trimethylamine are added. A solution of 1.52 ml (12 mmole) TMSCI in 30 ml absolute $CH_2CL_2$ is added dropwise within 15 to 20 minutes at room temperature under vigorous stirring. In the meantime 941 mg (5.8 mmole) carbonyl diimidazole is dissolved in 8 ml absolute $CH_2CL_2$ in a 100 ml Schlenk flask under argon atmosphere. A solution of 2.66 g (5.6 mmole) Boc-Arg(Boc)2-OH in 25 ml absolute $CH_2CL_2$ is added dropwise within 15 to 20 minutes at room temperature and under stirring. Both reaction solutions are stirred at room temperature for 4 h. Subsequently, 832 µl (6 mmole) triethyl amine are added to the first solution and the second solution is added dropwise within 15 to 20 minutes through the dropping funnel at room temperature under argon atmosphere. After 15 to 20 minutes 30 ml water are added, vigorously stirred for 45 minutes and the solution is adjusted to a pH of 2. The organic phase is separated and the aqueous phase extracted several times with $CH_2CL_2$. The combined organic phases are dried with a saturated solution of NaCl and sodium sulfate and the solvent removed using a rotary evaporator. The glass-like residue is purified using flash chromatography on silica gel using dichloromethane as eluent. 2.74 g (4.15 mmole; 74%) of a colourless, amorphous solid is obtained [compound 17].

This solid is reacted with oleyl palmityl amine [#2] under conditions which are essentially analogous to the one of Example 10, whereby the temperature is set to 35 to 40° C. (yield 72%). The intended final product β-arginyl-2,3-diaminopropionic acid-N-palmityl-N-oleyl-amide trihydrochloride [#6] is obtained upon cleaving off the Boc protection groups as described in Example 11. The thus obtained product can be further purified using flash chromatography on RP-18 silica gel using MeOH/water as eluent.

EXAMPLE 18

Manufacture of Complexes Consisting of Cationic Liposomes and siRNA (Lipoplexes)

Lipoplexes consisting of cationic liposomes and siRNA were manufactured using standard technologies known in the art such as lipid film/cake rehydration, ethanol injection procedure, reversed phase evaporation or detergent dialysis procedure [c.f. Liposomes as Tools in Basic Research and Industry; Jean R. Philippot and Francis Schuber; CRC Press January 1995 and Liposome Technology: Preparation of Liposomes:001 Gregory Gregoriadis CRC Press I Llc. April 1984].

The thus obtained liposomes which are also referred to herein as lipoplexes in combination with nucleic acids such as siRNA comprise as the lipid β-arginyl-2,3-diaminopropionic acid-N-palmityl-N-oleyl-amide trihydrochloride and additionally either 1,2-diphytanoyl-sn-glycero-3-phosphoethanolamine or 1,2-dioleyl-sn-glycero-3-phosphoethanolamine, whereby the use of 1,2-diphytanoyl-sn-glycero-3-phosphoethanolamine is preferred. The lipid fraction of such liposomes and lipoplexes, respectively, was 50 mol % beta-arginyl-2,3-diaminopropionic acid-N-palmityl-N-oleyl-amide trihydrochloride and either 50 mol % 1,2-diphytanoyl-sn-glycero-3-phosphoethanolamine or 50 mol % 1,2-dioleyl-sn-glycero-3-phosphoethanolamine.

The combination of 50 mol % β-arginyl-2,3-diaminopropionic acid-N-palmityl-N-oleyl-amide trihydrochloride and 50 mol % 1,2-diphytanoyl-sn-glycero-3-phosphoethanolamine is also referred to herein as atuFect.

It is to be understood that in principle any other lipid and lipid composition as disclosed herein can be manufactured using the previously mentioned techniques as well as the further processing steps.

The liposomes and lipoplexes, respectively, are subjected to further processing steps so as to trim them with regard to size, polydispersibility and lamellarity. These characteristics can be adjusted by sonication, extrusion such as through porous membranes, and homogenisation, preferably high pressure homogenisation.

Figure 12A:
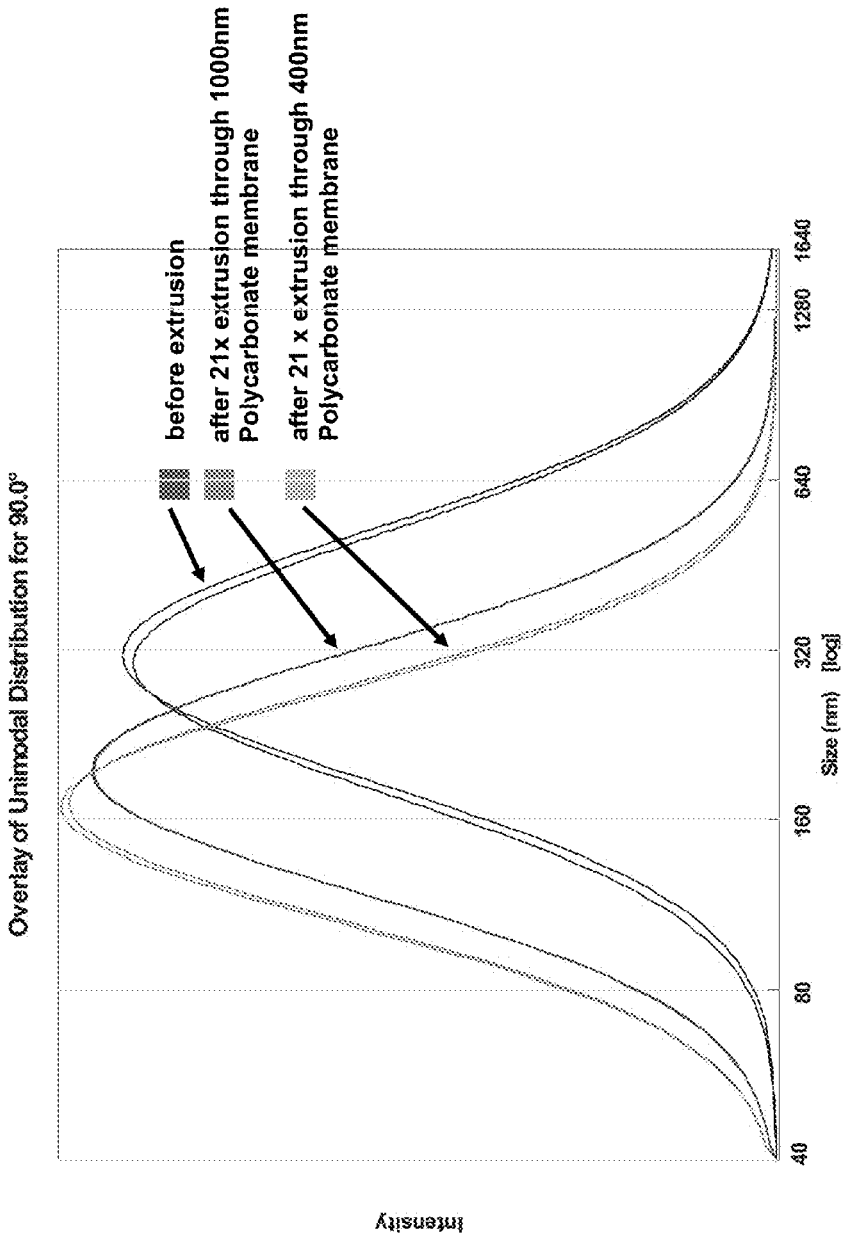
FIGS. 12A and 12B depict the size distribution of lipid formulations according to the present invention and the impact of extrusion and high-pressure homogenisation, respectively.
Figure 12B:
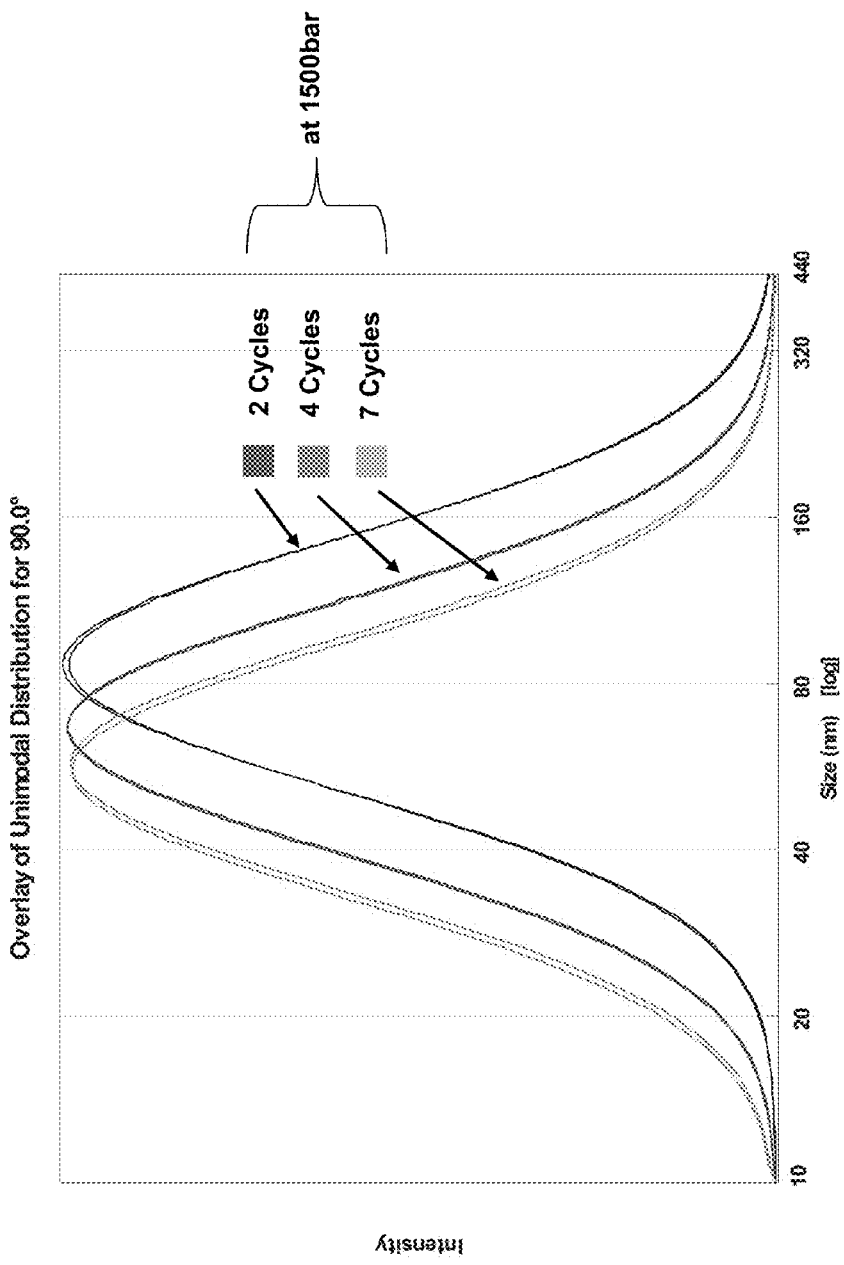

The thus formed liposomes or lipoplexes were characterised by photon correlation spectroscopy with Beckman-Coulter N 5 submicron particle analyser and the results of such liposomes either sized by extrusion or by high-pressure homogenisation are depicted in FIGS. 12A and 12B, respectively.

From FIG. 12A it can be taken that the size distribution of the liposomes can be modified using different membranes having different size exclusions, in the present case 1,000 nm and 400 nm, respectively. In both cases, the extrusion step was repeated 21 times. It is, however, within the present invention that the size exclusion can be from about 50 to 5000 nm, and that the extrusion steps can be repeated 10 to 50 times.

As may be taken from FIG. 12B high-pressure homogenisation is also a suitable means to modify the size distribution of the liposomes, whereby upon applying such high-pressure homogenisation the size of the liposomes depends on the number of homogenisation cycles to which the liposomes were subjected. Typical pressure ranges are from 100-2500 bar, whereby in the present case the applied pressure was 1,500 bar.

EXAMPLE 19

Storage Stability of Atufect

If the compositions disclosed herein are typically used as pharmaceutical compositions, it is essential that such pharmaceutical formulations are stable to storage conditions. In order to study the storage stability an siRNA was designed against tumor suppressor PTEN which was formulated using atuFect as described in example 18.

More particularly, liposomes were manufactured using a lipid stock solution with the final stock concentrations being recited below, by lipid film rehydration in 300 mM sucrose solution, followed by extrusion and high pressure homogenisation, respectively. The thus obtained liposomes were mixed with the siRNA molecules described below at a mol ratio of 1:1; alternatively the lipid layer could be rehydrated in the presence of siRNA and the thus obtained lipoplexes extrudated of homogenized.

The siRNA molecules were the following:

```
antisense PTENAV10:
                                         (SEQ ID NO: 1)
5' uaaguucuagcuguggugg-P 3';

sense PTENBV10
                                         (SEQ ID NO: 2)
5' ccaccacagcuagaacuua-P 3';
``` whereby bold nucleotides indicate that the respective nucleotide is 2'-O-methyl.

Figure 13:
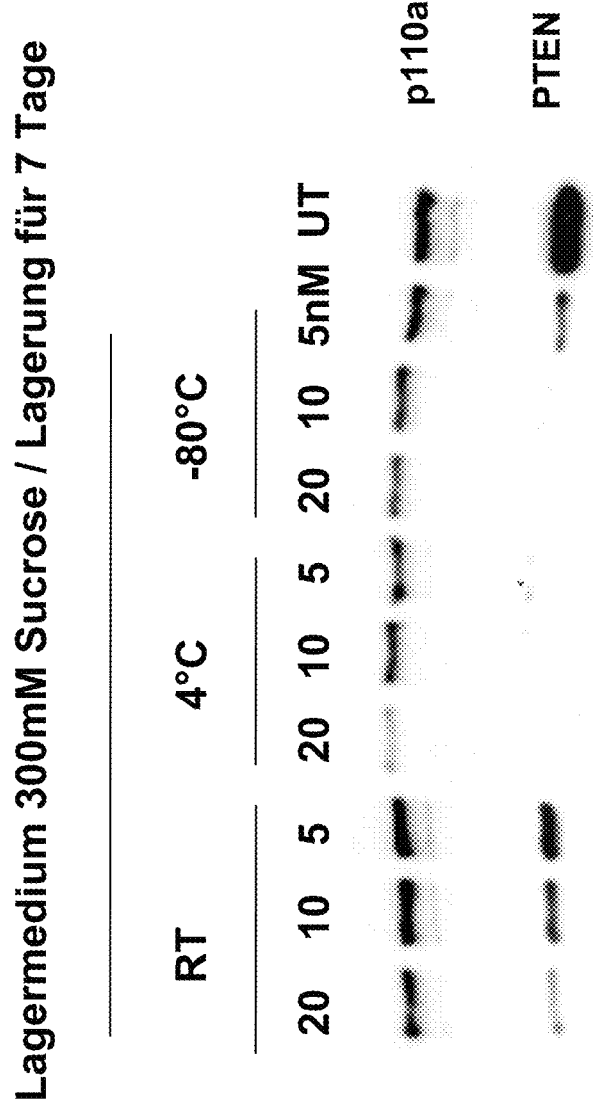
FIG. 13 depicts the result of a Western Blot analysis of an RNAi containing lipid formulation being exposed to cryoprotectants and stored at different temperatures.

The lipoplexes were incubated on HeLa cells in the presence of serum containing medium for 48 h at different concentrations (nM of siRNA molecule is shown in FIG. 13). The immunoblot with whole cell extracts using a p110a (loading control) and PTEN specific antibodies was performed as described previously (Standard-Western-Protocol).

Suitable cryoprotectants include, however, are not limited to, sucrose, trehalose, maltose, cellobiose, raffinose, galactose, mannitole and PEG. In the present example, a 300 mM sucrose solution was used as a carrier for the atuFect formulation containing the PTEN targeting siRNA. The final stock concentrations were total lipids 1,445 mg/ml and 15 μM PTEN-siRNA. The solution was kept either at room temperature, stored at 4° C. for seven days or stored at −80° C. for seven days. Said solution was diluted in serum-containing medium to the indicated final concentration (20, 10, 5 nM). Tests were performed on HeLa cells with a cell density of 40,000 well. The results are depicted in FIG. 13 from which it can be taken that freezing atuFect containing siRNA in a cryoprotectant and storing the same at −80° C. for seven days is, after thawing, as effective as if it was kept at 4° C.

EXAMPLE 20

Lipid Composition and siRNA Load

Two different types of lipid formulations were prepared. Lipid formulation 01 consisted of 50 mol % β-arginyl-2,3-diamino propionic acid-N-palmityl-N-oleyl-amide trihydrochloride as cationic lipid, and of 50 mol % 1,2-diphytanoyl-sn-glycero-3-phosphoethanolamine, whereas lipid formulation 02 consisted of 50 mol % β-arginyl-2,3-diamino propionic acid-N-palmityl-N-oleyl-amide trihydrochloride as cationic lipid, and of 50 mol % 1,2-dioleyl-sn-glycero-3-phosphoethanolamine. Each lipid formulation contained an siRNA directed against PTEN, (stock concentration was 15 μM siRNA and 1,445 mg/ml lipids), whereby the molarity of the siRNA was titrated on the cells leading to an end concentration of 1 μM, 500 nM, 100 nM and 50 nM, respectively.

Figure 14:
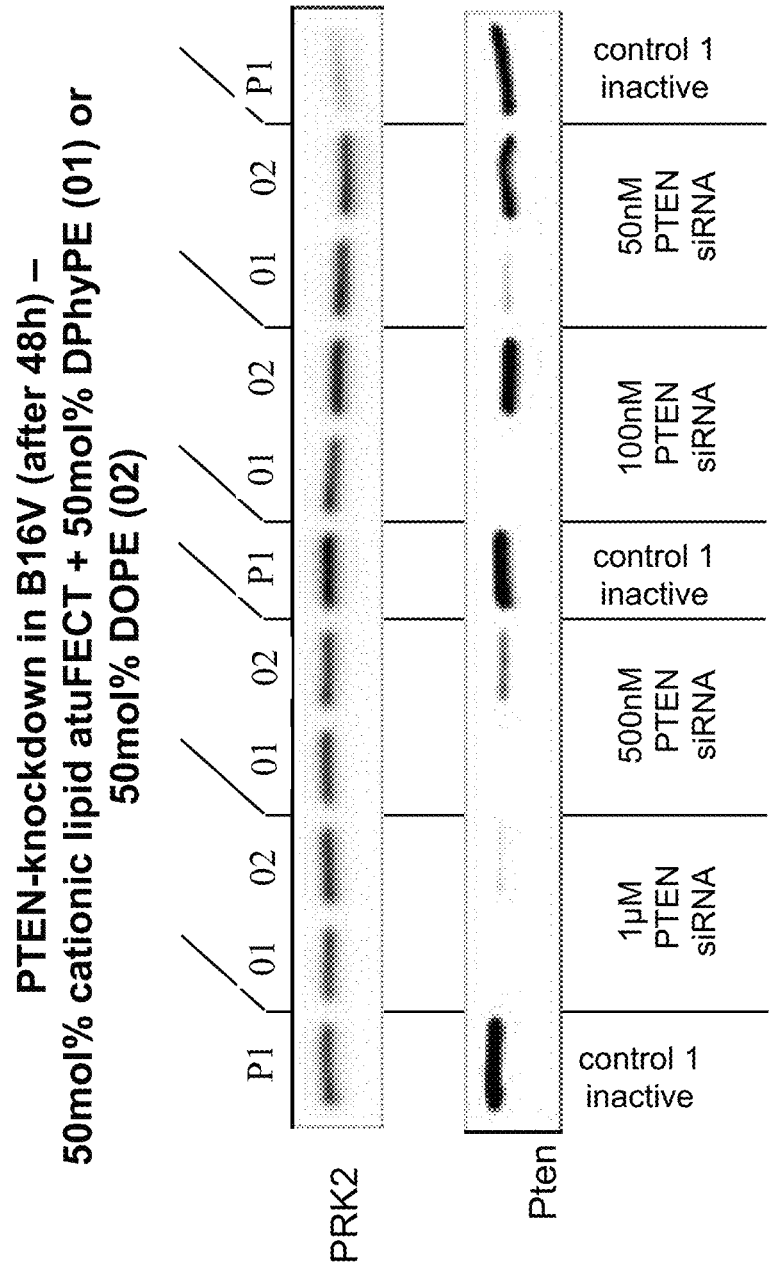
FIG. 14 depicts the result of a Western Blot analysis on the impact of different siRNA loads on lipid formulations differing in their helper lipid.

These PTEN specific RNAi containing lipid formulations were administered to a mouse cell line (B16V, ATCC No.: CRL6475) grown under standard cell culture conditions in Dulbecco's modified Eagle's medium with 4 mM L-glutamine adjusted to contain 1.5 g/L sodium bicarbonate and 4.5 g/L glucose, 90%; fetal bovine serum, 10%. The cell density was 40.000 cells/6 well and after 48 hours the cells were lysed and subjected to a Western Blot analysis the result of which is depicted in FIG. 14. The signal obtained with an monoclonal antibody specific for the kinase PRK2 (Becton Dickinson) was used as a loading control in comparison to the PTEN signal (monoclonal antibody, Santa Cruze, Calif.).

From FIG. 14 it may be taken that lipid formulation 01, i. e. the one containing 1,2-diphytanoyl-sn-glycero-3-phosphoethanolamine was still effective if the siRNA content was nM, whereas lipid formulation 02 containing 1,2-dioleyl-sn-glycero-3-phosphoethanolamine as helper lipid could generate a knockdown of the PTEN only if the siRNA content was about 1 μM or more as detected by a PTEN specific antibody (Santa Cruze, Calif.). The signal of the unrelated kinase PRK2 was used as a loading control and detected by an antibody directed thereto.

EXAMPLE 21

Lipid Composition and Peg Content

In order to test the impact of PEG on the efficacy on transfection and delivery of lipid compositions comprising β-arginyl-2,3-diaminopropionic acid-N-palmityl-N-oleyl-amide trihydrochloride (cationic lipid) as lipid component and 1,2-diphytanoyl-sn-glycero-3-phosphoethanolamine (DPhyPE) and 1,2-distearoyl-sn-glycero-3-phosphoethanolamine-polyethylenglycol-2000 (DSPE-PEG2000) the following formulations were generated in accordance with the methods disclosed herein:

| | Cationic lipid [mol %] | DPhyPE [mol %] | DSPE-PEG [mol %] |
|---|---|---|---|
| $C_1$-$C_5$ formulations: | | | |
| $C_1$ | 49 | 50 mol % | 1 |
| $C_2$ | 48 | 50 mol % | 2 |
| $C_3$ | 47 | 50 mol % | 3 |
| $C_4$ | 46 | 50 mol % | 4 |
| $C_5$ | 45 | 50 mol % | 5 |
| $H_1$-$H_5$ formulations: | | | |
| $H_1$ | 50 mol % | 49 | 1 |
| $H_2$ | 50 mol % | 48 | 2 |
| $H_3$ | 50 mol % | 47 | 3 |
| $H_4$ | 50 mol % | 46 | 4 |
| $H_5$ | 50 mol % | 45 | 5 |

For any of the aforementioned formulations the lipid concentration was 1.445 mg/ml, siRNA concentration was 15 µM in 300 mM sucrose. Dilution of the concentrated stock-complexes formed yielded an end concentration of 20, 10, 5 nM siRNA in the cell culture medium.

Figure 15:
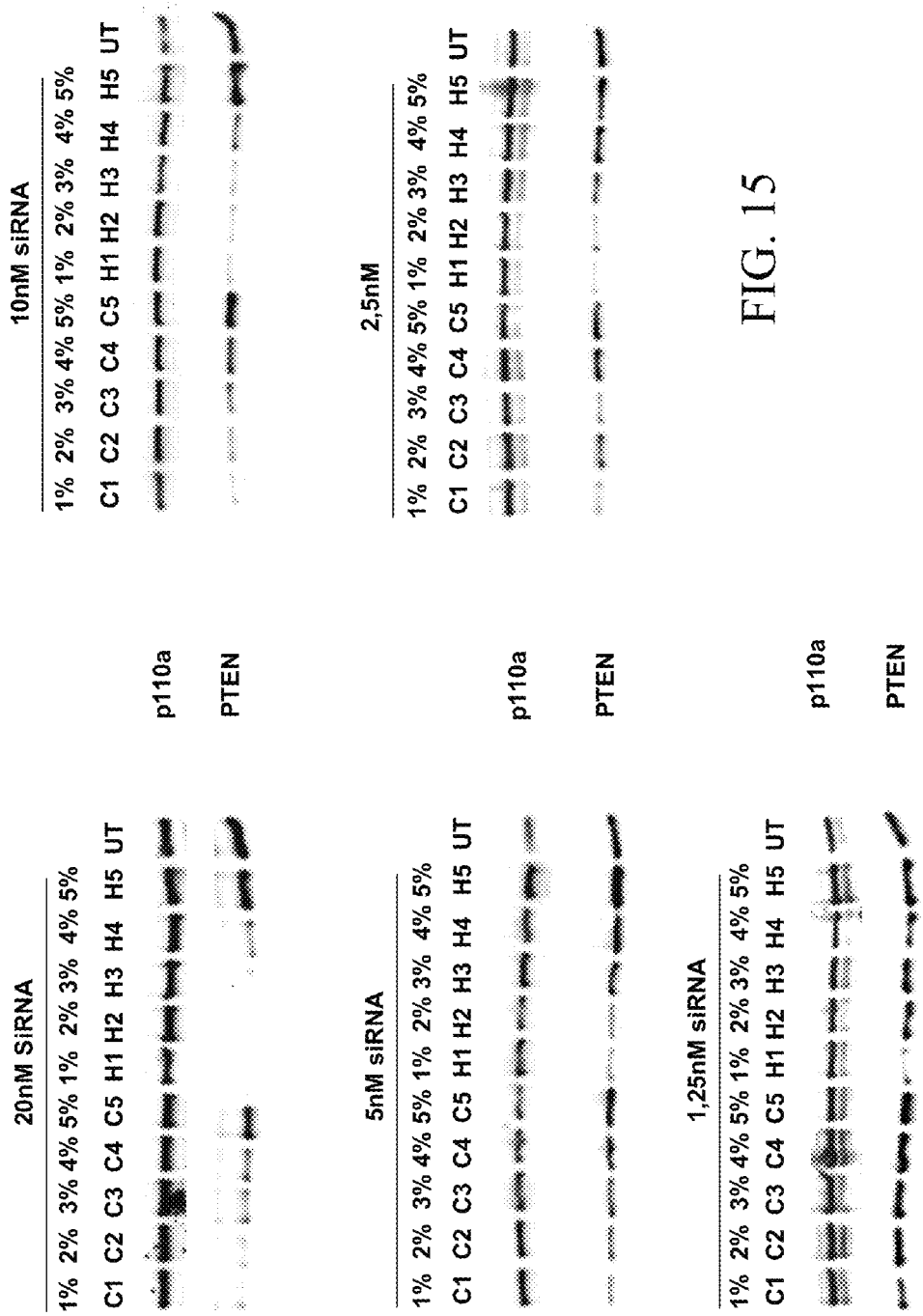
FIG. 15 depicts the result of a Western Blot analysis and the impact of different concentrations of PEG-substituted lipids.

The RNAi molecules contained in said formulations were directed against PTEN and the sequences are described in example 22. The lipid formulations were administered to HeLa cells contained in a 6 well plate each containing 40,000 cells/well. The cells were analysed for expression of PTEN and the results depicted in FIG. 15 as Western Blots. p110a expression was used as loading control and detected by a monoclonal antibody specific for p110a. From any of the Western Blots depicted in FIG. 15 it can be taken that about 1 to 2 mol % of the helper lipid containing PEG was suitable to provide an efficient knockdown of the PTEN expression.

It can be concluded that, preferably, the DPhyPE component is to be replaced by the PEGylated helper lipid rather than the cationic lipid component is replaced by the PEGylated helper lipid. This can be taken from the above experiment where the H formulations seem to be more potent than the C formulations. The content of the PEGylated helper lipid is preferably from about 0.05% to 4.9%, preferably 1 to 3% and more preferably 2 to 3%.

EXAMPLE 22

In Vivo Use of an siRNA Containing Lipid Formulation

Figure 16:
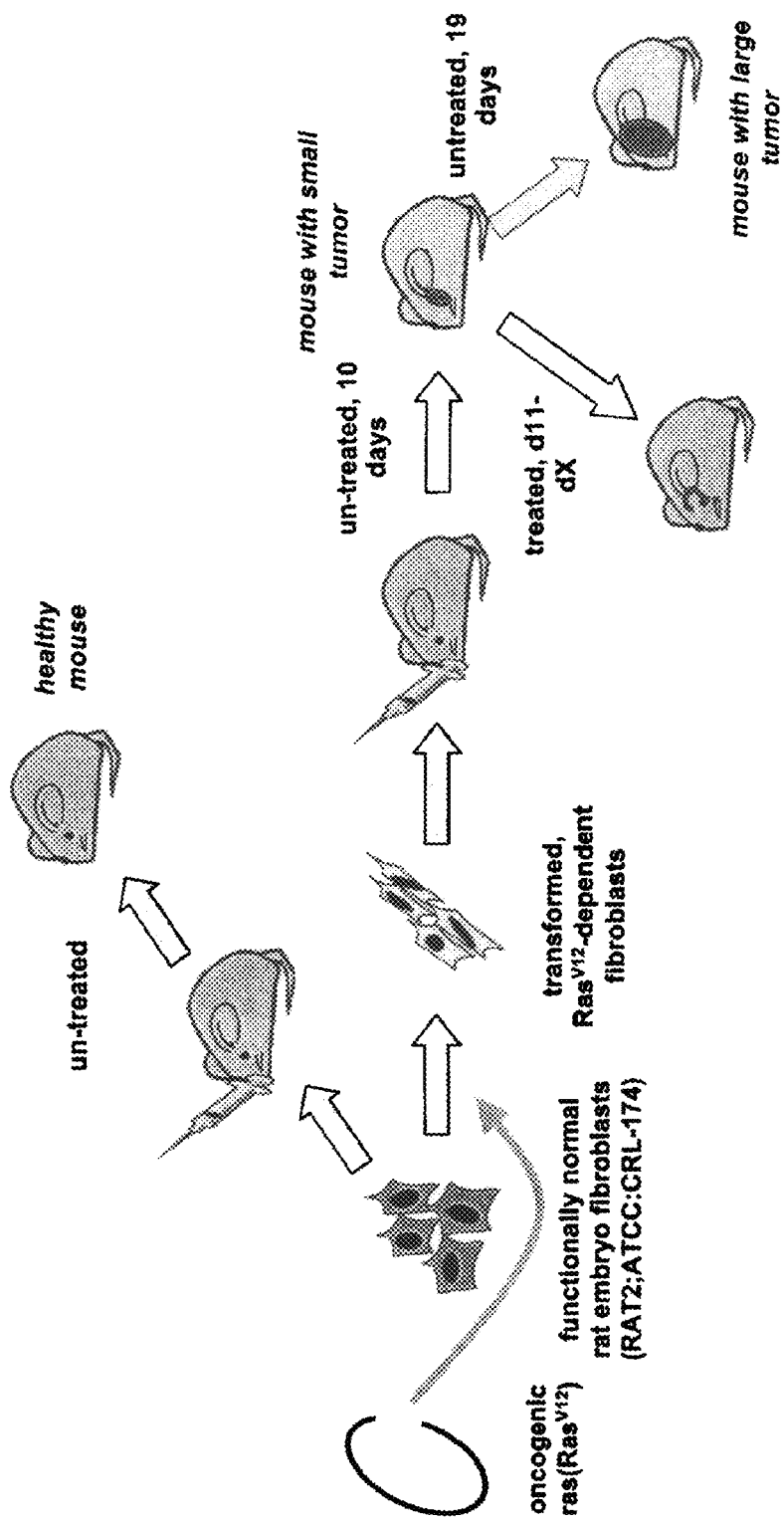
FIG. 16 depicts the experimental set up used to generate a RasV12-dependent tumor mouse model and its use in testing various formulations.

In order to test the suitability of the siRNA containing lipid formulations according to the present invention, the lipid formulations were used in a mouse model. In contrast to the so-called hydrodynamic pressure injection frequently used to deliver siRNA to the liver in vivo where a volume corresponding to about 10% body weight which is about 2.5 ml of liquid per mouse is rapidly injected into the tail vein, the present in vivo experiments were carried out such that the siRNA containing lipid formulations were administered systemically at low volumes (200 to 300 µl) which were slowly, i.e. over several seconds, injected into the tail vein of mice thus practising a clinically-relevant mode of administration. The experimental set up is depicted in FIG. 16.

Functionally normal rat embryo fibroblasts (RAT2; ATCC:CRL-174) were transformed using oncogenic Ras (Ras$^{V12}$) The transformed Ras$^{V12}$ dependent fibroblasts were subsequently injected into mice (6 mice per group; eight-week-old male Shoe:NMRI-nu/nu, DIMED, Germany) which developed a tumor after ten days. At this stage, said animals were either untreated until day 19 after injection of the transformed fibroblasts or treatment using various formulations was started on day 11. As a further control functionally normal rat embryo fibroblasts were injected into mice which did not develop a tumor.

The siRNA molecule which is referred to herein as T-Ras consisted of a first strand T-Ras 3A having the following sequence: aacguguagaaggcauccu-P (SEQ ID NO: 3) in 5'-3' direction and a second strand T-Ras 3B having the following sequence: aggaugccuucuacacguu-P (SEQ ID NO: 4) in 5'-3' direction. Please note that the nucleotides which are printed in bold and which are underlined, are 2'-O-methyl nucleotides. At any of the strands, the 3' end starts with a phosphate depicted by P in the aforementioned sequences.

As a control a PTEN specific siRNA molecule was designed with a first strand having the following sequence: 5' uaaguucuagcuguggugg-P 3' (SEQ ID NO: 8) and a second sequence 5' ccaccacagcuagaacuua-P 3' (SEQ ID NO: 9), whereby the modification pattern is the same as outlined in connection with T-Ras 3A and T-Ras 3B, respectively.

The following formulations were administered to the mouse model:
Formulation Panel A:
  PBS;
  T-Ras 3: 10 mg/kg/atuFect/3.7 mg/kg;
  naked T-Ras 3 10 mg/kg; and
  T-Ras 3: 5 mg/kg/atuFect 38.5 mg/kg.
Formulation Panel B:
  PBS;
  atuFect only 38.5 mg/kg;
  PTEN 10 mg/kg/atuFect 38.5 mg/kg; and
  T-Ras 3: 5 mg/kg/atuFect 38.5 mg/kg.
Formulation Panel C:
  sucrose (50 mM);
  T-Ras 3: 3.75 mg/kg/atuFect-PEG 28.9 mg/kg, administered i.v.; and
  T-Ras 3: 3.75 mg/kg/atuFect-PEG 28.9 mg/kg, administered i.p.
atuFect-PEG as used herein means 50 mol % β-arginyl-2,3-diamino propionic acid-N-palmityl-N-oleyl-amide trihydrochloride, 48 mol % 1,2-diphytanoyl-sn-glycero-3-phosphoethanolamine and 2 mol % 1,2-distearoyl-sn-glycero-3-phosphoethanolamine-polyethylenglycol-2000 (DSPE-PEG2000), in 50 mM sucrose.

The dosage in the animals was 5 mg/kg siRNA and 38.5 mg/kg total lipids; the concentration of the components in the injection solution was 0.5 mg/ml siRNA and 3.85 mg/ml total lipids; the molar ratio was: siRNA: 0.5 mg/ml corresponding to 0.04 µmole/ml (molecular weight approximately 12500 Da). The lipid was 3.85 mg/ml overall lipid, whereby the content of the cationic lipid was 1.97 mg/ml (molecular weight 843.6) corresponding to 2.3 µmole/ml cationic lipid. The molar ratio of siRNA to cationic lipid was 0.0174 to 1.

Figure 17A:
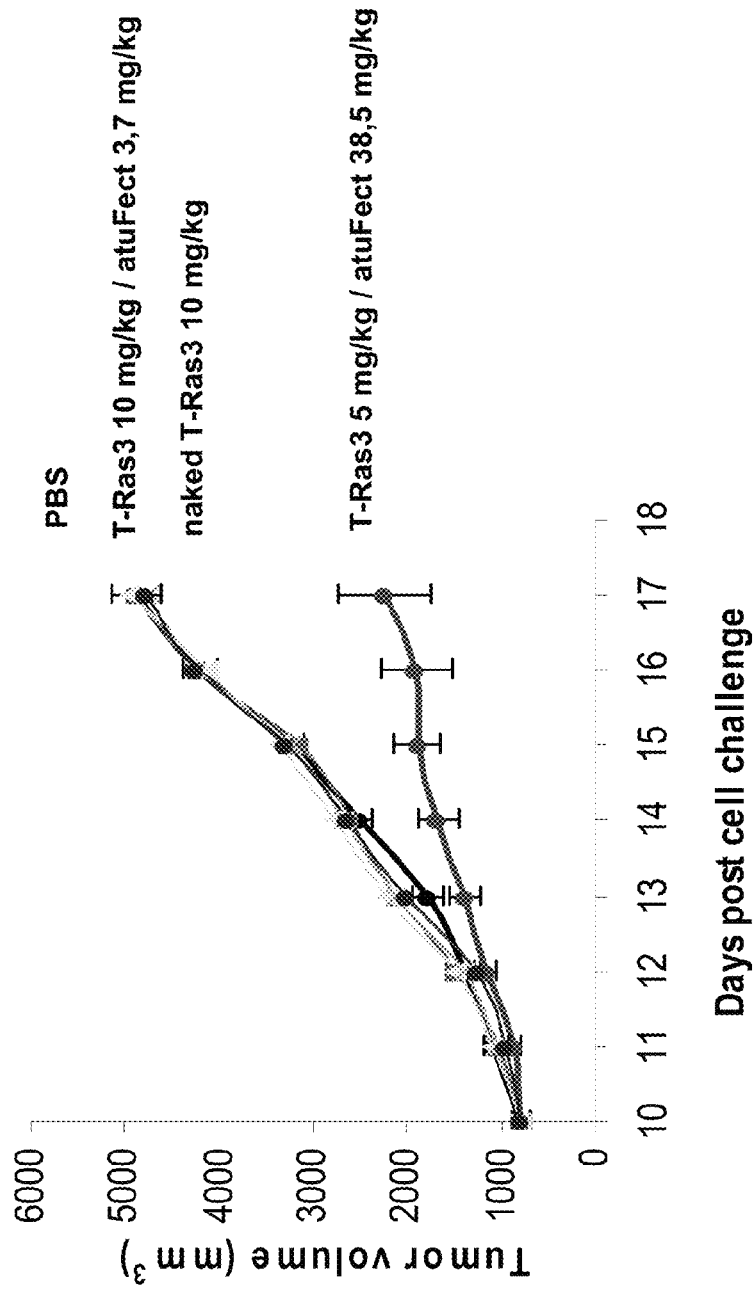
FIGS. 17A, 17B and 17C depict diagrams indicating the tumor volume as a function of days post cell challenge using different formulations.
Figure 17B:
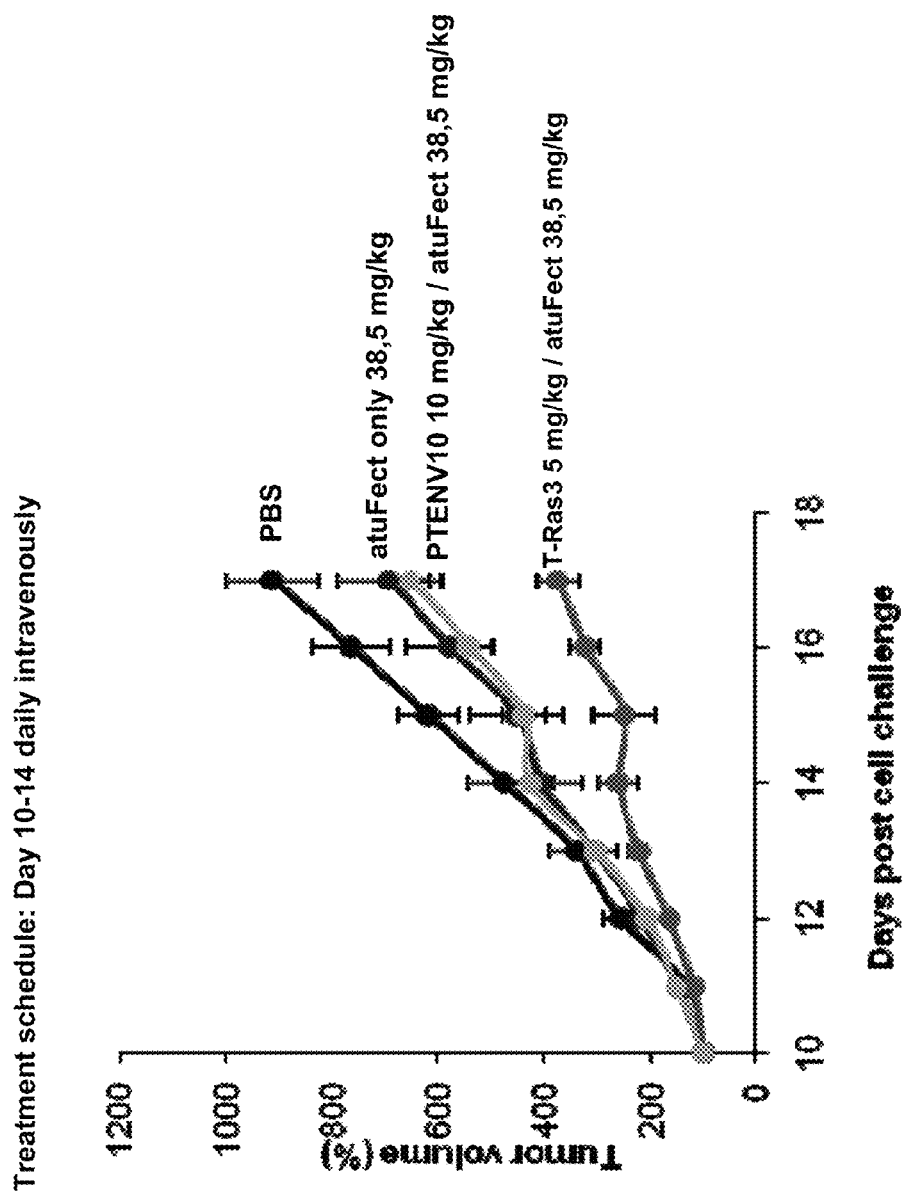
Figure 17C:
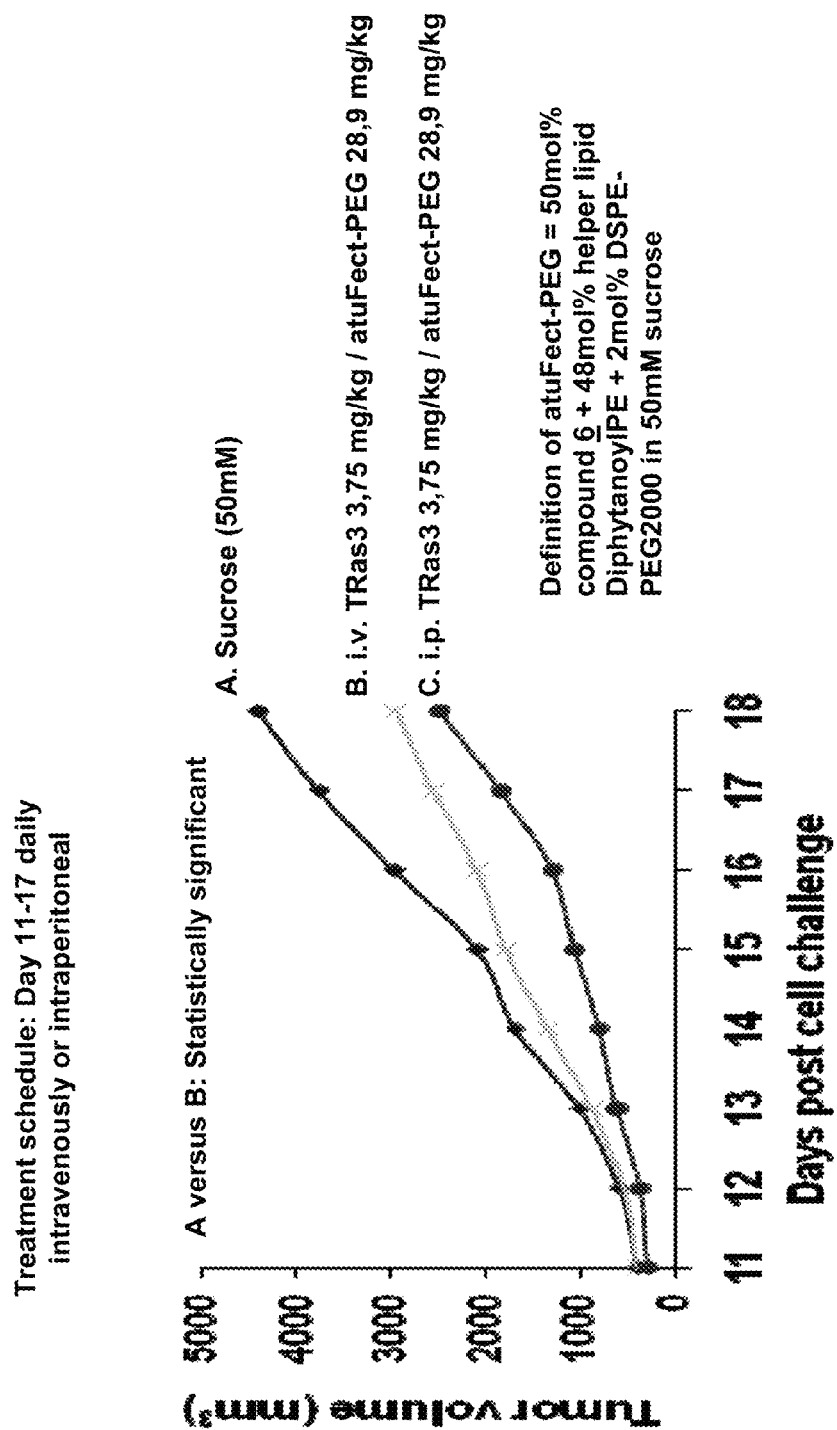

The results of these experiments are depicted in FIG. 17A (formulation panel A), FIG. 17B (formulation panel B) and FIG. 17C (formulation panel C) showing the tumor volume as a function of time, i.e. days post cell challenge.

As may be taken from both FIGS. 17A and 17B the lipoplexes consisting of T-Ras specific siRNA formulated with atuFect show the strongest inhibition and indicates specificity of targeting. It should be noted that the negative control molecule PTENV10 does not show an improved inhibition of tumor growth when compared to atuFect only (FIG. 17B). As may be taken from FIG. 17C also atuFect-PEG is highly effective and allows for both i.p. as well as i.v. administration resulting in similar efficacies. In connection therewith it is noteworthy that the PEGylated complexes are functionally active and it can be assumed that due to PEGylation such lipid compositions are less toxic than similar lipid compositions which are lacking the PEGylated (helper) lipid.

EXAMPLE 23

Material and Methods for Examples 24 to 27

Preparation of siRNA-Lipoplexes

Cationic liposomes comprising the cationic lipid β-L-arginyl-2,3-L-diaminopropionic acid-N-palmityl-N-oleyl-amide trihydrochloride, the neutral phospholipid 1,2-diphytanoyl-sn-glycero-3-phosphoethanolamine (Avanti Polar Lipids Inc., Alabaster, Ala.) and the PEGylated lipid N-(Carbonyl-methoxypolyethyleneglycol-2000)-1,2-distearoyl-sn-glycero-3-phosphoethanolamine sodium salt (Lipoid GmbH, Ludwigshafen, Germany) in a molar ratio of 50/49/1 were prepared by lipid film re-hydration in 300 mM sterile RNase-free sucrose solution to a total lipid concentration of 4.34 mg/ml. Subsequently the multilamellar dispersion was further processed by high pressure homogenization (22 cycles at 750 bar and 5 cycles at 1000 bar) using an EmulsiFlex C3 device (Avestin, Inc., Ottawa, Canada). The obtained liposomal dispersion was mixed with an equal volume of a 0.5625 mg/ml solution of siRNA in 300 mM sucrose, resulting in a calculated charge ratio of nucleic acid backbone phosphates to cationic lipid nitrogen atoms of approximately 1 to 4. The size of the lipoplex-dispersion was approximately 120 nm as determined by Quasi Elastic Light Scattering (N5 Submicron Particle Size Analyzer, Beckman Coulter, Inc., Miami, Fla.). For in vitro experiments this dispersion was further diluted to a concentration of 5-20 nM siRNA in 10% serum containing cell culture medium.

Animal Experiments

Athymic male nude mice (Hsd:NMRI-nu/nu, 8 weeks old) were used throughout this study. For tumor therapy experiments on established tumor xenografts, a total of $5.0 \times 10^6$ cells/100 µl (in the presence of 50% matrigel for 3Y1-Ras$^{V12}$) were implanted subcutaneously (s.c.). For tumor therapy experiments liposomal siRNA complex solution was administered i.v. by low pressure, low volume tail vein injection. Different dosing was achieved by varying injection schedules (daily vs. bi-daily) using for a 30 g mouse a 200 µl injection volume of a stock solution containing 0.28 mg/ml siRNA and 2.17 mg/ml lipid (equivalent to a dose of 1.88 mg/kg siRNA and 14.5 mg/kg lipid). Tumor volume was determined using a caliper and calculated to according the formula volume=(length×width)/2. All animal experiments in this study were performed according to approved protocols and in compliance with the guidelines of the Landesamt für Arbeits—, Gesundheitsschutz and technische Sicherheit Berlin, Germany (No. G0264/99).

Statistical Analysis

Data are expressed as means±S.E.M. Statistical significance of differences was determined by the Mann-Whitney U test. P values <0.05 were considered statistically significant.

siRNA-Cy3 Uptake Experiment in Cell Culture and Mice

For uptake studies of non-formulated siRNA-Cy3 molecules in cell culture HeLa cells were incubated with defined amounts of siRNA solution overnight in serum-free medium. Uptake of lipoplexed siRNA-Cy3 cells was carried out by transfection overnight as mentioned below. Treated cells were rinsed with ice cold PBS and fixed in 4% formaldehyde/PBS solution for 15 minutes prior to microscopy. To label late endosomes and lysosomes, cells were incubated with the fluorescent dye LysoTracker (Molecular Probes) according to the manufacturers' recommendation and examined by confocal miscroscopy after fixation. In vivo delivery experiment using fluorescently labeled siRNA-Cy3, were carried out by administering formulated and naked siRNA intravenously. Mice were treated with a single 200 µl i.v. injection at a final dose of 1.88 mg/kg siRNA-Cy3 and 14.5 mg/kg lipid. Mice were sacrificed at defined time-points and fluorescence uptake examined by microscopy on either formalin fixed, paraffin embedded or OCT mounted frozen tissue sections.

In Vitro Transfection

Human HUVEC, HeLa, PC-3 cell lines as well as murine EOMA and NIH3T3 cell lines were obtained from American Type Culture Collection and cultivated according to the ATCC's recommendation. Human hepatoma cell line HuH-7 was available at MDC, Berlin. Rat 3Y1 cells expressing oncogenic Ras$^{V12}$ were generated by transduction of inducible Ras$^{V12}$ as described[38].

Cell lines were transfected with siRNA using the cationic liposomes described above. Briefly, about 12 hours after cell seeding different amounts of siRNA-lipoplex solution diluted in serum containing medium were added to the cells to achieve transfection concentrations in a range of 1-50 nM siRNA. After transfection (48 h) cells were lysed and subjected to immunoblotting as described[20]. Following antibodies were used for immunoblotting: Rabbit anti-PTEN (Ab-2, Neomarkers), monoclonal p110α/p85[39], rabbit anti-PKN3[38], goat anti-CD31 (Santa Cruz Biotechnology), rabbit anti-CD34 (Santa Cruz Biotechnology), rabbit anti-phosphorylated Akt (S473) (Cell Signaling Technology).

In Vivo BrdU Assay

To measure cell proliferation in vivo, mice were treated with BrdU (Sigma; 250 mg/kg) by intraperitoneal injection and sacrificed two hours later. Formalin fixed paraffin embedded sections of liver or tumor tissue were subjected to BrdU staining according to the manufacturers' protocol (BrdU In situ detection kit, Pharmingen).

Determination of Microvessel Density (MVD)

The number of microvessels was determined by counting CD31-/CD34-positive vessels in 3-8 randomly selected areas of single tumor sections[24]. Vessel number as vascular units was evaluated regardless of shape, branch points and size lumens (referring to "number of vessels"). Additionally, vascular density was assessed by determination of total length of CD31-/CD34-positive vessel structures (referring to "sum of vessel lengths") using the Axiovision 3.0 software (Zeiss). Counting was performed by scanning tumor sections at 200× magnification with a Zeiss Axioplan light microscope.

Histological Analysis and Microscopy

After mice were sacrificed, tissues were instantly fixed in 4.5% buffered formalin for 16 hours and consequently processed for paraffin embedding. 4 µm sections were cut and placed on glass slides. Tissue sections were stained with goat polyclonal anti-CD31/PECAM-1 (1:1000, Santa Cruz Biotechnology) (alternatively for cryosections rat CD31, 1:100, Pharmingen) and rat-monoclonal anti-CD34 (Cedarlane) to visualize endothelial cells in paraffin sections. Immunohistochemistry and hematoxylin/eosin (H&E) counterstaining on paraffin tissue sections were performed according to standard protocols. For in vivo uptake studies of fluorescently labeled siRNAs, paraffin sections were directly examined by epifluorescence with a Zeiss Axioplan microscope. Images were recorded and processed using the Zeiss LSM5 imaging software. In depth microscopic analysis of siRNA uptake was performed with a Zeiss LSM510 Meta confocal microscope. For this, sections were deparaffinized with xylene, rehydrated through graded ethanol washes, counterstained with Sytox Green dye (Molecular Probes 100 nM; 10 min), rinsed and finally mounted in FluorSave (Calbiochem) for microscopy. Immunofluorescence staining of NIH3T3 cells was performed as described[40], using the following antibodies: the immunohistochemistry-specific rabbit anti-phosphorylated-Akt (S473) (Cell Signaling Technology) and mouse anti-α-tubulin (DM1A, Calbiochem).

TABLE 1 siRNA sequences as used throughout examples 24 to 27

| siRNA name | sequence 5' to 3' |
|---|---|
| PKN3 s | gagagccuguacugcgaga (SEQ ID NO: 5) |
| PKN3 as | ucucgcaguacaggcucuc (SEQ ID NO: 6) |
| PTEN s | ccaccacagcuagaacuua (SEQ ID NO: 7) |
| PTEN as | uaaguucuagcuguggugg (SEQ ID NO: 8) |
| PTEN s (control) | ccaccacagcuagaacuua (SEQ ID NO: 9) |
| PTEN as (control) | uaaguucuagcuguggugg (SEQ ID NO: 10) |
| PTEN s | ccaccacagcuagaacuua (SEQ ID NO: 11) |
| PTEN as-Cy3 | uaaguucuagcuguggugg-Cy3 (SEQ ID NO: 12) |
| CD31-1 s | Ccaacuucaccauccagaa (SEQ ID NO: 13) |
| CD31-1 as | Uucuggauggugaaguugg (SEQ ID NO: 14) |
| CD31-2 s | Ggugauagcccggguggau (SEQ ID NO: 15) |
| CD31-2 as | Auccaccggggcuaucacc (SEQ ID NO: 16) |
| CD31-6 s | Ccacuucugaacuccaaca (SEQ ID NO: 17) |
| CD31-6 as | uguuggaguucagaagugg (SEQ ID NO: 18) |
| CD31-8 s | cagauacucuagaacggaa (SEQ ID NO: 19) |
| CD31-8 as | uuccguucuagaguaucug (SEQ ID NO: 20) | nucleotides with 2'-O-methyl modifications are underlined

EXAMPLE 24

Delivery of Naked and Formulated siRNAs In Vitro and In Vivo

In this study, we employed 19-mer siRNA duplexes lacking 3'-overhangs, which are chemically stabilized by alternating 2'-O-methyl sugar modifications on both strands[16], whereby unmodified nucleotides are facing modified on the opposite strand. The siRNA molecules actually used are depicted in example 23.

Figure 18A:
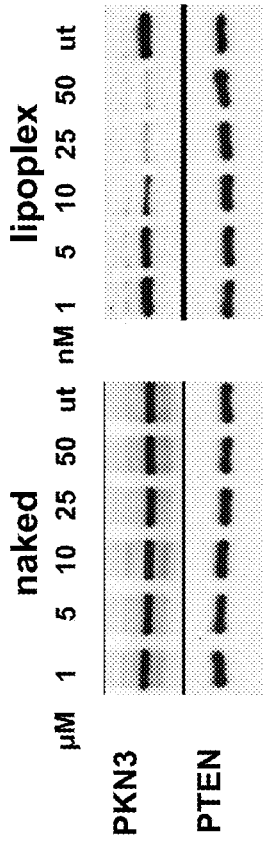
FIG. 18A depicts the result of a Western blot analysis of the effect of naked and lipoplexed PKN3 specific siRNA.

In a first step, we analyzed whether these molecules mediate RNAi in cell culture in the absence of delivery vehicles. Immunoblot analysis demonstrated that no gene silencing occurred when naked siRNA was applied at even micromolar concentrations compared to nanomolar concentrations used for siRNA-lipoplexes. The results are shown in FIG. 18A.

As may be taken from FIG. 18 in more detail, there was a concentration dependent inhibition of PKN3 protein expression with lipoplexed siRNAs, but not naked siRNA in HeLa cells as assesses by immunoblot. PTEN served as loading control.

We also tested unmodified conventional siRNAs (21-mer, 2 nucleotides 3'-overhangs)[6] and several conjugated molecules including cholesterol-conjugated or peptide-linked siRNAs, but not detect any target specific reduction of endogenous protein expression in the absence of delivery vehicles (data not shown).

To analyze whether the lack of gene silencing was the result of an inefficient cellular uptake due to repulsive effects between the anionic siRNAs and the negatively charged cell membrane we employed 3' fluorescently (Cy3) labeled siRNAs to study their uptake by confocal microscopy. We, and others have previously shown that fluorescence labeling at the 3' end of the antisense molecule does not impair RNA silencing activity when transfected with delivery vehicles[16,17]. Surprisingly, we observed a significant uptake of fluorescently labeled siRNAs in the absence of transfection reagents when high concentrations of siRNA-Cy3 molecules were applied. However, the majority of the fluorescence label appeared to end up in late endosomal/lysosomal vesicles as demonstrated by co-localization with the LysoTracker marker suggesting that unformulated siRNAs remain trapped in the endosomal pathway. In contrast, siRNAs transfected as liposomal complexes dissociated from these vesicles and were released into the cytoplasm. These results indicate that liposomal formulation of siRNAs provides at least two beneficial effects for functional delivery of siRNAs: an improved cellular uptake and importantly the escape from the endocytotic/endosomal pathway into the cytoplasm[18], where RNAi-mediated mRNA degradation takes place.

Figure 18B:
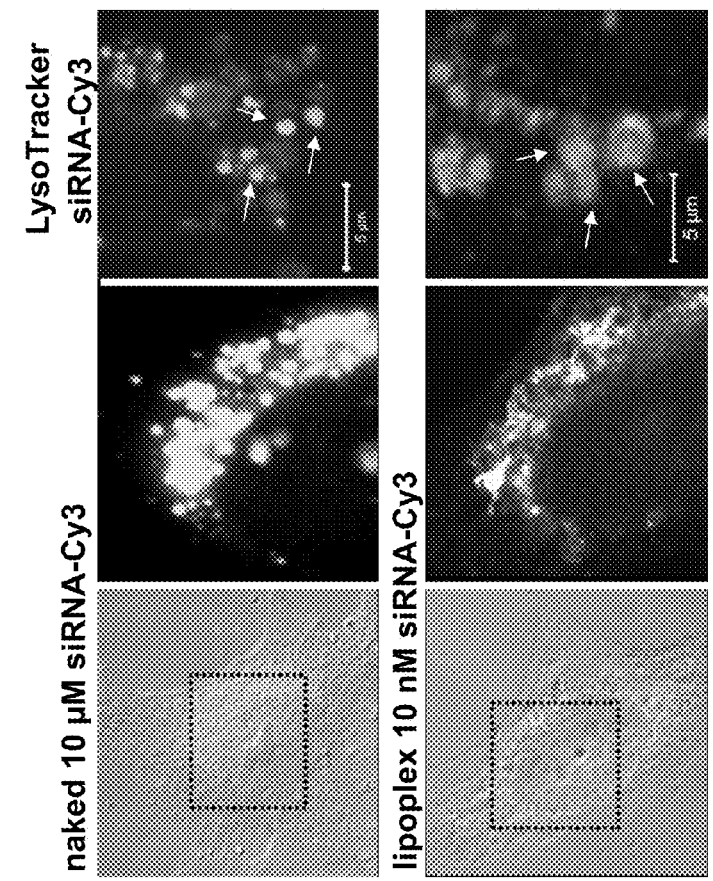
FIG. 18B are confocal microscopyphotographs showing the intracellular distribution of naked and formulated siRNAs.

The details of FIG. 18B are as follows.

FIG. 18B shows the intracellular distribution of naked and formulated siRNAs. Fluorescently labeled siRNAs-Cy3 were analyzed by confocal microscopy in HeLa cells left and middle panels. Right panels show merged pictures of subcellular distribution after counterstaining with LysoTracker (green; arrows, siRNA-Cy3 localization with respect to the endosomal/lysosomal compartment). Upper row, naked siRNA-Cy3; lower row lipoplexed siRNA-Cy3.

To analyze whether the liposomal formulation changes the pharmacological properties of siRNAs in vivo, we injected (low volume and low pressure) a single dose of siRNA-Cy3 molecules (1.88 mg/kg siRNA) into the tail vein of mice. Microscopic analysis of several organs including pancreas, lung, kidney, and prostate showed a significant increase in Cy3 specific fluorescence with formulated siRNAs (data not shown). The highest amount of fluorescence was detected in the liver of mice treated with liposomally formulated siRNAs at all analyzed time points (1 h, 4 h, 24 h post injection, FIG. 18C). This result indicates a better biodistribution of the siRNA molecules formulated in lipoplexes when compared to administration of naked siRNAs.

Figure 18D:
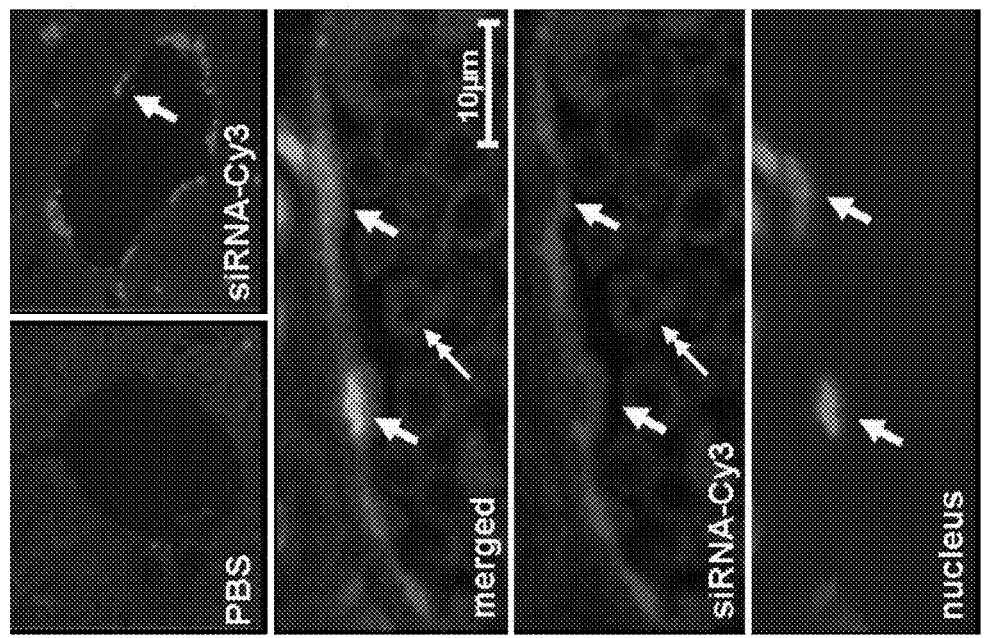
FIG. 18D are epifluorescence and confocal microscopy photographs of endothelial cells targeted with liposomal formulated siRNAs.
Figure 18C:
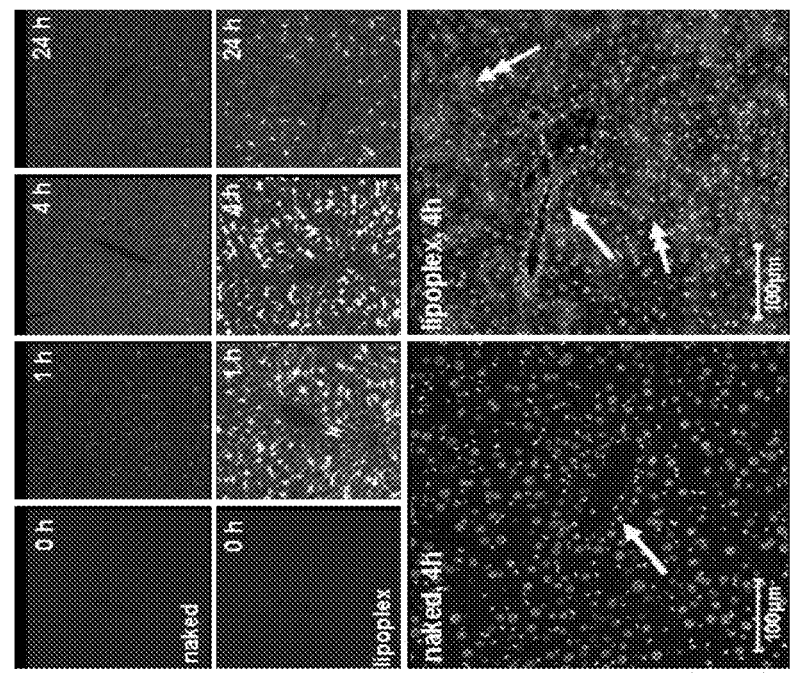
FIG. 18C are epifluorescence microscopy (upper panels) and confocal microscopy photographs (lower panel) depicting the distribution of liposomal formulated and naked siRNAs in liver.
Figure 18E:
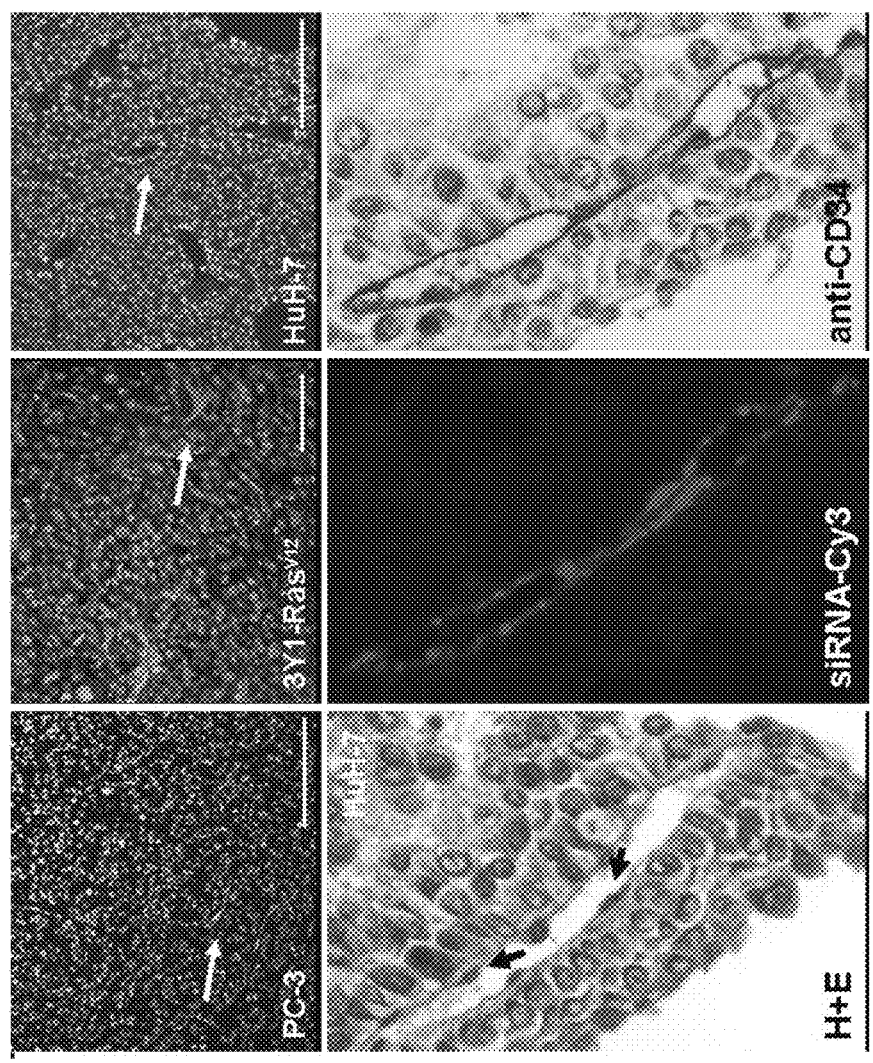
FIG. 18E are fluorescence microscopy photographs of endothelial cells of different tumors.

However, the improved biodistribution in whole organs does not necessarily indicate an intracellular or cell type specific uptake of these molecules, which is a prerequisite for functionality of the delivered siRNAs. A more detailed analysis of formulated siRNA-Cy3 uptake in the liver by confocal microscopy revealed that on the cellular level fluorescence staining was predominantly present in the linings of the blood vessels and the sinusoids (FIG. 18C, lower panel). A closer inspection of liver vessels revealed that the endothelial layer is clearly labeled by the fluorescent siRNA-Cy3 in contrast to the PBS control (FIG. 18D, upper row). Inside the endothelial cell, siRNA-Cy3 is exclusively present in the cytoplasm (FIG. 18D, lower panels). The same staining pattern was observed in non-fixed liver cryosections, which rules out any formalin fixation artifacts (data not shown). To test whether fluorescently labeled lipoplexed siRNA also targets the tumor vasculature we treated mice bearing different experimental tumors with single i.v. injections of siRNA-Cy3 lipoplexes. In all three experimental tumor xenografts (two subcutaneously, s.c., and one intrahepatic, i.hep.) we detected significant fluorescence signals in the tumor vasculature (FIG. 18E, arrow). siRNA-Cy3 uptake by the endothelial layer of the tumor vasculature was confirmed by counterstaining with anti-CD34 antibody, an endothelial cell marker (FIG. 18E, lower panels). In addition, uptake of the lipoplex-siRNA by the endothelium was confirmed using fluorescently labeled lipids (not shown). Taken together, these data demonstrate that cationic lipid based formulations of siRNAs improve the kinetic and distribution properties of siRNAs and allow for a predominant uptake of siRNAs into endothelial cells.

The experimental setting for the results shown in FIG. 18C were as follows. Naked or lipolexed siRNA-Cy3 was administered by single i.v. injection and liver tissue sections of indicated time points were analyzed by epifluorescence microscopy (upper panels). Lower panels, close-up confocal microscopy images of liver sections showing distribution of non-formulated siRNA-Cy3 (left picture) compared to lipoplex (right picture, siRNA-Cy3, red; nuclei, green by counterstaining with Sytox Green). Images were recorded with identical settings. Compare staining intensity of liver vessels (arrow) and sinusoids (double arrow).

The details of FIG. 18D are as follows. The endothelial lining of a liver vessel is decorated with fluorescent siRNA-Cy3 (right panel), in contrast to the PBS treated control section (left panel). Confocal microscopy revealed cytoplasmic delivery of formulated siRNA-Cy3 (red, merged) in liver endothelial cells (red blood cells, double arrow). No fluorescence is detectable in the nucleus (green, arrows).

The experimental setting for the results shown in FIG. 18E was as follows. Endothelial cells of different tumors were targeted with liposomal formulated siRNAs as indicated by arrows (siRNA-Cy3, red; nuclei, green). The upper row shows fluorescent images of sections from subcutaneously grown PC-3 tumor (left panel) and Ras$^{V12}$ transformed 3Y1 rat fibroblast tumor (middle panel) or intrahepatically grown HuH-7 tumor (right panel). The lower row shows detection of liposome delivered siRNA-Cy3 in endothelial cells of HuH-7 tumor. The tumor endothelial cells are shown by H&E staining (left panel) characterized by their thin cytoplasm and the prominent nucleus (arrow). Consecutive sections show corresponding siRNA-Cy3 fluorescence (red, middle panel) and anti-CD34 immunostaining of the endothelial cells (right panel), respectively.

EXAMPLE 25

Figure 19A:
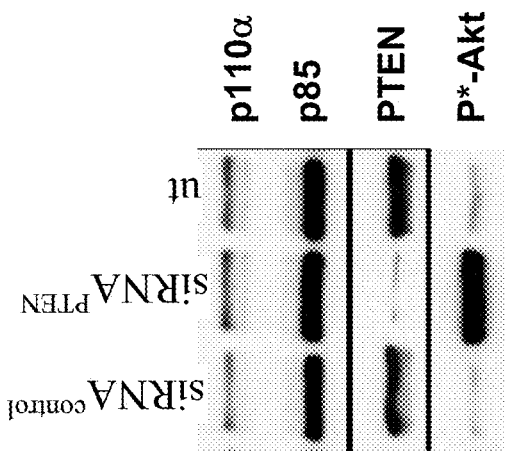
FIG. 19A is a schematic illustration of the mode of action of PTEN directed siRNA on DNA synthesis, and shows the result of a Western Blot analysis using different siRNA species and immunofluorescence microscopy photographs of HELA cells treated with said different siRNA species.
Figure 19A:
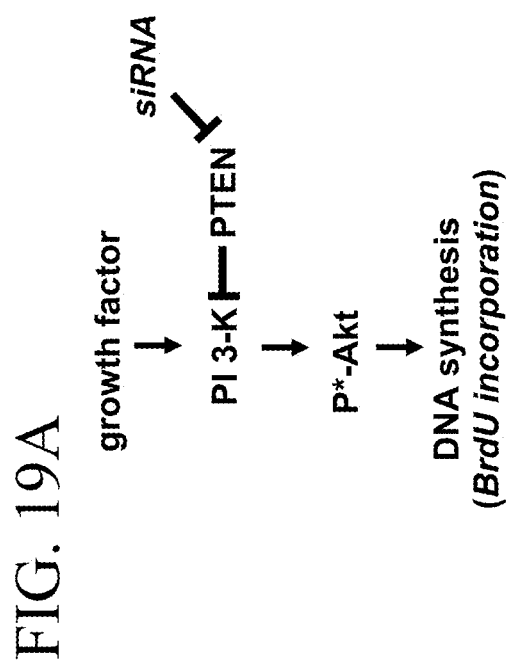
Figure 19A:
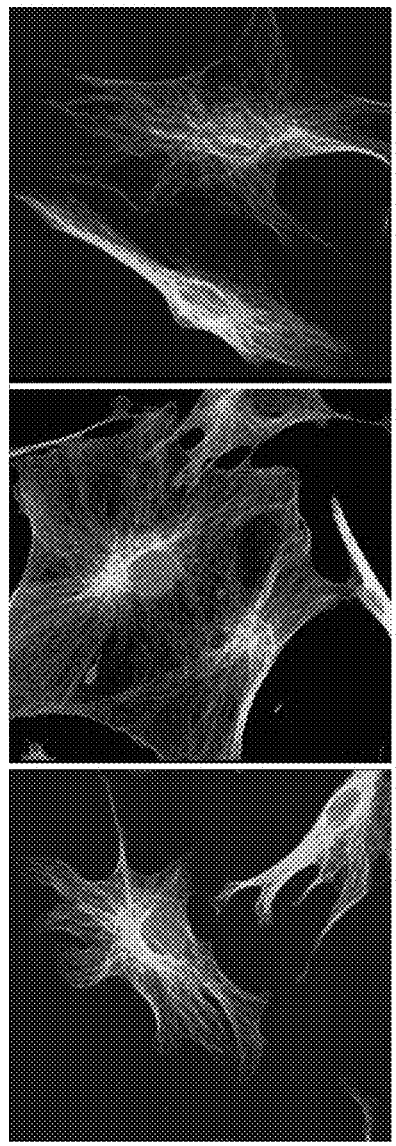

Functional Delivery of PTEN Specific siRNAs to Liver and Tumor Endothelial Cells To demonstrate the ability of siRNA-lipoplexes to silence endogenous gene expression in endothelial cells in vivo, we selected the tumor suppressor PTEN, an antagonist of phosphoinositide 3-kinase (PI 3-kinase), as a target. We intended to monitor functional gene silencing of PTEN in a positive read out system by measuring increased DNA synthesis by BrdU incorporation in endothelial cell nuclei. Loss of PTEN expression is known to chronically activate PI 3-kinase signaling, which can be measured by an increase in phosphorylation of the downstream kinase Akt[19] (FIG. 19A). Chronic activation of PI 3-kinase is also accompanied by an increased rate in DNA synthesis[20].

First, the RNAi activity of a selected siRNA$^{PTEN}$ (c.f. Example 23), targeting mouse and human PTEN mRNA, was verified by lipid-mediated transfection in vitro (FIG. 19A). The identical siRNA sequence carrying 2'-O-methyl modification at every nucleotide was used as a negative control (siRNA$^{control}$), since this uniform modification pattern abolishes RNAi activity completely[16]. PTEN protein knock-down and increased phosphorylation of Akt was observed by immunoblotting. Immunofluorescence studies confirmed the enhanced Akt phosphorylation in the presence of the active siRNA$^{PTEN}$ molecule (FIG. 19A). This demonstrates the capability of the siRNA$^{PTEN}$ molecule to activate PI 3-kinase signaling in cell culture.

Figure 19B:
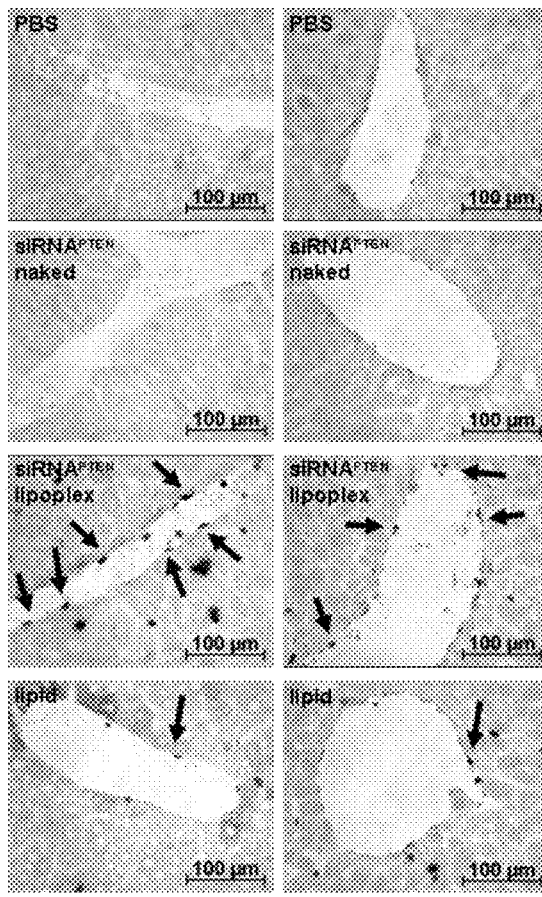
FIG. 19B depicts pictures of endothelial cells treated with different siRNA molecules and a diagram representing the result of a BrdU assay in liver endothelial cells.
Figure 19C:
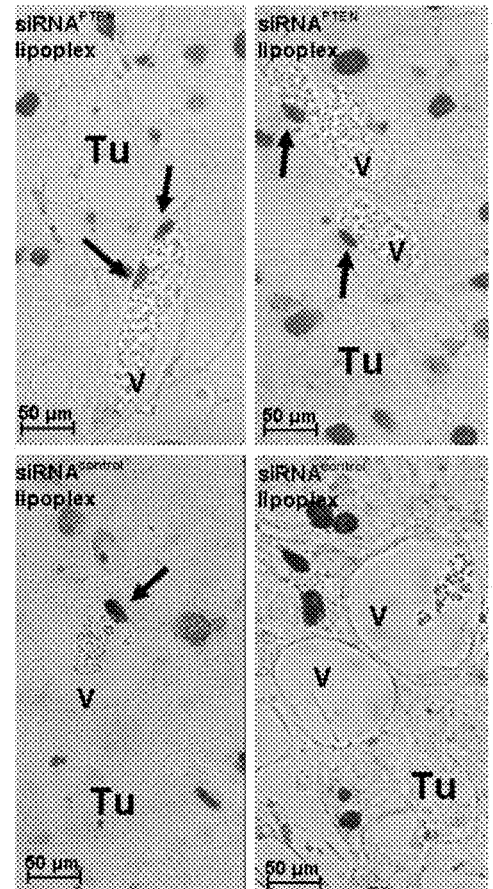
FIG. 19C depicts pictures of endothelial cells treated with different siRNA molecules and a diagram representing the result of a BrdU assay in tumor endothelial cells.
Figure 19C:
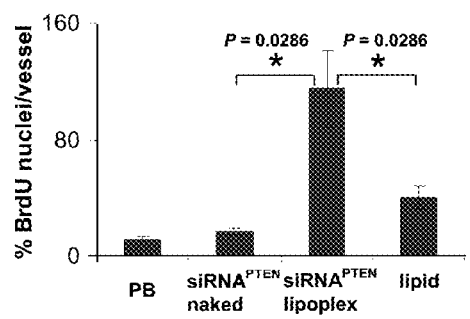
Figure 19C:
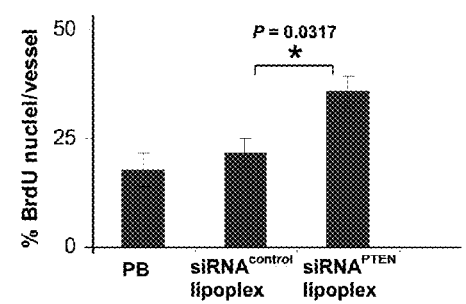

To test for PTEN gene silencing in vivo mice (4 per group) were treated with either PBS, naked siRNA$^{PTEN}$, siRNA$^{PTEN}$-lipoplex or lipid vehicle on three consecutive days by low pressure, tail vein injection (see Methods). On day four of treatment, BrdU was injected into the mice and two hours later the mice were sacrificed and BrdU incorporation was measured by immunohistological staining of liver sections for BrdU positive nuclei. The small size of the endothelial cells and the difficulties in detecting a reliable signal with phosphorylated Akt and PTEN specific antibodies did not allow to detect protein knock-down in situ. However, consistent with the observed cell specific delivery of fluorescence labeled siRNA to endothelial cells we observed a significant increase in BrdU positive nuclei in the liver endothelium only with liposomal siRNA$^{PTEN}$ (FIG. 19B). A similar experiment with tumor bearing mice revealed a significant increase as well in the number of BrdU-positive nuclei of the tumor endothelium after treatment with liposomally formulated active PTEN-siRNA (FIG. 19C). The inactive, fully methylated control molecule siRNA$^{control}$ did not cause an increase in BrdU incorporation relative to the PBS control group. We conclude from these data that stabilized PTEN-specific siRNAs formulated with cationic lipids are functional in vivo to induce gene silencing in endothelial cells after systemic administration.

The details of FIG. 19A are as follows. Transfection of a stabilized PTEN specific siRNA (10 nM) in vitro reduced PTEN protein level and increased phosphorylation of the downstream kinase Akt (P*-Akt) as revealed by immunoblot (right upper panel; PI 3-kinase subunits p110α, p85, unaffected loading control). siRNA$^{control}$ represents a fully methylated inactive siRNA$^{PTEN}$ molecule; ut, untreated cells. Increase of phosphorylated Akt was also visualized by immunofluorescence staining in NIH3T3 cells transfected with siRNA$^{PTEN}$ (phophorylated Akt, red; anti-α-tubulin as marker for cell morphology, green).

FIG. 19B depicts representative pictures (upper panels) and corresponding quantification (lower diagram) showing significant differences in the number of BrdU positive endothelial nuclei (arrows) in liver samples from animals treated with PBS, naked siRNA$^{PTEN}$, lipoplexed siRNA$^{PTEN}$, and cationic liposomes, respectively (two pictures shown for each treatment). Statistical significance: naked siRNA$^{PTEN}$ vs. siRNA$^{PTEN}$-lipoplex, *P=0.0286; liposomes vs. siRNA$^{PTEN}$-lipoplex, *P=0.0286.

The details of FIG. 19C are as follows: Sequence specificity of lipoplexed siRNA$^{PTEN}$ on DNA synthesis was confirmed with the BrdU assay for the tumor vasculature. Increased BrdU positive nuclei (arrow) were detected in tumor blood vessels (V) from animals treated with siRNA$^{PTEN}$-lipoplex in contrast to siRNA$^{control}$-lipoplex; Tu: tumor tissue. Quantification of BrdU-positive nuclei in endothelial cells was significantly increased: siRNA$^{control}$-lipoplex vs. siRNA$^{PTEN}$-lipoplex *P=0.032.

EXAMPLE 26

In Vivo Gene Silencing of CD31

To demonstrate in vivo siRNA mediated gene silencing more directly, we focused on targeting a gene selectively expressed in endothelial cells. We chose platelet-endothelial-cell adhesion molecule 1 (PECAM-1), also known as CD31, as a suitable target, since its expression is restricted to cells of the vasculature system, primarily to endothelial cells as well as platelets, monocytes, neutrophils, and selected T cells[21-23].

Figures 20A, 20B, 20C:
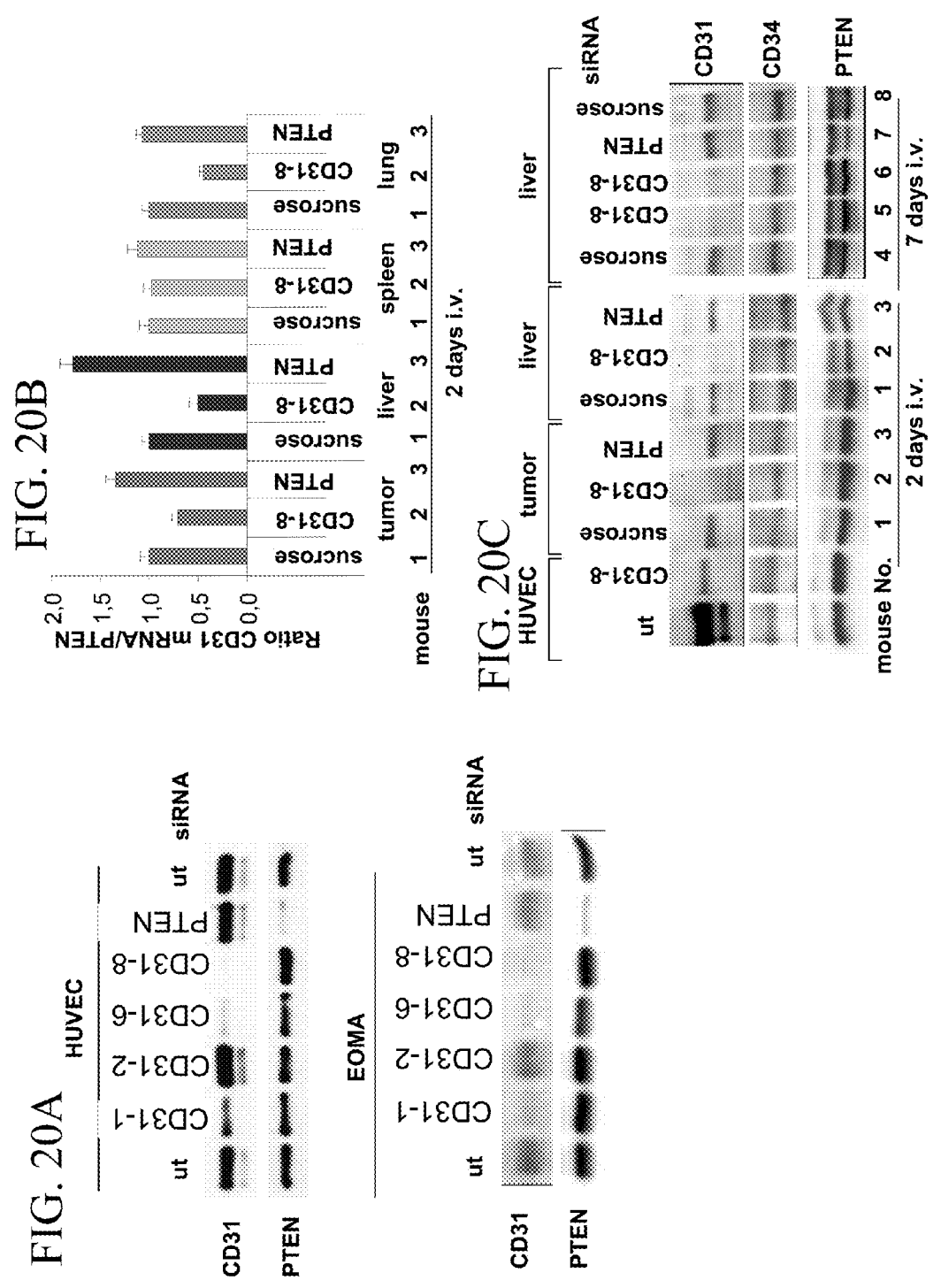

Screening of 2'-O-methyl modified siRNA molecules (c.f. Example 23) in mouse and human derived endothelial cell lines (HUVEC, EOMA) led to the identification of several potent human and mouse specific CD31-siRNA molecules (FIG. 20A). The most potent siRNA molecule, siRNA$^{CD31-8}$, was liposomally formulated as described in example 23 and systemically administered into tumor bearing mice for two or for seven days in a row. Control mice were treated with isotonic sucrose solution or with lipoplexed siRNA$^{PTEN}$ to test for specificity. After treatment, mice were sacrificed and gene silencing analyzed in various tissues by real time RT-PCR (TaqMan) and immunoblotting.

A reduction in the CD31 mRNA level in mice treated with siRNA$^{CD31-8}$-lipoplex was observed in tumor, liver and lung, but not in spleen tissue samples. The observed reduction in CD31 mRNA levels points to a RNAi-mode of action based on mRNA cleavage (FIG. 20B). In addition, a significant reduction of CD31 protein levels was detected in tumor and liver lysates from mice treated with siRNA$^{CD31-8}$-lipoplexes for two consecutive days in contrast to the unchanged protein levels observed in the control mice (FIG. 20C, left panel).

To test for specificity and equal loading we analyzed in parallel the protein levels of CD34, another endothelial cell marker protein, as well as PTEN in these lysates. We have also examined whole cell extracts from spleen and lung, but we did not detect reliable CD31 protein expression by immunoblot analysis in these organs (data not shown). CD31 protein knock-down was confirmed in an independent experiment on non-tumor bearing mice by seven daily i.v. injections (FIG. 20C, right panel).

Furthermore, the reduction in CD31 expression was also revealed in situ, by measuring differences in the microvessel density (MVD) for the endothelial markers CD31 and CD34 in a xenograft tumor mouse model. MVD measurement is a surrogate marker for tumor angiogenesis, and analyzed by immunohistochemical staining of blood vessels with CD31 or CD34 specific antibodies[24-26]. Formulated CD31 and PTEN specific siRNAs were administered by tail vein injection with regular volume (200 µl) and regular pressure on two days in tumor bearing mice (tumor size 800 mm$^3$). On day three the mice were sacrificed and the MVD was compared between consecutive sections after immunostaining with CD31 and CD34 antibodies, respectively.

Figure 20D:
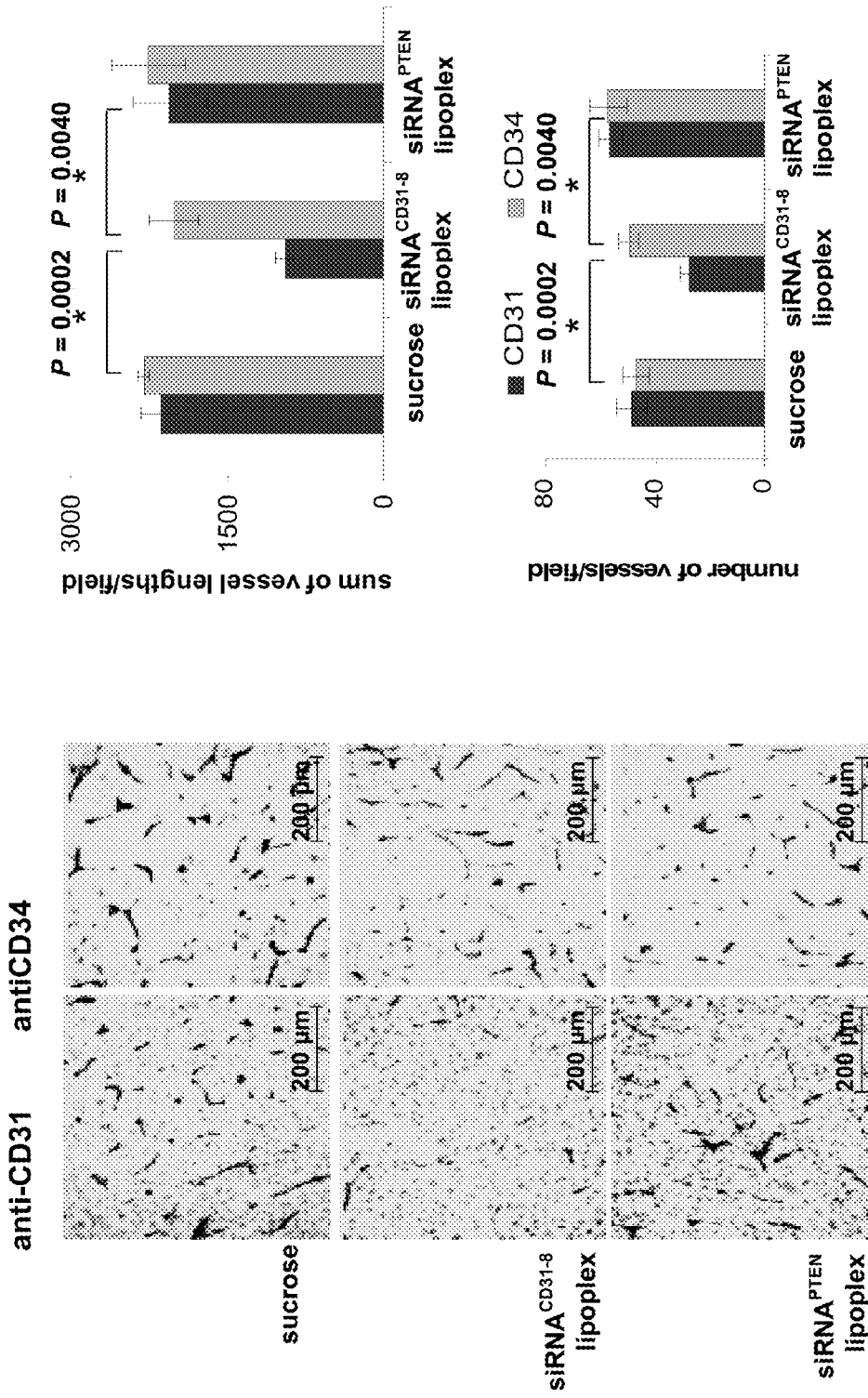
FIG. 20D shows the result of in vivo knock-down of CD 31 protein by direct immunostaining of paraffin tumor sections of mice treated with anti-CD 31 siRNA molecules.

The mice treated with the lipoplexed siRNA$^{CD31-8}$ showed a statistically significant decrease in the total amount of CD31 positive vessels as measured by total number of vessels as well as vessel length (FIG. 20D). Staining with CD34 specific antibodies did not reveal a change in MVD indicating again specific CD31 silencing. Both control groups, siRNA$^{PTEN}$ and isotonic sucrose treated, did not show differences in MVD assessment by either CD31 or CD34 staining. This result along with the molecular data on mRNA and protein knock-down indicates the specific reduction in CD31 expression, without a decrease in CD34 positive endothelial cells in response to systemic administration of lipoplexed siRNA$^{CD31-8}$. We concluded that in vivo CD31 (PECAM-1) gene silencing can be achieved by administration of cationic lipid formulated siRNAs in the vasculature of tumors and liver.

The details of FIG. 20A are as follows. FIG. 20A shows the identification of potent stabilized siRNAs for efficacious CD31 knock-down. HUVEC and murine EOMA cells were transfected with four different human, mouse specific siRNAs targeting CD31 (CD31-1, -2, -6, -8) and a control PTEN-siRNA. Specific protein knock-down was assessed by immunoblotting using anti-CD31 and anti-PTEN demonstrating highest efficacy of the siRNA$^{CD31-8}$ molecule.

The details of FIG. 20B are as follows. Mice treated on two consecutive days by i.v. injection of lipoplexed siRNA$^{CD31-8}$ showed reduction of CD31 mRNA levels in certain tissues as revealed by quantitative TaqMan RT-PCR. The relative amount of CD31 mRNA was normalized to PTEN mRNA levels.

The details of FIG. 20C are as follows. CD31 protein knock-down in mice treated systemically with siRNA$^{CD31-8}$-lipoplexes was confirmed by immunoblot analysis with extracts from liver and tumor using anti-CD31 antibody and anti-PTEN as well as anti-CD34 (another endothelial marker protein) to show equal protein loading. Mice were treated by i.v. injection on two (left panel: liver and tumor) or seven consecutive days (right panel: liver). CD31 Protein knock-down was observed in the siRNA$^{CD31}$-lipoplex treated animals in liver and tumor (see animal 2, left panel) but not in mice treated with isotonic sucrose solution or siRNA$^{PTEN}$-lipoplex treated mice (see animals 1, 3). With a treatment regimen of seven days substantial CD31 knock-down was observed in animals 5 and 6 in contrast to the control animals 4, 7 and 8 (right panel). The functionality of the siRNA$^{CD31-8}$-lipoplex used for the in vivo study were verified in parallel in HUVEC cells (10 nM siRNA).

The details of FIG. 20D are as follows. In vivo knock-down of CD31 protein was directly assessed by immunostaining of paraffin tumors sections from corresponding mice treated with isotonic sucrose, siRNA$^{CD31-8}$-lipoplex, and siRNA$^{PTEN}$-lipoplex. Consecutive sections were stained with anti-CD31 and anti-CD34 antibodies, respectively, to visualize the tumor vasculature. Reduced staining intensity for CD31, but not for CD34, was found in tumor section from mice treated with siRNA$^{CD31-8}$-lipoplex. MVD quantification (determined by number of vessels, upper diagram, and total lengths of vessels, lower diagram) of CD31 positive vessels showing a reduced MVD in the samples from siRNA$^{CD31-8}$-lipoplex treated mice. This difference was not observed by MVD measurement of CD34 positive vessels.

In connection with the anti-CD31 siRNA molecules disclosed herein it is to be noted that the disclosure of the present application is related to any anti-CD31 siRNA molecule and more preferably any anti-CD31 siRNA molecule exhibiting the modification pattern shown and described herein such as disclosed in connection with the anti CD31-8 siRNA molecule.

EXAMPLE 27

Efficacy of Systematically Administered siRNA$^{CD31}$-Lipoplex in Tumor Models

In this example, we addressed the question whether formulated siRNAs against CD31/PECAM-1 exhibit any therapeutic potential on tumor growth.

CD31 has been implicated in participating in diverse cellular mechanisms for vessel/platelet formation and function[23,27,28], but its potential contribution to neovascularization during tumor growth has not been addressed so far. The siRNA molecules chosen for the therapeutic approach comprised the specific siRNA$^{CD31-8}$ and siRNA$^{PTEN}$ as a control molecule. The siRNA$^{CD31-8}$- and siRNA$^{PTEN}$-lipoplexes for the in vivo efficacy studies were tested in a dose dependent transfection experiment in HUVEC prior to the in vivo experiment. Representative immunoblots demonstrating the functionality and potency of these siRNA-lipoplexes are shown in FIG. 21A.

Knock-down of CD31 protein was achieved with siRNA$^{CD31-8}$ in the low sub-nanomolar range with these formulations. Specificity of the siRNA$^{CD31-8}$ mediated gene silencing was demonstrated by probing for PTEN, phosphorylated Akt and CD34. Unlike transfections with siRNA$^{PTEN}$, the phosphorylation status of Akt was not affected in HUVEC cells by reduction in CD31. CD34 protein level was not changed with both lipoplexes when compared to untreated controls. The potential therapeutic effect of the systemically administered CD31-siRNA-lipoplex was investigated in mice bearing two different types of s.c. tumor xenografts.

First, we established a regimen which allowed for repeated systemic treatment using different lipoplex daily doses. Different total doses were achieved by administration of daily or bi-daily tail vein injections of 200 µl lipoplex solution (single dose 1.88 mg/kg/d siRNA; 14.5 mg/kg/d lipid). We did not observe severe toxic effects on the animal health status as assessed by monitoring changes in body weight as an overall marker of general health (FIG. 21B).

Subsequently, we analyzed the two dosing regimens representing either daily or bi-daily i.v. treatments in an efficacy study of siRNA$^{CD31-8}$-lipoplex on tumor growth inhibition. Both treatment regimens resulted in a clear inhibitory effect on tumor growth of an established, fast growing 3Y1-Ras$^{C12}$ s.c. xenograft with lipoplexed siRNA$^{CD31-8}$ (FIG. 21C). Notably, for this particular tumor xenograft the bi-daily regimen improved the inhibitory effect on tumor growth. This inhibition was statistically significant when compared to the siRNA$^{PTEN}$-lipoplex as well as the sucrose treated control groups (FIG. 21C).

In an additional experiment, systemic treatment of a slower growing s.c. PC-3 tumor xenograft with liposomal formulated siRNA$^{CD31-8}$ similarly caused a significant delay in tumor growth in contrast to the siRNA$^{PTEN}$ control (FIG. 21D). Taken together, the in vivo xenograft experiments clearly demonstrate that growth of tumor cells in nude mice can be suppressed by systemic administration of liposomal formulated CD31-siRNAs. These data also imply that CD31 (PECAM-1), a non-classical drug target, appears to be a suitable target for RNAi based anti-angiogenic therapeutic intervention.

The details of FIG. 21A are as follows. Quality control and efficacy testing of lipoplexed siRNA used for systemic tumor treatment in HUVEC. Immunoblotting using anti-CD31 antibody revealed a concentration dependent knock-down of CD31 in the case of siRNA$^{CD31-8}$, but not with control siRNA$^{PTEN}$. Reduction of CD31 had no effect on PI 3-kinase signaling as revealed by monitoring Akt phosphorylation status (P*-Akt), in contrast to the siRNA$^{PTEN}$ control. CD34 protein level was not affected.

The details of FIG. 21B are as follows. The influence of two different siRNA-lipoplex doses on body weight was monitored. Different siRNA$^{PTEN}$-lipoplex doses (squares: daily injection resulting in 1.88 mg/kg/d siRNA and 14.5 mg/kg/d lipid; diamonds: bi-daily injection (8 h apart), 3.75 mg/kg/d siRNA and 28.9 mg/kg/d) were administered for seven consecutive days, and changes in body weight were measured and plotted as mean value (n=7 mice). For comparison, body weights (mean±S.E.M.) of animals treated with isotonic sucrose solution (circles) are shown.

The details of FIGS. 21c and 21d are as follows Inhibition of tumor growth by CD31-siRNA-lipoplex treatment. Two different tumor xenografts (c: 3Y1-Ras$^{V12}$, d: PC-3) were established s.c. in nude mice (c: left diagram: n=8 mice per group, right, n=7 mice per group; d: n=8 per group). Mice bearing tumors were treated with siRNA$^{CD31-8}$-lipoplex (diamonds), siRNA$^{PTEN}$-lipoplexes (triangles) or isotonic sucrose (solid spheres). Different treatment regimens were applied as indicated; single arrow, daily; double arrows, bi-daily. (c) Growth of established 3Y1-Ras$^{V12}$ tumors was significantly inhibited by siRNA$^{CD31-8}$-lipoplex when compared to siRNA$^{PTEN}$-lipoplexes by applying the bi-daily dosing regimen (right diagram). (d) Growth of established PC-3 xenografts was significantly inhibited with siRNA$^{CD31-8}$-lipoplex in comparison to siRNA$^{PTEN}$-lipoplex treated administered as indicated (1.88 mg/kg/d siRNA; 14.5 mg/kg/d lipid; arrow). Data represent the means±S.E.M.; significance: *P<0.05 according to Mann-Whitney.

REFERENCES

The following references are inherent to examples 23 to 28 and are incorporated herein in their entirety by reference:
6. Elbashir, S. M. et al. Duplexes of 21-nucleotide RNAs mediate RNA interference in cultured mammalian cells. *Nature* 411, 494-8 (2001).
16. Czauderna, F. et al. Structural variations and stabilising modifications of synthetic siRNAs in mammalian cells. *Nucleic Acids Res* 31, 2705-16 (2003).
17. Chiu, Y. L. & Rana, T. M. RNAi in human cells: basic structural and functional features of small interfering RNA. *Mol Cell* 10, 549-61 (2002).
18. Zelphati, O. & Szoka, F. C., Jr. Mechanism of oligonucleotide release from cationic liposomes. *Proc Natl Acad Sci USA* 93, 11493-8 (1996).
19. Stambolic, V. et al. Negative regulation of PKB/Akt-dependent cell survival by the tumor suppressor PTEN. *Cell* 95, 29-39 (1998).
20. Klippel, A. et al. Activation of phosphatidylinositol 3-kinase is sufficient for cell cycle entry and promotes cellular changes characteristic of oncogenic transformation. *Mol Cell Biol* 18, 5699-711 (1998).

21. Watt, S. M., Gschmeissner, S. E. & Bates, P. A. PECAM-1: its expression and function as a cell adhesion molecule on hemopoietic and endothelial cells. *Leuk Lymphoma* 17, 229-44 (1995).
22. Newman, P. J. et al. PECAM-1 (CD31) cloning and relation to adhesion molecules of the immunoglobulin gene superfamily. *Science* 247, 1219-22 (1990).
23. Ilan, N. & Madri, J. A. PECAM-1: old friend, new partners. *Curr Opin Cell Biol* 15, 515-24 (2003).
24. Fox, S. B. & Harris, A. L. Histological quantitation of tumour angiogenesis. *Apmis* 112, 413-30 (2004).
25. Uzzan, B., Nicolas, P., Cucherat, M. & Perret, G. Y. Microvessel density as a prognostic factor in women with breast cancer: a systematic review of the literature and meta-analysis. *Cancer Res* 64, 2941-55 (2004).
26. Weidner, N., Semple, J. P., Welch, W. R. & Folkman, J. Tumor angiogenesis and metastasis—correlation in invasive breast carcinoma. *N Engl J Med* 324, 1-8 (1991).
27. Ilan, N., Mahooti, S. & Madri, J. A. Distinct signal transduction pathways are utilized during the tube formation and survival phases of in vitro angiogenesis. *J Cell Sci* 111 (Pt 24), 3621-31 (1998).
28. Solowiej, A., Biswas, P., Graesser, D. & Madri, J. A. Lack of platelet endothelial cell adhesion molecule-1 attenuates foreign body inflammation because of decreased angiogenesis. *Am J Pathol* 162, 953-62 (2003).
38. Leenders, F. et al. PKN3 is required for malignant prostate cell growth downstream of activated PI 3-kinase. *Embo J* 23, 3303-13 (2004).
39. Klippel, A., Escobedo, J. A., Hirano, M. & Williams, L. T. The interaction of small domains between the subunits of phosphatidylinositol 3-kinase determines enzyme activity. *Mol Cell Biol* 14, 2675-85 (1994).
40. Santel, A. & Fuller, M. T. Control of mitochondrial morphology by a human mitofusin. *J Cell Sci* 114, 867-74 (2001).

The features of the present invention disclosed in the specification, the claims and/or the drawings may both separately and in any combination thereof be material for realizing the invention in various forms thereof.

We claim:

1. A composition comprising a carrier and a liposome comprising at least one helper lipid component selected from the group consisting of phospholipids and steroids and a compound according to formula (I),

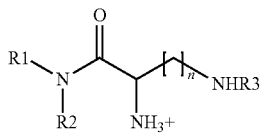
(I)

wherein $R_1$ and $R_2$ are each and independently selected from the group comprising alkyl;

n is any integer between 1 and 4;

$R_3$ is an acyl selected from the group comprising lysyl, ornithyl, 2,4-diaminobutyryl, histidyl and an acyl moiety according to formula (II)

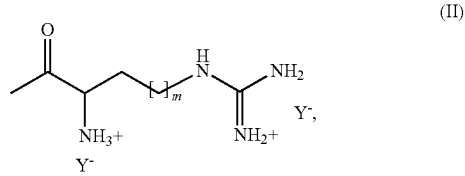
(II)

wherein m is any integer from 1 to 3 and $Y^-$ is a pharmaceutically acceptable anion.

2. The composition according to claim 1, wherein $R_1$ and $R_2$ are each and independently selected from the group comprising lauryl, myristyl, palmityl and oleyl.

3. The composition according to claim 1, wherein $R_1$ is lauryl and $R_2$ is myristyl or $R_1$ is palmityl and $R_2$ is oleyl.

4. The composition according to claim 1, wherein m is 1 or 2.

5. The composition according to claim 1, wherein $Y^-$ is selected from the group consisting of halogenids, acetate and trifluoroacetate.

6. The composition according to claim 1, wherein the compound is selected from the group consisting of:

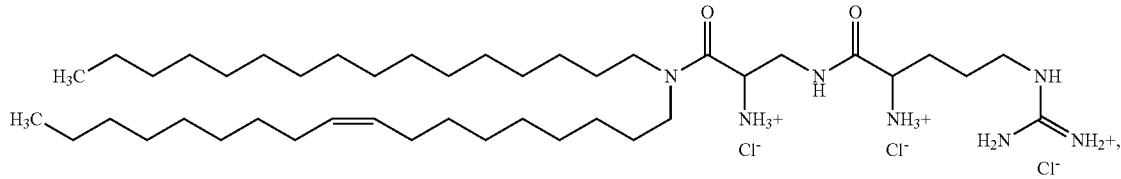

β-arginyl-2,3-diamino propionic acid-N-palmityl-N-oleyl-amide trihydrochloride

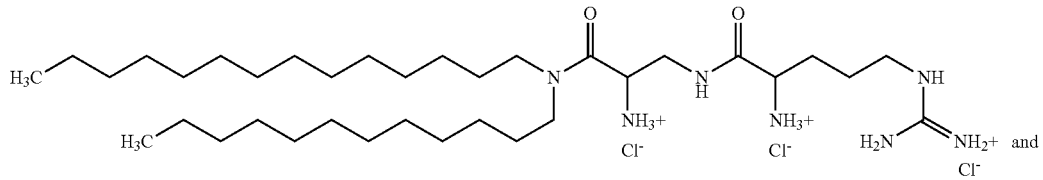

β-arginyl-2,3-diamino propionic acid-N-lauryl-N-myristyl-amide trihydrochloride

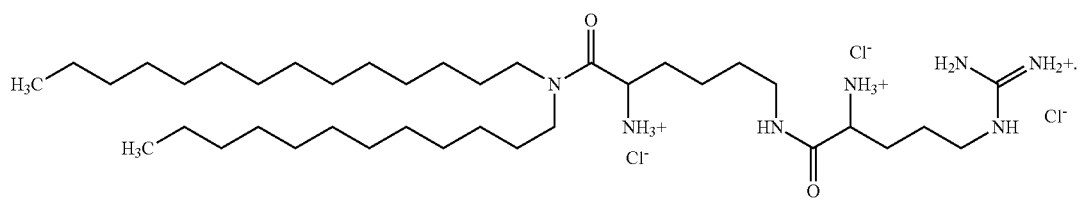

ε-arginyl-lysine-N-lauryl-N-myristyl-amide trihydrochloride

7. The composition according to claim 1, wherein the carrier is a pharmaceutically acceptable carrier.

8. The composition according to claim 1, wherein the liposome is associated with a nucleic acid.

9. The composition according to claim 8, wherein the nucleic acid is an oligonucleotide, polynucleotide or siRNA.

10. The composition according to claim 1, wherein the helper lipid component is selected from the group comprising 1,2-diphytanoyl-sn-glycero-3-phosphoethanolamine and 1,2-dioleyl-sn-glycero-3-phosphoethanolamine.

11. The composition according to claim 10, wherein the content of the helper lipid component is from about 20 mol % to about 80 mol % of the overall lipid content of the liposome.

12. The composition according to claim 1, wherein said at least one helper lipid comprises a moiety which is selected from the group comprising a PEG moiety, a HEG moiety, a polyhydroxyethyl starch (polyHES) moiety and a polypropylene moiety.

13. The composition according to claim 12, wherein the helper lipid comprising the PEG moiety is selected from the group comprising 1,2-distearoyl-sn-glycero-3-phosphoethanolamine, 1,2-dialkyl-sn-glycero-3-phosphoethanolamine; and Ceramide-PEG.

14. The composition according to claim 1, said liposome comprising:
   a) 50 mol % of β-arginyl-2,3-diamino propionic acid-N-palmityl-N-oleyl-amide trihydrochloride,
      48 mol % of 1,2-diphytanoyl-sn-glycero-3-phosphoethanolamine; and
      2 mol % 1,2-distearoyl-sn-glycero-3-phosphoethanolamine-PEG2000; or
   b) 50 mol % of β-L-arginyl-2,3-L-diamino propionic acid-N-palmityl-N-oleyl-amide trihydrocloride,
      49 mol % 1,2-diphytanoyl-sn-glycero-3-phosphoethanolamine; and
      1 mol % N(Carbonyl-methoxypolyethylenglycol-2000)-1,2-distearoyl-sn-glycero-3-phosphoethanolamine.

* * * * *

UNITED STATES PATENT AND TRADEMARK OFFICE
CERTIFICATE OF CORRECTION

PATENT NO. : 9,486,538 B2
APPLICATION NO. : 14/838791
DATED : November 8, 2016
INVENTOR(S) : Oliver Keil, Jorg Kaufmann and Ansgar Santel It is certified that error appears in the above-identified patent and that said Letters Patent is hereby corrected as shown below:

In the Specification

Column 8,
Line 52, "alkinyl Alky" should read --alkinyl. Alky--.

Column 18,
Lines 40-41, "of 99%" should read --of ≥ 99%--.
Line 45, "of 99%" should read --of ≥ 99%--.

Column 19,
Lines 62-63, "Tetra-Boc-M-Arginyl-[2,3-Diaminopropionic Acid-N-Palmityl-N-Oleyl-Amide]" should read --Tetra-Boc-[β-Arginyl-2,3-Diaminopropionic Acid-N-Palmityl-N-Oleyl-Amide]--.

Column 23,
Line 6, "β-Arginyl-Lysine-N-Lauryl-N-Myristyrl" should read --ε-Arginyl-Lysine-N-Lauryl-N-Myristyl--.
Lines 9-10, "tetra-Boc-[β-arginyl-lysin-N-lauryl-N-myristyl amide]" should read --tetra-Boc-[ε-arginyl-lysin-N-lauryl-N-myristyl amide]--.

Column 26,
Line 45, "was nM," should read --was 50 nM,--.
Line 57, "Peg" should read --PEG--.

Column 28,
Line 7, "aacguguagaaggcauccu-P" should read --aacguguagaaggcauccu-P--.
Line 9, "aggaugccuucuacacguu-P" should read --aggaugccuucuacacguu-P--.
Line 16, "uaaguucuagcuguggugg-P" should read --uaaguucuagcuguggugg-P--.
Line 17, "ccaccacagcuagaacuua-P" should read --ccaccacagcuagaacuua-P--.

Signed and Sealed this
Seventh Day of March, 2017

Michelle K. Lee
*Director of the United States Patent and Trademark Office*

CERTIFICATE OF CORRECTION (continued)
U.S. Pat. No. 9,486,538 B2

Column 29,
Line 50, "volume=(length×width)/2." should read --volume=(length×width$^2$)/2.--.

Column 37,
Line 55, "3Y1-Ras$^{C12}$" should read --3Y1-Ras$^{V12}$--.

Column 38,
Line 26, "follows Inhibition" should read --follows. Inhibition--.

SEQUENCE LISTING

```
<160> NUMBER OF SEQ ID NOS: 20

<210> SEQ ID NO 1
<211> LENGTH: 19
<212> TYPE: DNA
<213> ORGANISM: Artificial
<220> FEATURE:
<221> NAME/KEY: misc_feature
<223> OTHER INFORMATION: antisense strand of PTEN specific siRNA
<220> FEATURE:
<221> NAME/KEY: misc_feature
<223> OTHER INFORMATION: antisense strand of PTEN specific siRNA
      molecule

<400> SEQUENCE: 1
uaaguucuag cuguggugg                                                  19

<210> SEQ ID NO 2
<211> LENGTH: 19
<212> TYPE: DNA
<213> ORGANISM: Artificial
<220> FEATURE:
<221> NAME/KEY: misc_feature
<223> OTHER INFORMATION: sense strand of PTEN specific siRNA molecule

<400> SEQUENCE: 2
ccaccacagc uagaacuua                                                  19

<210> SEQ ID NO 3
<211> LENGTH: 19
<212> TYPE: DNA
<213> ORGANISM: Artificial
<220> FEATURE:
<221> NAME/KEY: misc_feature
<223> OTHER INFORMATION: sense strand of a T-Ras specific si RNA
      molecule
<220> FEATURE:
<221> NAME/KEY: misc_feature
<223> OTHER INFORMATION: strand of a T-Ras specific si RNA molecule

<400> SEQUENCE: 3
aacguguaga aggcauccu                                                  19

<210> SEQ ID NO 4
<211> LENGTH: 19
<212> TYPE: DNA
<213> ORGANISM: Artificial
```

```
<220> FEATURE:
<221> NAME/KEY: misc_feature
<223> OTHER INFORMATION: sense strand of a T-Ras specific si RNA
      molecule
<220> FEATURE:
<221> NAME/KEY: misc_feature
<223> OTHER INFORMATION: strand of a T-Ras specific si RNA molecule

<400> SEQUENCE: 4
aggaugccuu cuacacguu                                              19

<210> SEQ ID NO 5
<211> LENGTH: 19
<212> TYPE: DNA
<213> ORGANISM: Artificial
<220> FEATURE:
<221> NAME/KEY: misc_feature
<223> OTHER INFORMATION: sense strand of a PKN3 specific si RNA molecule

<400> SEQUENCE: 5
gagagccugu acugcgaga                                              19

<210> SEQ ID NO 6
<211> LENGTH: 19
<212> TYPE: DNA
<213> ORGANISM: Artificial
<220> FEATURE:
<221> NAME/KEY: misc_feature
<223> OTHER INFORMATION: antisense strand of a PKN3 specific si RNA
      molecule

<400> SEQUENCE: 6
ucucgcagua caggcucuc                                              19

<210> SEQ ID NO 7
<211> LENGTH: 19
<212> TYPE: DNA
<213> ORGANISM: Artificial
<220> FEATURE:
<221> NAME/KEY: misc_feature
<223> OTHER INFORMATION: sense strand of a PTEN specific si RNA molecule
<220> FEATURE:
<221> NAME/KEY: misc_feature
<223> OTHER INFORMATION: sense strand of a PTEN specific si RNA molecule

<400> SEQUENCE: 7
ccaccacagc uagaacuua                                              19

<210> SEQ ID NO 8
<211> LENGTH: 19
<212> TYPE: DNA
<213> ORGANISM: Artificial
<220> FEATURE:
<221> NAME/KEY: misc_feature
<223> OTHER INFORMATION: antisense strand of a PTEN specific si RNA
      molecule
<220> FEATURE:
<221> NAME/KEY: misc_feature
<223> OTHER INFORMATION: antisense strand of a PTEN specific si RNA
      molecule

<400> SEQUENCE: 8
uaaguucuag cugguggug                                              19

<210> SEQ ID NO 9
<211> LENGTH: 19
<212> TYPE: DNA
<213> ORGANISM: Artificial
```

```
<220> FEATURE:
<221> NAME/KEY: misc_feature
<223> OTHER INFORMATION: sense strand of a control PTEN specific si RNA
      molecule

<400> SEQUENCE: 9
ccaccacagc uagaacuua                                                  19

<210> SEQ ID NO 10
<211> LENGTH: 19
<212> TYPE: DNA
<213> ORGANISM: Artificial
<220> FEATURE:
<221> NAME/KEY: misc_feature
<223> OTHER INFORMATION: antisense strand of a control PTEN specific si
      RNA molecule

<400> SEQUENCE: 10
uaaguucuag cuguggugg                                                  19

<210> SEQ ID NO 11
<211> LENGTH: 19
<212> TYPE: DNA
<213> ORGANISM: Artificial
<220> FEATURE:
<221> NAME/KEY: misc_feature
<223> OTHER INFORMATION: sense strand of a PTEN specific si RNA molecule

<400> SEQUENCE: 11
ccaccacagc uagaacuua                                                  19

<210> SEQ ID NO 12
<211> LENGTH: 19
<212> TYPE: DNA
<213> ORGANISM: Artificial
<220> FEATURE:
<221> NAME/KEY: misc_feature
<223> OTHER INFORMATION: antisense strand of a PTEN specific si RNA
      molecule having Cy3 at the 3' end

<400> SEQUENCE: 12
uaaguucuag cuguggugg                                                  19

<210> SEQ ID NO 13
<211> LENGTH: 19
<212> TYPE: DNA
<213> ORGANISM: Artificial
<220> FEATURE:
<221> NAME/KEY: misc_feature
<223> OTHER INFORMATION: sense strand of a CD 31 specific si RNA
      molecule (CD31-1)

<400> SEQUENCE: 13
ccaacuucac cauccagaa                                                  19

<210> SEQ ID NO 14
<211> LENGTH: 19
<212> TYPE: DNA
<213> ORGANISM: Artificial
<220> FEATURE:
<221> NAME/KEY: misc_feature
<223> OTHER INFORMATION: antisense strand of a CD 31 specific si RNA
      molecule (CD31-1)

<400> SEQUENCE: 14
uucuggaugg ugaaguugg                                                  19
```

<210> SEQ ID NO 15
<211> LENGTH: 19
<212> TYPE: DNA
<213> ORGANISM: Artificial
<220> FEATURE:
<221> NAME/KEY: misc_feature
<223> OTHER INFORMATION: sense strand of a CD 31 specific si RNA
      molecule (CD31-2)

<400> SEQUENCE: 15
ggugauagcc ccgguggau                                              19

<210> SEQ ID NO 16
<211> LENGTH: 19
<212> TYPE: DNA
<213> ORGANISM: Artificial
<220> FEATURE:
<221> NAME/KEY: misc_feature
<223> OTHER INFORMATION: antisense strand of a CD 31 specific si RNA
      molecule (CD31-2)

<400> SEQUENCE: 16
auccaccggg gcuaucacc                                              19

<210> SEQ ID NO 17
<211> LENGTH: 19
<212> TYPE: DNA
<213> ORGANISM: Artificial
<220> FEATURE:
<221> NAME/KEY: misc_feature
<223> OTHER INFORMATION: sense strand of a CD 31 specific si RNA
      molecule (CD31-6)

<400> SEQUENCE: 17
ccacuucuga acuccaaca                                              19

<210> SEQ ID NO 18
<211> LENGTH: 19
<212> TYPE: DNA
<213> ORGANISM: Artificial
<220> FEATURE:
<221> NAME/KEY: misc_feature
<223> OTHER INFORMATION: antisense strand of a CD 31 specific si RNA
      molecule (CD31-6)

<400> SEQUENCE: 18
uguuggaguu cagaagugg                                              19

<210> SEQ ID NO 19
<211> LENGTH: 19
<212> TYPE: DNA
<213> ORGANISM: Artificial
<220> FEATURE:
<221> NAME/KEY: misc_feature
<223> OTHER INFORMATION: sense strand of a CD 31 specific si RNA
      molecule (CD31-8)

<400> SEQUENCE: 19
cagauacucu agaacggaa                                              19

<210> SEQ ID NO 20
<211> LENGTH: 19
<212> TYPE: DNA
<213> ORGANISM: Artificial
<220> FEATURE:
<221> NAME/KEY: misc_feature
<223> OTHER INFORMATION: antisense strand of a CD 31 specific si RNA
      molecule (CD31-8)

```
<400> SEQUENCE: 20
uuccguucua gaguaucug                    19
```